US 7,449,187 B2
Nov. 11, 2008

(12) United States Patent
Weber et al.

(54) **ALKALINE PROTEASE FROM *BACILLUS GIBSONII* (DSM 14391) AND WASHING AND CLEANING PRODUCTS COMPRISING SAID ALKALINE PROTEASE**

(75) Inventors: Angrit Weber, Sankt Augustin (DE); Angela Hellebrandt, Köln (DE); Susanne Wieland, Zons (DE); Karl-Heinz Maurer, Erkrath (DE); Beatrix Kottwitz, Erkrath (DE)

(73) Assignee: Henkel Kommanditgesellschaft auf Aktien (Henkel KGAA), Duesseldorf (DE)

( * ) Notice: Subject to any disclaimer, the term of this patent is extended or adjusted under 35 U.S.C. 154(b) by 512 days.

(21) Appl. No.: 10/872,166

(22) Filed: Jun. 18, 2004

(65) Prior Publication Data

US 2005/0003504 A1    Jan. 6, 2005

Related U.S. Application Data

(63) Continuation of application No. PCT/EP02/14125, filed on Dec. 12, 2002.

(30) Foreign Application Priority Data

Dec. 20, 2001 (DE) ................... 10162727

(51) Int. Cl.
- *A61K 39/00* (2006.01)
- *A61K 39/38* (2006.01)
- *A61K 39/02* (2006.01)
- *A61K 39/07* (2006.01)
- *A01N 63/00* (2006.01)
- *C07K 1/00* (2006.01)
- *C07K 14/00* (2006.01)
- *C07K 17/00* (2006.01)

(52) U.S. Cl. ............. 424/190.1; 424/184.1; 424/234.1; 424/246.1; 424/93.46; 424/93.4; 530/350

(58) Field of Classification Search ............... 424/184.1, 424/190.1, 234.1, 246.1, 93.46, 93.4; 530/350
See application file for complete search history.

(56) References Cited

U.S. PATENT DOCUMENTS

| | | |
|---|---|---|
| 3,623,957 A | 11/1971 | Feldman |
| 3,985,923 A | 10/1976 | Basadur |
| 4,116,885 A | 9/1978 | Derstadt et al. |
| 4,264,738 A | 4/1981 | Stepanov et al. |
| 4,820,439 A | 4/1989 | Rieck |
| 5,230,891 A | 7/1993 | Nakayama et al. |
| 5,252,604 A | 10/1993 | Nagy et al. |
| 5,340,735 A | 8/1994 | Christianson et al. |
| 5,344,770 A | 9/1994 | Hitomi et al. |
| 5,453,372 A | 9/1995 | Vetter et al. |
| 5,500,364 A | 3/1996 | Christianson et al. |
| 5,543,302 A | 8/1996 | Boguslawski et al. |
| 5,614,161 A | 3/1997 | Wilkens et al. |
| 5,665,587 A | 9/1997 | Aaslyng et al. |
| 5,691,295 A | 11/1997 | Maurer et al. |
| 5,705,169 A | 1/1998 | Stein et al. |
| 5,730,960 A | 3/1998 | Stein et al. |
| 5,739,091 A | 4/1998 | Kiesser et al. |
| 5,783,545 A | 7/1998 | Paatz et al. |
| 5,801,039 A | 9/1998 | Maurer et al. |
| 5,855,625 A | 1/1999 | Maurer et al. |
| 5,858,757 A | 1/1999 | Von Der Osten et al. |
| 5,880,080 A | 3/1999 | Amory et al. |
| 5,962,613 A | 10/1999 | Schade et al. |
| 5,972,873 A | 10/1999 | Nielsen et al. |
| 5,985,639 A | 11/1999 | Christianson et al. |
| 6,008,178 A | 12/1999 | Baileily et al. |
| 6,075,001 A | 6/2000 | Wilde |
| 6,083,898 A | 7/2000 | Meizner et al. |
| 6,087,315 A | 7/2000 | Rasmussen et al. |
| 6,110,884 A | 8/2000 | Rasmussen et al. |
| 6,121,226 A | 9/2000 | Gosselink et al. |
| 6,136,553 A | 10/2000 | Christianson et al. |
| 6,187,055 B1 | 2/2001 | Kottwitz et al. |
| 6,190,904 B1 | 2/2001 | Amory et al. |
| 6,193,960 B1 | 2/2001 | Metzger et al. |
| 6,197,589 B1 | 3/2001 | Maurer et al. |
| 6,197,740 B1 | 3/2001 | Shikata et al. |
| 6,228,827 B1 | 5/2001 | Penninger et al. |
| 6,379,394 B1 | 4/2002 | Chilou et al. |
| 6,407,247 B1 | 6/2002 | Habeck et al. |

(Continued)

FOREIGN PATENT DOCUMENTS

| | | |
|---|---|---|
| CA | 2 049 097 A1 | 2/1992 |
| CA | 2 306 376 | 10/2000 |
| CA | 2 326 758 | 5/2001 |
| DE | 1 940 488 | 2/1971 |
| DE | 1 617 141 | 4/1972 |
| DE | 2 121 397 | 11/1972 |

(Continued)

OTHER PUBLICATIONS

Bixler et al, Synthetic Vaccines, editor Ruth Arnon, 1987, pp. 39-71.*
Burgess et al, JCB, 1990, 111:2129-2138.*
Houghten et al, Vaccines86, editor Brown et al, 1986, pp. 21-25.*
Bowie et al, Science, Mar. 16, 1990, 247:1306-1310.*
Kumar et al, PNAS USA, 1990, 87:1337-1341.*
Lazar et al, Molecular and Cellular Biology, Mar. 1988, 8:1247-1252.*

(Continued)

*Primary Examiner*—N. M Minnifield
(74) *Attorney, Agent, or Firm*—Woodcock Washburn LLP

(57) ABSTRACT

Described herein is a novel alkaline protease of the subtilisin type from *Bacillus gibsonii* (DSM 14391), as well as related proteins and derivatives thereof. Also described are washing and cleaning products comprising this novel alkaline protease, related proteins and derivatives thereof, as well as corresponding washing and cleaning products and methods, along with further possible technical uses.

13 Claims, 3 Drawing Sheets

U.S. PATENT DOCUMENTS

| | | |
|---|---|---|
| 6,417,152 B1 | 7/2002 | Kottwitz et al. |
| 6,509,021 B1 | 1/2003 | Weiss et al. |
| 6,703,357 B1 | 3/2004 | Maurer et al. |
| 6,777,218 B1 * | 8/2004 | Mikkelsen et al. .......... 435/220 |
| 7,262,042 B2 * | 8/2007 | Weber et al. ................ 435/212 |
| 7,320,887 B2 * | 1/2008 | Kottwitz et al. ............ 435/221 |
| 2003/0215800 A9 | 11/2003 | Dupret et al. |
| 2004/0005695 A1 | 1/2004 | Miksch et al. |
| 2005/0003504 A1 * | 1/2005 | Weber et al. ................ 435/221 |
| 2005/0003985 A1 * | 1/2005 | Kottwitz et al. ............ 510/320 |
| 2005/0009167 A1 * | 1/2005 | Weber et al. ................ 435/221 |
| 2005/0026269 A1 * | 2/2005 | Kottwitz et al. ............ 435/222 |
| 2005/0043198 A1 * | 2/2005 | Weber et al. ................ 510/320 |
| 2005/0113273 A1 * | 5/2005 | Weber et al. ................ 510/320 |
| 2005/0281773 A1 * | 12/2005 | Wieland et al. .......... 424/70.14 |
| 2005/0282261 A1 * | 12/2005 | Sauter et al. ................ 435/183 |
| 2007/0010417 A1 * | 1/2007 | Wieland et al. ............ 510/320 |
| 2007/0128129 A1 * | 6/2007 | Stehr et al. .................... 424/50 |
| 2007/0196898 A1 * | 8/2007 | Nielsen et al. ............. 435/69.1 |
| 2007/0212706 A1 * | 9/2007 | Wieland et al. ................ 435/6 |

FOREIGN PATENT DOCUMENTS

| | | |
|---|---|---|
| DE | 2 253 063 | 5/1973 |
| DE | 2 200 911 | 10/1973 |
| DE | 28 57 292 A1 | 2/1980 |
| DE | 33 24 258 A1 | 1/1984 |
| DE | 40 13 142 A1 | 10/1991 |
| DE | 44 11 223 A1 | 10/1995 |
| DE | 44 43 177 A1 | 6/1996 |
| DE | 196 01 063 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 196 50 537 A1 | 6/1998 |
| DE | 197 09 284 A1 | 9/1998 |
| DE | 197 12 033 A1 | 9/1998 |
| DE | 199 18 267 A1 | 10/2000 |
| DE | 101 21 463 A1 | 2/2003 |
| DE | 101 53 792 A1 | 5/2003 |
| EP | 0 006 638 B1 | 4/1984 |
| EP | 0 080 748 B1 | 7/1985 |
| EP | 0 080 223 B1 | 7/1986 |
| EP | 0 066 944 B1 | 11/1986 |
| EP | 0 126 505 B1 | 1/1987 |
| EP | 0 272 033 A2 | 6/1988 |
| EP | 0 283 075 A2 | 9/1988 |
| EP | 0 028 865 B2 | 3/1989 |
| EP | 0 380 362 A1 | 8/1990 |
| EP | 0 253 567 B1 | 12/1990 |
| EP | 0 241 985 B1 | 1/1991 |
| EP | 0 405 901 A1 | 1/1991 |
| EP | 0 472 042 A1 | 2/1992 |
| EP | 0 185 427 B1 | 3/1992 |
| EP | 0 199 404 B1 | 6/1992 |
| EP | 0 274 907 B1 | 8/1992 |
| EP | 0 525 610 A2 | 2/1993 |
| EP | 0 378 262 B1 | 12/1993 |
| EP | 0 241 984 B1 | 3/1994 |
| EP | 0 378 261 B1 | 7/1994 |
| EP | 0 251 446 B1 | 12/1994 |
| EP | 0 357 280 B1 | 2/1996 |
| EP | 0 516 200 B1 | 7/1996 |
| EP | 0 728 749 A2 | 8/1996 |
| EP | 0 328 229 B2 | 10/1996 |
| EP | 0 755 999 A1 | 1/1997 |
| EP | 0 583 534 | 3/1997 |
| EP | 0 525 239 B1 | 7/1997 |
| EP | 0 656 058 B1 | 12/1997 |
| EP | 0 693 471 B1 | 1/1998 |
| EP | 0 694 521 B1 | 1/1998 |
| EP | 0 818 450 A1 | 1/1998 |
| EP | 0 533 239 B1 | 4/1998 |
| EP | 0 583 339 B1 | 7/1998 |
| EP | 0 736 084 B1 | 9/1998 |
| EP | 0 581 751 B1 | 12/1998 |
| EP | 0 587 550 B1 | 12/1998 |
| EP | 0 702 712 B1 | 12/1998 |
| EP | 0 164 514 B1 | 6/1999 |
| EP | 0 578 712 B1 | 7/1999 |
| EP | 0 945 502 A1 | 9/1999 |
| EP | 0 828 762 B1 | 10/1999 |
| EP | 0 493 398 B1 | 12/1999 |
| EP | 0 791 046 B1 | 4/2000 |
| EP | 0 995 801 A1 | 4/2000 |
| EP | 0 130 756 B2 | 6/2000 |
| EP | 0 747 471 B1 | 8/2000 |
| EP | 1 029 920 A1 | 8/2000 |
| EP | 0 601 005 B1 | 11/2000 |
| EP | 0 780 466 B1 | 6/2001 |
| EP | 0 755 944 B1 | 10/2001 |
| GB | 1 154 730 | 6/1969 |
| GB | 1 243 784 | 8/1971 |
| GB | 1 263 765 | 2/1972 |
| GB | 1 377 092 | 12/1974 |
| GB | 2 123 848 A | 2/1984 |
| JP | 2005 534280 A1 * | 11/2005 |
| WO | WO 88/07581 A1 | 10/1988 |
| WO | WO 88/08028 A1 | 10/1988 |
| WO | WO 88/08033 A1 | 10/1988 |
| WO | WO 89/06279 A1 | 7/1989 |
| WO | WO 89/09819 A1 | 10/1989 |
| WO | WO 89/09830 A1 | 10/1989 |
| WO | WO 91/00334 A1 | 1/1991 |
| WO | WO 91/00345 A1 | 1/1991 |
| WO | WO 91/02792 A1 | 3/1991 |
| WO | WO 91/06637 A1 | 5/1991 |
| WO | WO 92/11348 A1 | 7/1992 |
| WO | WO 92/19707 A1 | 11/1992 |
| WO | WO 92/19729 A1 | 11/1992 |
| WO | WO 92/21760 A1 | 12/1992 |
| WO | WO 93/00418 | 1/1993 |
| WO | WO 93/07276 A1 | 4/1993 |
| WO | WO 93/18140 A1 | 9/1993 |
| WO | WO 94/02618 A1 | 2/1994 |
| WO | WO 94/27970 A1 | 12/1994 |
| WO | WO 94/28102 A1 | 12/1994 |
| WO | WO 94/28103 A1 | 12/1994 |
| WO | WO 94/29426 A1 | 12/1994 |
| WO | WO 95/00626 A1 | 1/1995 |
| WO | WO 95/07350 A1 | 3/1995 |
| WO | WO 95/07688 A1 | 3/1995 |
| WO | WO 95/07991 A2 | 3/1995 |
| WO | WO 95/10591 A1 | 4/1995 |
| WO | WO 95/10592 A1 | 4/1995 |
| WO | WO 95/12655 A1 | 5/1995 |
| WO | WO 95/14075 A1 | 5/1995 |
| WO | WO 95/14759 A1 | 6/1995 |
| WO | WO 95/17498 A1 | 6/1995 |
| WO | WO 95/22625 A1 | 8/1995 |
| WO | WO 95/23221 A1 | 8/1995 |
| WO | WO 95/26398 A1 | 10/1995 |
| WO | WO 95/29979 A1 | 11/1995 |
| WO | WO 95/30010 A1 | 11/1995 |
| WO | WO 95/30011 A2 | 11/1995 |
| WO | WO 95/32232 A1 | 11/1995 |
| WO | WO 96/02653 A1 | 2/1996 |
| WO | WO 96/25489 A1 | 8/1996 |
| WO | WO 96/28556 A2 | 9/1996 |
| WO | WO 96/28557 A2 | 9/1996 |
| WO | WO 96/28558 A1 | 9/1996 |
| WO | WO 96/28566 A2 | 9/1996 |
| WO | WO 96/31589 A1 | 10/1996 |

| | | | |
|---|---|---|---|
| WO | WO 96/34935 A2 | 11/1996 |
| WO | WO 97/00392 A1 | 1/1997 |
| WO | WO 97/05227 A1 | 2/1997 |
| WO | WO 97/07770 A1 | 3/1997 |
| WO | WO 97/09446 A1 | 3/1997 |
| WO | WO 97/18287 A1 | 5/1997 |
| WO | WO 97/20078 A1 | 6/1997 |
| WO | WO 97/24177 A1 | 7/1997 |
| WO | WO 97/25399 A1 | 7/1997 |
| WO | WO 97/28243 A1 | 8/1997 |
| WO | WO 97/31085 A1 | 8/1997 |
| WO | WO 97/32958 A1 | 9/1997 |
| WO | WO 97/43377 A1 | 11/1997 |
| WO | WO 98/13459 A1 | 4/1998 |
| WO | WO 98/13460 A1 | 4/1998 |
| WO | WO 98/13462 A1 | 4/1998 |
| WO | WO 98/13483 A1 | 4/1998 |
| WO | WO 98/17764 A1 | 4/1998 |
| WO | WO 98/20116 A1 | 5/1998 |
| WO | WO 98/22565 A1 | 5/1998 |
| WO | WO 98/27230 A1 | 6/1998 |
| WO | WO 98/30669 A1 | 7/1998 |
| WO | WO 98/45396 A1 | 10/1998 |
| WO | WO 99/06515 A1 | 2/1999 |
| WO | WO 99/06516 A1 | 2/1999 |
| WO | WO 99/18219 A1 | 4/1999 |
| WO | WO 99/20723 A2 | 4/1999 |
| WO | WO 99/20726 A1 | 4/1999 |
| WO | WO 99/20727 A1 | 4/1999 |
| WO | WO 99/20769 A2 | 4/1999 |
| WO | WO 99/27082 A1 | 6/1999 |
| WO | WO 99/43780 A1 | 9/1999 |
| WO | WO 99/48918 A1 | 9/1999 |
| WO | WO 99/49056 A1 | 9/1999 |
| WO | WO 99/49057 A1 | 9/1999 |
| WO | WO 99/57154 A1 | 11/1999 |
| WO | WO 99/57159 A1 | 11/1999 |
| WO | WO 99/57250 A1 | 11/1999 |
| WO | WO 99/57254 A1 | 11/1999 |
| WO | WO 00/01826 A2 | 1/2000 |
| WO | WO 00/01831 A2 | 1/2000 |
| WO | WO 00/05352 A1 | 2/2000 |
| WO | WO 00/09679 A1 | 2/2000 |
| WO | WO 00/18865 A1 | 4/2000 |
| WO | WO 00/24924 A2 | 5/2000 |
| WO | WO 00/36069 A1 | 6/2000 |
| WO | WO 00/37599 A1 | 6/2000 |
| WO | WO 00/37621 A1 | 6/2000 |
| WO | WO 00/37627 A1 | 6/2000 |
| WO | WO 00/39306 A2 | 7/2000 |
| WO | WO 00/42145 A1 | 7/2000 |
| WO | WO 00/57155 A1 | 9/2000 |
| WO | WO 00/71683 A1 | 11/2000 |
| WO | WO 00/71691 A1 | 11/2000 |
| WO | WO 01/00764 A2 | 1/2001 |
| WO | WO 01/07575 A2 | 2/2001 |
| WO | WO 01/16285 A2 | 3/2001 |
| WO | WO 01/38471 A1 | 5/2001 |
| WO | WO 01/68821 A1 | 9/2001 |
| WO | WO 01/68821 A2 | 9/2001 |
| WO | WO 01/75087 A2 | 10/2001 |
| WO | WO 01/81597 A1 | 11/2001 |
| WO | WO 02/088340 A2 | 11/2002 |
| WO | WO 2003/054184 | * 7/2003 |
| WO | WO 2003/054185 | * 7/2003 |
| WO | WO 2003/055974 | * 7/2003 |
| WO | WO 2003/056017 | * 7/2003 |
| WO | WO 2005/063974 | * 7/2005 |
| WO | WO 2005/103244 | * 11/2005 |
| WO | WO 2005/118793 | * 12/2005 |
| WO | WO 2007/131657 A2 | * 11/2007 |

OTHER PUBLICATIONS

Creighton, In: Proteins, 1984, pp. 314-315.*
Creighton, In: Protein Structure a practical approach, 1989, pp. 184-186.*
Nosoh et al, Protein Stability and Stabilization Through Protein Engineering, 1991, pp. 197-217.*
Kuhn et al, Biochemistry, 1998, 37:13446-13452.*
Keay et al, Biotechnology and Bioengineering, 1970, vol. XII, pp. 213-249.*
Chaparro-Riggers et al, J. Molecular Catalysis B: Enzymatic, 2005, 35:74-77.*
Saeki et al, J. Bioscience and Bioengineering, 2007, 103:6:501-508.*
Khalil et al, Enzyme and Microbial Technology, 2003, 32:294-304.*
Gupta et al, Appl. Microbial Biotechnol., 2002, 59:15-32.*
Moriyama et al, Biosci. Biotechnol. Biochem., 1998, 62/2:268-274.*
Keay et al, BBRC, 1969, 34/5:600-604 abstract only.*
Aehle et al, J. Biotechnology, 1993, 28/1:31-40.*
Hakamada et al, J. Fermentation and Bioengineering, 1994, 78/1:105-108 abstract only.*
Yamane et al, "Structure of a new alkaline serine protease (M-protease) from *Bacillus* sp. KSM-K16". Acta Crystallogr., Swis-sprot Accession No. Q99405. XP002235847 (Feb. 1, 1995).
Masui et al., "Rational design for stabilization and optimum pH shift of serine protease AprN", J. Ferment. Bioeng., EMBL Accession No. AB005792. XP002235848 (1998).
Kaneko et al., "Molecular cloning of the structural gene for alkaline elastase YaB, a new subtilisin produced by an alkalophilic *Baciullus* strain", J. Bacteriol, EMBL Accession No. M28537 XP002235849 (1989).
Siezen et al., "Subtilases:The Superfamily of Subtilisin-Like Serine Proteases", Protein Science Cambridge University Press, Cambridge, GB vol. 6. No. 3, pp. 501-523, XP000856203 (1997).
Siezen et al., "Subtilaese:Subtilisin-like Proteases", Subtilisin Enzymes, Plenum Press, New New York and London, pp. 75-93 (1996).
Vasantha et al, "Genes for Alkaline Protease and Neutral Protease from *Baci amyloliquefaciens* Contain a Large Open Reading frame Between the Regions Coding for Signal Sequence and Mature Protein", Journal of Bacteriology, vol. 159, No. 3, pp. 811-819 (Sep. 1984).
Wells et al., "Cloning, sequencing, and secretion of *Bacillus amloliquefaciens* subtilisin in *Bacillus subtilis*", Nucleic Acids Research, vol. 11 No. 22, pp. 7911-7925 (1983).
Smith et al., "The Complete Sequence; Comparison with Subtilisin BPN'; Evolutionary Relationships", The Journal of Biological Chemistry, vol. 243, No. 9, pp. 2184-2191 (May 10, 1968).
Jacobs et al., "Cloning, sequencing and expression of sbutilisin Carlsberg from *Bacillus licheniformis*", Nucleic Acids Research, vol. 13, No. 24, pp. 8913-8926 (1985).
Goddette et al., "The Crystal Structure of the *Bacillus lentus* Alkaline Protease, Subtilisin BL, at 1·4 ÅResolution", Journal Molecular Biology, vol. 228, pp. 580-595 (1992).
Nedkov et al., "Determination of the Complete Amino-Acid Sequence of Subtilisin DY and its Comparison with the Primary Structures of the Subtilisins BPN', Carlsberg and *Amylosaccharticus*", Biol. Chem. Hoppe-Seyler, vol. 366, pp. 421-430 (Apr. 1985).
Meloun et al., "Complete primary structure of thermitase from *Thermoactinomyces vulgaris* and its structural features related to the subtilisin-type proteinases", FEBS Letter, vol. 183, No. 2. pp. 195-200 (1983).
Jany et al., "Proteinase K from *Tritirachium album* Limber" Biol. Chem. Hoppe-Seyler, vol. 366, pp. 485-492 (May 1985).
Zhao et al., "Molecular evolution by staggered extension process (StEP) in vitro recombination" Nature Biotechnology, vol. 16, pp. 258-261 (1998).
Shao et al., "Random-priming in vitro recombination: an effective tool for directed evolution", Nucleic Acids Research, vol. 26, No. 2, pp. 681-683 (1998).

W. Stemmer, "Rapid evolution of a protein in vitro by DNA shuffling", Letters to Nature, vol. 370 pp. 389-391 (1994).

Coco et al., "DNA shuffling method for generating highly recombined genes and evolved enzymes", Nat. Biotechnol., vol. 19, pp. 354-359 (2001).

Powell et al., "Gerichtete Evolution und Biokatalyse", Angew, Chem., vol. 113, pp. 4069-4080 (2001).

"Lexikon der Biochemie", Spektrum Akademischer Verlag, Berlin, vol. 1, pp. 267-271 (1999).

"Lexikon der Biochemie", Spektrum Akademischer Verlag, Berlin, vol. 2, pp. 227-229 (1999).

Lipman et al., "Rapid and Sensitive Protein Similarity Searches", Science, vol. 227, pp. 1435-1441 (Mar. 27, 1985).

Fritsch et al., "Molecular Cloning: a laboratory Manual", Cold Spring Harbour Laboratory Press New York (1989).

von P.N. Bryan, "Protein Engineering", Biochim, Biophys. Acta, vol. 1543, pp. 203-222 (2000).

Helmut Uhlig, Handbook "Industrial Enzymes and Their Applications", Wiley-Verlag, New York (1998).

van Raay et al, Tenside-Detergents, vol. 7, pp. 125-132 (1970) [English summary included on p. 131].

K. H. Wallhauber, "Praxis der Sterilisation, Desinfektion-Konservierung: Keimidentifizierung-Betriebshygiene", 5th Edition, Stuttgart, New York:Thieme (1995).

Finkel, SOFW Journal, vol. 122, pp. 543-548 (1996) [English summary included on p. 543].

R. Breier, "Rein enzymatische Antifilzausrustung von Wolle nach dem Lanazym-Verfahren", Melliand Textilberichte, pp. 298-302 (2000).

Rompp, Lexikon Chemie, Version 2.0, Stuttgart/New York; George Thieme Verlag (1999) 1page.

T. Egelrud et al., Acta Derm. Venerol., vol. 71, pp. 471-474 (1991).

Bernhard et al, "Bacteriocin and Antibiotic Resistance Plasmids in *Bacillus cereus* and *Bacillus subtilis*", Journal of Bacteriology, vol. 133, No. 2, pp. 897-903 (1978).

Kawamura et al., "Construction of a *Bacillus subtilis* Double Mutant Deficient in Extracellular Alkaline and Neutral Proteases", J. Bacteriol., vol. 160, pp. 442-444 (Oct. 1984).

Genbank Databank Accession No. AX287283 of Nov. 21, 2001 and amino acid sequence comparison of the recombinant clone 4D10 with a)SEQ ID 2 and b)SEQ ID No. 2__115-384 as Well as nucleotide sequence comparison of the clone 4D10 (Sequnce 16) with SEQ ID No. 1.

Genbank Database Accession No. AX250603 of Oct. 5, 2001 and amino acid sequence comparison with SEQ ID No. 2__115-384 as well as nucleotide sequence comparison with SEQ ID No. 1__343-1152.

* cited by examiner

Figure 1/Part 1

```
                                                                                      70
 3  QQTVPWGITR VQAPAVHNRG VTGSGVRVAI LDSGIST.HS DLTIRGGASF VPGEPT.TAD LNGHGTHVAG
 4  .QSVPWGISR VQAPAAHNRG LTGSGVKVAV LDTGIST.HP DLNIRGGASF VPGEPS.TQD GNGHGTHVAG
 5  AQSVPWGISR VQAPAAHNRG LTGSGVKVAV LDTGIST.HP DLNIRGGASF VPGEPS.TQD GNGHGTHVAG
 6  AQSVPWGISR VQAPAAHNRG LTGSGVKVAV LDTGIST.HP DLNIRGGASF VPGEPS.TQD GNGHGTHVAG
 7  .QTVPWGINR VQAPIAQSRG FTGTGVRVAV LDTGISN.HA DLRIRGGASF VPGEPN.ISD GNGHGTQVAG
 8  .QVTPWGITR VQAPTAWTRG YTGTGVRVAV LDTGIST.HP DLNIRGGVSF VPGEPS.YQD GNGHGTHVAG
 9  .QTVPWGIPY IYSDVVHRQG YFGNGVKVAV LDHIRGGVSF ISTENT.YVD YNGHGTHVAG
10  AQSVPYGVSQ IKAPALHSOG YTGSNVKVAV IDSGIDSSHP DLKVAGGASM VPSETNPFQD NNSHGTHVAG
11  IKAPALHSQG IKAPALHSQG YTGSNVKVAV IDSGIDSSHP DLNVRGGASF VPSETNPYQD GSSHGTHVAG
12  AQSVPYGISQ IKAPALHSQG YTGSNVKVAV YTGSNVKVAV IDSGIDSSHP DLNVRGGASF VPSETNPYQD GSSHGTHVAG
13  AQSVPYGISQ IKAPALHSQG YTGSNVKVAV IDSGIDSSHP DLNVRGGASF VPSETNPYQD GSSHGTHVAG
14  AQSVPYGISQ IKAPALHSQG YTGSNVKVAV IDSGIDSSHP DLNVRGGASF VPSETNPYQD GSSHGTHVAG
15  AQSVPYGISQ IKAPALHSQG YTGSNVKVAV IDSGIDSSHP DLNVRGGASF VPSETNPYQD GSSHGTHVAG
16  AQTVPYGIPL IKADKVQAQG FKGANVKVAV LDTGIQASHP DLNVVGGASF VAGEAY.NTD GNGHGTHVAG 140
 3  TVAALNNSIG VIGVAPSADL YAVKVLGANG RGSVSGIAQG LEWAAANNMH IANMSLGSDA PSITLERAVN
 4  TIAALNNSIG VLGVAPNAEL YAVKVLGASG SGSVSSIAQG LEWAGNNGMH VANLSLGSPS PSATLEQAVN
 5  TIAALNNSIG VLGVAPSAEL YAVKVLGADG RGAISSIAQG LEWAGNNGMH VANLSLGSPS PSATLEQAVN
 6  TIAALNNSIG VLGVAPSAEL YAVKVLGASG SGSVSSIAQG LEWAGNNGMH VANLSLGSPS PSATLEQAVN
 7  TIAALNNSIG VLGVAPNVDL YGVKVLGASG SGSISGIAQG LQWAANNGMH IANMSLGSSA GSATMEQAVN
 8  TVAALNNSIG VVGVAPNAEL YAVKVLGANG SGSVSSIAQG LQWTAQNNIH VANLSLGSPV GSQTLELAVN
 9  TVAALNNSYG VLGVAPGAEL YAVKVLDRNG SGSHASIAQG IEWAMNNGMD IANMSLGSPS GSTTLQLAAD
10  TVAALNNSIG VLGVAPSASL YAVKVLGADG SGQYSWIING IEWAIANNMD VINMSLGGPS GSAALKAAVD
11  TIAALNNSIG VLGVAPSASL YAVKVLDSTG SGQYSWIING IEWAISNNMD VINMSLGGPT GSTALKTVVD
12  TIAALNNSIG VLGVSPSASL YAVKVLDSTG SGQYSWIING IEWAISNNMD VINMSLGGPS GSTALKTVVD
13  TIAALNNSIG VLGVSPSASL YAVKVLDSTG SGQYSWIING IEWAISNNMD VINMSLGGPS GSTALKTVVD
14  TIAALNNSIG VLGVAPSSAL YAVKVLDSTG SGQYSWIING IEWAISNNMD VINMSLGGPS GSTALKTVVD
15  TIAALNNSIG VLGVSPSASL YAVKVLNSSG SGQYSWIING IEWAITNGMD VINMSLGGPT GSTALKTVVD
16  TVAALDNTTG VLGVAPSVSL YAVKVLNSSG SGTYSGIVSG IEWATTNGMD VINMSLGGPS GSTAMKQAVD
```

Figure 1/Part 2

```
     141                                                                                      210
3    YATSRGVLVI AATGNNG.... .TGSIGYPAR YANAMAVGAT DQNNRRASFS QYGTGIDIVA PGVGIQSTYL
4    SATSRGVLVV AASGNSG.... .AGSISYPAR YANAMAVGAT DQNNRRASFS QYGAGLDIVA PGVNVQSTYP
5    SATSRGVLVV AASGNSG.... .AGSISYPAR YANAMAVGAT DQNNNRASFS QYGAGLDIVA PGVNVQSTYP
6    SATSRGVLVV AASGNSG.... .ASSISYPAR YANAMAVGAT DQNNNRASFS QYGAGLDIVA PGVGIQSTYP
7    QATNAGVLVV AASGNSG.... .SGTVSYPAR YANALAVGAT DQNNNRASFS QYGTGLNIVA PGVGIQSTYP
8    QATASGVLVV AASGNSG.... .AGNVGFPAR YANAMAVGAT DQNNNRATFS QYGAGLDIVA PGVGVQSTVP
9    RARNAGVLLI GAAGNSGQQG GSNNMGYPAR YASVMAVGAV DQNGNRANFS SYGSELEIMA PGVNINSTYL
10   KAVSSGIVVA AAAGNEGSSG STSTVGYPAK YPSTIAVGAV NSSNQRASFS SVGSELDVMA PGVSIQSTLP
11   KAVASGVVVV AAAGNEGTSG SSSTVGYPGK YPSVIAVGAV DSSNQRASFS SVGPELDVMA PGVSIQSTLP
12   NAYARGVVVV AAAGNSGSSG NNTIGYPAK YDSVIAVGAV DSNSNRASFS SVGAELEVMA PGAGVYSTYP
13   KAVSSGIVVA AAAGNEGSSG STSTVGYPAK YPSTIAVGAV NSANQRASFS SAGSELDVMA PGVSIQSTLP
14   KAVSSGIVVA AAAGNEGSSG SSSTVGYPAK YPSTIAVGAV NSSNQRASFS SAGSELDVMA PGVSIQSTLP
15   KAVSSGIVVA AAAGNEGSSG SSSTVGYPAK YPSTIAVGAV NSSNQRASFS SAGSELDVMA PGVSIQSTLP
16   KAVSSGIVVA AAAGNEGSSG STSTVGYPAK YPSTIAVGAV NSSNQRASFS SAGSELDVMA PGVSIQSTLP 211                                                                              276
3    NNSYASMPGT SMATPHVAGV AALVKQKNPS WNATQIRNHL KNTATNLGNS SQFGSGLVNA DAATR.
4    GSTYASLNGT SMATPHVAGA AALVKQKNPS WSNVQIRNHL KNTATSLGST NLYGSGLVNA EAATR.
5    GSTYASLNGT SMASPHVAGA AALVKQKNPS WSNVQIRNHL KNTATSLGST NLYGSGLVNA EAATR.
6    GSTYASLNGT SMATPHVAGA AALVKQKNPS WSNVQIRNHL KNTATSLGST NLYGSGLVNA EAATR.
7    GNRYASLSGT SMATPHVAGV AALVKQKNPS WSNTQIRQHL TSTATSLGNS NQFGSGLVNA EAATR.
8    GNGYASFNGT SMATPHVAGV AALVKQKNPS WSNVQIRNHL KNTATNLGNT TQFGSGLVNA EAATR.
9    NNGYRSLNGT SMASPHVAGV AALVKQKHPH LTAAQIRNRM NQTAIPLGNS TYYGNGLVDA EYAAQ.
10   GGTYGAYNGT SMATPHVAGT AALILSKHPT WTNAQVRDRL ESTATYLGNS FYYGKGLINV QAAAQ.
11   GNKYGAYNGT SMASPHVAGA AALILSKHPN WTNTQVRSSL ENTTTKLGDS FYYGKGLINV QAAAQ.
12   TSTYATLNGT SMASPHVAGA AALILSKHPN LSASQVRNRL SSTATYLGSS FYYGKGLINV EAAAQ.
13   GGTYGAYNGT SMATPHVAGA AALILSKHPT WTNAQVRDRL SSTATYLGSS ESTATYLGSS FYYGKGLINV QAAAQ.
14   GGTYGAYNGT SMATPHVAGA AALILSKHPT WTNAQVRDRL ESTATYLGNS FYYGKGLINV QAAAQ.
15   GGTYGAYNGT SMATPHVAGA AALILSKHPT WTNAQVRDRL ESTATYLGNS FYYGKGLINV QAAAQ.
16   GGTYGAYNGT SMATPHVAGA AALILSKHPT WTNAQVRDRL ESTATYLGNS FYYGKGLINV QAAAQ.
```

ALKALINE PROTEASE FROM *BACILLUS GIBSONII* (DSM 14391) AND WASHING AND CLEANING PRODUCTS COMPRISING SAID ALKALINE PROTEASE

CROSS-REFERENCE TO RELATED APPLICATIONS

This application is a continuation of International Application PCT/EP02/14125, filed Dec. 12, 2002, which claims benefit of German Application No. DE 101 62 727.0, filed Dec. 20, 2001, each of which are incorporated herein by reference in their entireties.

FIELD OF THE INVENTION

The present invention relates generally to the fields of molecular biology and protein chemistry. More particularly, the invention relates, for example, to alkaline proteases of the subtilisin type, as well as to products and methods employing these alkaline proteases.

BACKGROUND OF THE INVENTION

Proteases of the subtilisin type (subtilases, subtilopeptidases, EC 3.4.21.62), in particular subtilisins, are classed as belonging to the serine proteases, owing to the catalytically active amino acids. They are naturally produced and secreted by microorganisms, in particular by *Bacillus* species. They act as unspecific endopeptidases, i.e. they hydrolyze any acid amide bonds located inside peptides or proteins. Their pH optimum is usually within the distinctly alkaline range. A review of this family is provided, for example, by the paper "Subtilases: Subtilisin-like Proteases" by R. Siezen, pages 75-95 in "Subtilisin enzymes", edited by R. Bott and C. Betzel, New York, 1996. Subtilisins are suitable for a multiplicity of possible technical uses, as components of cosmetics and, in particular, as active ingredients of detergents or cleaning agents.

Enzymes are established active ingredients of washing and cleaning products. In this connection, proteases bring about the breakdown of proteinaceous soilings on the material to be cleaned such as, for example, textiles or hard surfaces. In favorable cases there are synergistic effects between the enzymes and the other constituents of the relevant products. This is described for example in U.S. Pat. No. 6,008,178. Owing to their favorable enzymic properties such as stability or pH optimum, subtilisins stand out among the washing and cleaning product proteases. The most important ones and the most important strategies for their technical development are stated below.

The development of washing product proteases is based on natural enzymes which are preferably produced by microbes. They are optimized by mutagenesis methods known per se, for example point mutagenesis, deletion, insertion or fusion with other proteins or protein portions or via other modifications for use in washing and cleaning products.

Thus, for example, according to application WO 93/07276, the protease 164-A1 which is obtainable from *Bacillus* spec. 164-A1 and is supplied by Chemgen Corp., Gaithersburg, Md., USA, and Vista Chemical Company, Austin, Tex., USA, is suitable for use in washing and cleaning products. Other examples are the alkaline protease from *Bacillus* sp. PD138, NCIMB 40338 of Novozymes (WO 93/18140), the proteinase K-16 derived from *Bacillus* sp. ferm. BP-3376 of Kao Corp., Tokyo, Japan, (U.S. Pat. No. 5,344,770) and, according to WO 96/25489 (Procter & Gamble, Cincinnati, Ohio, USA), the protease from the psychrophilic organism *Flavobacterium balustinum*. Further proteases of microbial origin which are suitable for use in washing and cleaning products are also known from the patent literature: for example from *Pseudomonas* (WO 00/05352), from *Metarrhizium* (EP 601005), from *Bacillus alkalophilus* DMS 6845 or DSM 5466 (DE 4411223) and various other microorganisms (WO 95/07350, EP 1029920, EP 578712, WO 01/00764, U.S. Pat. No. 6,197,740, WO 01/16285).

Subtilisin BPN' which is derived from *Bacillus amyloliquefaciens*, and *B. subtilis*, respectively, has been disclosed in the studies by Vasantha et al. (1984) in J. Bacteriol., Volume 159, pp. 811-819 and by J. A. Wells et al. (1983) in *Nucleic Acids Research*, Volume 11, pp. 7911-7925. Subtilisin BPN' serves as reference enzyme of the subtilisins, in particular with respect to numbering of positions. The application CA 2049097 discloses multiple mutants of this molecule, especially in relation to their stability in washing and cleaning products. Variants which are obtained by point mutations in the loop regions of this enzyme and which have reduced binding to the substrate with, at the same time, an increased rate of hydrolysis are presented for example in the patent applications WO 95/07991 and WO 95/30010. Washing products with such BPN' variants are disclosed for example in the patent application WO 95/29979.

The publications by E. L. Smith et al. (1968) in *J. Biol. Chem.*, Volume 243, pp. 2184-2191, and by Jacobs et al. (1985) in *Nucl. Acids Res.*, Volume 13, pp. 8913-8926 introduce the protease subtilisin Carlsberg. It is naturally produced by *Bacillus licheniformis* and was and, respectively, is obtainable under the trade name Maxatase® from Genencor International Inc., Rochester, N.Y., USA, and under the trade name Alcalase® from Novozymes A/S, Bagsvaerd, Denmark. Variants thereof which are obtainable by point mutations and have reduced binding to the substrate with a simultaneously increased rate of hydrolysis are disclosed, for example, by the application WO 96/28566 A2. These are variants in which single or multiple substitutions in the loop regions of the molecule have been carried out.

The protease PB92 is produced naturally by the alkaliphilic bacterium *Bacillus nov.* spec. 92 and was obtainable under the trade name Maxacal® from Gist-Brocades, Delft, The Netherlands. Its original sequence is described in patent application EP 283075 A2. Variants of said enzyme which have been obtained by point mutation and which are suitable for use in detergents and cleaning agents are disclosed in the applications WO 94/02618 and EP 328229, for example.

The subtilisins 147 and 309 are sold by Novozymes under the trade names ESPERASE® and SAVINASE®, respectively. They are originally derived from *Bacillus* strains disclosed by the application GB 1243784. Variants of said enzymes, which have been developed by means of point mutagenesis with respect to usage in washing and cleaning products, are disclosed, for example, in the applications WO 94/02618 (see above), WO 89/06279, WO 95/30011 and WO 99/27082. The application WO 89/06279 aimed at achieving higher oxidation stability, an increased rate of proteolysis and enhanced washing performance. It reveals that substitutions at particular positions alter the physical or chemical properties of subtilisin 147 or 309 molecules. The application WO 95/30011 introduces variants of subtilisin 309 which have point mutations in the loop regions of the molecule and thus exhibit reduced adsorption to the substrate with a simultaneously increased rate of hydrolysis. The application WO 99/27082 develops variants of, by way of example, subtilisin 309, whose washing performance is enhanced by enlarging the active loops by inserting at least one amino acid.

The *B. lentus* alkaline proteases are highly alkaline proteases from *Bacillus* species. The wild-type enzyme is derived from an alkaliphilic *bacillus* strain and itself shows comparatively high stability towards oxidation and the action of detergents. This strain was, according to the application WO 91/02792 (EP 493398 and U.S. Pat. No. 5,352,604), deposited under the number DSM 5483. According to the same application, the enzyme can be expressed heterologously in the host *Bacillus licheniformis*. Its three-dimensional structure is described in the publication of Goddette et al. (1992), *J. Mol. Biol.* Volume 228, pages 580-595: "The crystal structure of the *Bacillus lentus* alkaline protease, Subtilisin BL, at 1.4 Å resolution". Variants of this enzyme which can be obtained by point mutation and are suitable for use in washing and cleaning products are disclosed in WO 92/21760 (U.S. Pat. Nos. 5,340,735, 5,500,364 and 5,985,639) and WO 95/23221 (U.S. Pat. Nos. 5,691,295, 5,801,039 and 5,855,625). The strategy underlying WO 95/23221, namely deliberate alteration of the charge conditions near the substrate binding pocket is explained in U.S. Pat. No. 6,197,589. Further variants of this protease are described in the as yet unpublished applications DE 10121463 and DE 10153792.

Subtilisin DY has originally been described by Nedkov et al. 1985 in *Biol. Chem. Hoppe-Seyler*, Volume 366, pp. 421-430. According to the application WO 96/28557, for example, it may be optimized via specific point mutations in the active loops for usage in detergents and cleaning agents, producing variants having reduced adsorption and an increased rate of hydrolysis.

The enzyme thermitase which is to be assigned to the subtilases, but no longer to the subtilisins, (cf. R. Siezen, pages 75-95 in "Subtilisin enzymes", published by R. Bott and C. Betzel, New York, 1996) and is produced naturally by *Thermoactinomyces vulgaris* was originally described by Meloun et al. (*FEBS Lett.* 1983, pp. 195-200). The application WO 96/28558, for example, discloses variants having reduced adsorption and an increased rate of hydrolysis, owing to substitutions in the loop regions. However, thermitase is a molecule whose sequence overall deviates considerably from those of the other subtilisins.

Proteinase K is also a subtilase which has comparatively low homology, for example, to *B. lentus* alkaline protease. Proteinase K is originally from the microorganism *Tritirachium album* Limber and has been described by K. -D. Jany and B. Mayer 1985 in *Biol. Chem. Hoppe-Seyler*, Vol. 366, pp. 485-492. The application WO 96/28556 discloses numerous variants of proteinase K which are obtainable by point mutagenesis and have reduced adsorption to the substrate and an increased rate of hydrolysis.

WO 88/07581, finally, discloses the very similar proteases TW3 and TW7, inter alia for usage in washing and cleaning products.

The applications EP 199404, EP 251446, WO 91/06637 and WO 95/10591, for example, describe further proteases which are suitable for technical use, in particular in detergents and cleaning agents. The proteases of the application EP 199404 are various BPN' variants which are based on the patent EP 130756. EP 251446 discloses numerous BPN' variants, obtainable by exchanging individual amino acids. The proteases of the application WO 91/06637 are distinguished by point mutations of BPN' in positions 123 and/or 274. WO 95/10591 reveals variants, mainly of the *Bacillus lentus* protease, which have mutations in position 76 and also other positions.

Other known proteases are, for example, the enzymes obtainable under the trade names DURAZYM®, RELASE®, EVERLASE®, Nafizym, NATALASE®, KANNASE® and OVOZYMES® from Novozymes, under the trade names MAXAPEM®, PURAFECT®, PURAFECT OXP® and PROPERASE® from Genencor, under the trade name PROTOSOL® from Advanced Biochemicals Ltd., Thane, India and under the trade name WUXI® from Wuxi Snyder Bioproducts Ltd., China.

One strategy for enhancing the washing performance of subtilisins is to replace randomly or specifically individual amino acids by others in the known molecules, and to test the variants obtained for their washing performance contributions. This strategy is pursued by some of the further developments indicated in each case above, for example EP 130756. The allergenicity of the enzymes can also be improved for example according to WO 99/49056, WO 99/49057 and WO 01/07575 with certain amino acid exchanges or deletions.

In order to enhance the washing performance of subtilisins, numerous applications pursued the strategy of inserting additional amino acids into the active loops, thus, for example, apart from the already mentioned WO 99/27082, also the applications published with the numbers WO 00/37599, WO 00/37621 to WO 00/37627 and WO 00/71683 to WO 00/71691. Said strategy should accordingly be applicable in principle to all subtilisins belonging to either of the subgroups I-S1 (true subtilisins) or I-S2 (highly alkaline subtilisins).

Another strategy of enhancing the performance is to modify the surface charges and/or the isoelectric point of the molecules, thereby altering their interaction with the substrate. Variations of this kind are disclosed, for example, by U.S. Pat. No. 5,665,587 and the applications EP 405901, EP 945502 A1, WO 91/00334 and WO 91/00345. WO 92/11348 discloses point mutations for reducing the pH-dependent variation in the molecular charge. The application WO 00/24924 derives from this principle a method for identifying variants which are supposedly suitable for usage in washing and cleaning products; all variants disclosed here have at least one substitution at position 103, preference being given to multiple variants containing no substitution relevant to the present application. According to WO 96/34935, it is also possible to increase the hydrophobicity of the molecules for the purpose of enhancing the performance in washing and cleaning products, and this may influence the stability of the enzyme.

The application WO 99/20727 discloses subtilisin variants as are obtained by a method of the application WO 00/24924: they all comprise at least one substitution at position 103, combined with a multiplicity of other possible substitutions. The applications WO 99/20723 and WO 99/20726 disclose the same mutants for washing and cleaning products which additionally contain an amylase, or bleach.

Another method for modulating the efficiency of proteases is to form fusion proteins. Thus, for example, the applications WO 98/13483 and WO 00/01831 disclose fusion proteins composed of proteases and an inhibitor such as the *Streptomyces* subtilisin inhibitor. Another possibility is, for example according to WO 97/28243 or WO 99/57250, to couple to the cellulose binding domain (CBD), which is derived from cellulases, to increase the concentration of active enzyme in the direct vicinity of the substrate. According to WO 99/48918 the allergenicity or immunogenicity is reduced by coupling a peptide linker, and polymers thereon.

Variants with improved performance due to randomly generated amino acid exchanges and subsequent selection are revealed for example in WO 99/20769. A random method, based on the phage display system, for evolving proteases for use in washing and cleaning products is revealed for example in the application WO 97/09446.

A modern direction in enzyme development is to combine, via statistical methods, elements from known proteins related to one another to give novel enzymes having properties which have not been achieved previously. Methods of this kind are also listed under the generic term directed evolution and include, for example, the following methods: the StEP method (Zhao et al. (1998), *Nat. Biotechnol.*, Volume 16, pp. 258-261), random priming recombination (Shao et al., (1998), Nucleic Acids Res., Volume 26, pp. 681-683), DNA shuffling (Semmer, W. P. C. (1994), *Nature*, Volume 370, pp. 389-391) or recursive sequence recombination (RSR; WO 98/27230, WO 97/20078, WO 95/22625) or the RACHITT (Coco, W. M. et al. (2001), *Nat. Biotechnol.*, Volume 19, pp. 354-359). A survey of such methods is also provided by the prior article "Gerichtete Evolution und Biokatalyse" by Powell et al. (2001), *Angew. Chem.*, Vol. 113, pages 4068-4080.

Another, in particular complementary, strategy is to increase the stability of the proteases concerned and thus to increase their efficacy. For example, U.S. Pat. No. 5,230,891 has described stabilization via coupling to a polymer for proteases used in cosmetics; said stabilization is accompanied by enhanced skin compatibility. Especially for detergents and cleaning agents, on the other hand, stabilizations by point mutations are more familiar. Thus, according to U.S. Pat. Nos. 6,087,315 and 6,110,884, it is possible to stabilize proteases by replacing particular tyrosine residues with other residues. WO 89/09819 and WO 89/09830 describe relatively thermostable BPN' variants obtained by amino-acid substitution. Other possible examples of stabilization via point mutagenesis, which have been described, are:

replacing particular amino acid residues with proline according to WO 92/19729, and, respectively, EP 583339 and U.S. Pat. No. 5,858,757 and according to EP 516200;

introducing more polar or more highly charged groups on the molecule surface, according to EP 525610, EP 995801 and U.S. Pat. No. 5,453,372;

enhancing the binding of metal ions, in particular via mutagenesis of calcium binding sites, for example according to the teaching of the applications WO 88/08028 and WO 88/08033;

blocking autolysis by modification or mutagenesis, for example according to WO 98/20116 or U.S. Pat. No. 5,543,302.

Combination of a plurality of stabilization strategies as disclosed in the application EP 398539 A1.

According to U.S. Pat. Nos. 5,340,735, 5,500,364, 5,985,639 and 6,136,553, the positions relevant to stabilization can be found by analysis of the three-dimensional structure.

The documents EP 755999 and WO 98/30669, for example, disclose that proteases may be used together with a-amylases and other washing product enzymes in order to enhance the washing or cleaning performance. For example, EP 791046 discloses the possibility of combination with lipases. The application WO 95/10592 for example reveals that the variants previously described in WO 95/10591 for use in washing products are also suitable for use in bleaches. U.S. Pat. No. 6,121,226 for example discloses the simultaneous use of protease and soil release agents in washing products.

The application WO 97/07770 for example discloses that some proteases established for use in washing products are also suitable for cosmetic purposes. A further possible technical use of proteases is presented for example in the application EP 380362 A1. This relates to organic chemical syntheses, and the subtilisins said according to this application to be suitable for this are those stabilized by point mutagenesis.

The diverse technical areas of use presented here by way of example require proteases with different properties relating for example to the reaction conditions, the stability or the substrate specificity. Conversely, the possibilities of technical use of proteases, for example in the context of a washing or cleaning product formula, depend on further factors such as stability of the enzyme towards high temperatures, towards oxidizing agents, its denaturation by surfactants, on folding effects or on desired synergies with other ingredients.

Thus, there continues to be a great need for proteases which can be employed technically and which, owing to the large number of their areas of application, in their totality cover a wide range of properties, including very subtle differences in performance.

The basis for this is expanded by novel proteases which in turn are capable of further development targeted at specific areas of application.

SUMMARY OF THE INVENTION

In certain aspects, the present invention relates to a further, as yet unknown protease. It was intended that the wild-type enzyme preferably be distinguished in that on use in an appropriate product it at least comes close to the enzymes established for this purpose. Of particular interest in this connection was the contribution to the performance of a washing or cleaning product.

Additional aspects relate to nucleic acids coding for proteases of this kind and to vectors, host cells and preparation methods which may be utilized for obtaining proteases of this kind. Further aspects of the invention relate to corresponding products, in particular washing and cleaning products, corresponding washing and cleaning methods and also corresponding possible uses for proteases of this kind, as well as possible technical uses for the proteases found.

Other features and advantages of the present invention will be understood by reference to the detailed description and the examples that follow.

BRIEF DESCRIPTION OF THE DRAWINGS

FIG. 1 shows an alignment of the amino acid sequences of the protease of the invention from *Bacillus gibsonii* (DSM 143901) with the most similar and the most important known subtilisins which are compiled in table 2, in each case in the mature, i.e. processed, form.

Figure 2:
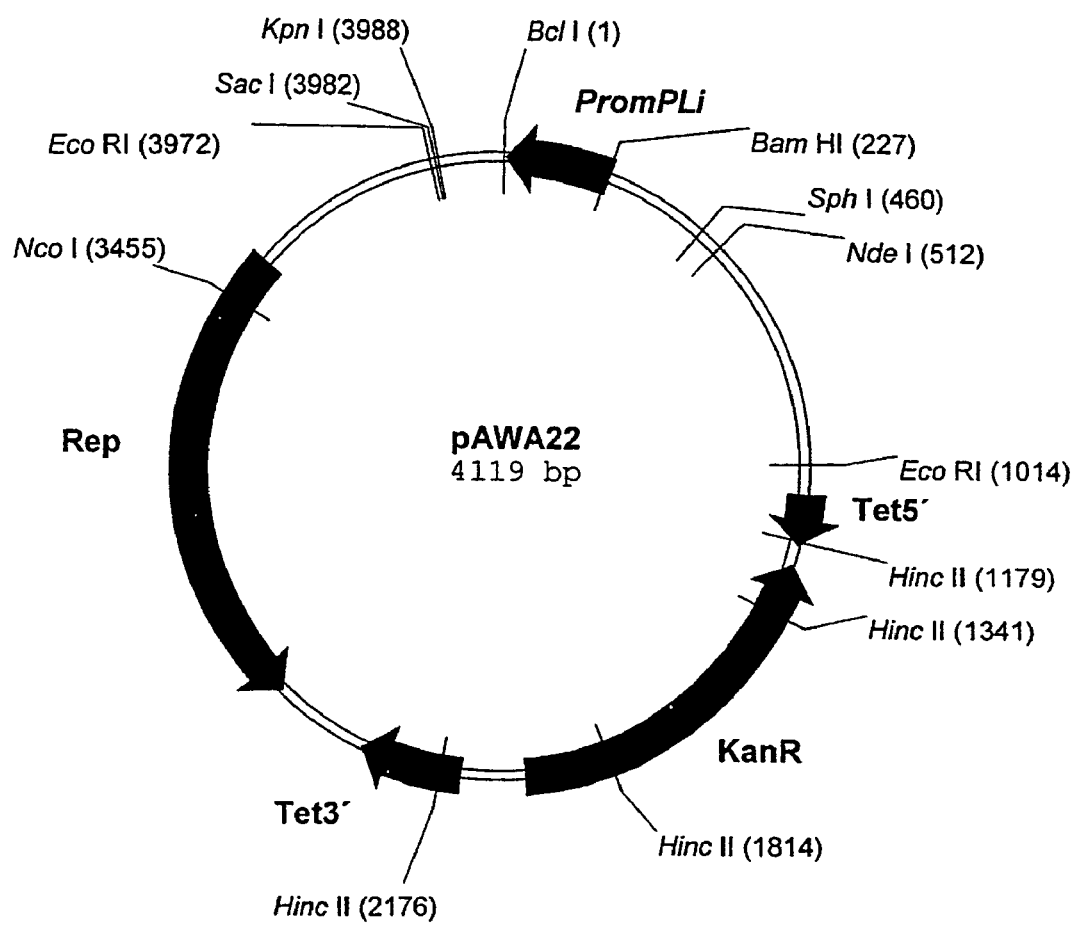

The following SEQ ID NOs (Column 1) correspond to the following proteases. In parentheses in each case is the ID of the database entry (compare also Table 2 in Example 2). The same SEQ ID NOs and the corresponding sequences are also shown in the Sequence Listing, which is appended herewith and which forms part of the present specification.

| SEQ ID NO: | | |
|---|---|---|
| 3 | Protease of the invention from *Bacillus gibsonii* (DSM 14391) | |
| 4 | Subtilisin P92 (ELYA_BACAO) | from *B. alkalophilus* |
| 5 | Savinase ® (SUBS_BACLE) | from *B. lentus* |
| 6 | Subtilisin BL (SUBB_BACLE) | from *B. lentus* |
| 7 | Subtilisin Sendai AprS (Q45522) | from *B.* sp. |

-continued

| SEQ ID NO: | | |
|---|---|---|
| 8 | Alkaline elastase (ELYA_BACSP) | from *B.* Ya-B |
| 9 | Subtilisin AprQ (Q45523) | from *B.* sp. |
| 10 | AprN (SUBN_BACNA) | from *B. subtilis* var. *natto* |
| 11 | Subtilisin Novo BPN' (SUBT_BACAM) | from *B. amyloliquefaciens* |
| 12 | Subtilisin Carlsberg (SUBT_BACLI) | from *B. licheniformis* |
| 13 | Subtilisin (SUBT_BACPU) | from *B. pumilus* |
| 14 | Subtilisin (SUBT_BACSA) | from *B. amylosacchariticus* |
| 15 | Subtilisin J (SUBT_BACST) | from *Geobacillus stearothermophilus* |
| 16 | Subtilisin E (SUBT_BACSU) | from *B. subtilis* |

FIG. 2 shows the expression vector pAWA22 which is derived from pBC16 and has a promoter from *B. licheniformis* (PromPLi) and, downstream thereof, a Bcl I restriction cleavage site (compare Example 2 and Bernhard et al. (1978), *J. Bacteriol.*, 133 (2), pp. 897-903).

DETAILED DESCRIPTION OF ILLUSTRATIVE EMBODIMENTS

According to one embodiment of the invention, alkaline proteases of the subtilisin type having amino acid sequences which are at least 80% identical to the amino acid sequence indicated in the sequence listing under SEQ ID NO:2 are provided.

Increasing preference is given in each case to those having an increasing extent of identity with the novel alkaline protease from *Bacillus gibsonii* (DSM 14391).

Further aspects of the invention comprise nucleic acids whose sequences are sufficiently similar to the nucleotide sequence indicated in SEQ ID No. 1 or code for proteases of the invention, and comprise appropriate vectors, cells or host cells and production methods. Also provided are corresponding products, in particular washing and cleaning products, corresponding washing and cleaning products and also corresponding possible uses for proteases of this kind. Finally, possible technical uses for the proteases found are defined.

A protein means in accordance with the present application a polymer which is composed of the natural amino acids, has a substantially linear structure and usually adopts a three dimensional structure to exert its function. The present application refers to the 19 proteinogenic, naturally occurring L-amino acids by the internationally used 1- and 3-letter codes. The combination of any of these names with a number indicates the amino acid residue which the particular protein carries at the respective position. Similar designations are established for point mutations. Unless stated otherwise, positions indicated refer to the in each case mature forms of the proteins concerned, i.e. without the signal peptides (see below).

An enzyme in accordance with the present application means a protein which exerts a particular biochemical function. Proteolytic enzymes or enzymes with proteolytic function, for example, mean generally those which hydrolyze the acid amide bonds of proteins, in particular those bonds located inside the proteins, and which may therefore also be referred to as endopeptidases. Subtilisin proteases are those endopeptidases which are naturally produced by Gram-positive bacteria and usually secreted or which are derived from the latter, for example via molecular-biological methods, and can be homologized with the natural subtilisin proteases via part regions such as structure-forming or function-carrying regions. They are assigned to the subtilases. These are described, for example, in the paper "Subtilases: Subtilisin-like Proteases" by R. Siezen, pages 75-95 in "Subtilisin enzymes", edited by R. Bott and C. Betzel, New York, 1996.

Numerous proteins are formed as "preproteins", i.e. together with a signal peptide. This then means the N-terminal part of the protein, whose function usually is to ensure the export of the protein produced from the producing cell into the periplasm or into the surrounding medium and/or the correct folding thereof. Subsequently, the signal peptide is removed from the remaining protein under natural conditions by a signal peptidase so that said protein exerts its actual catalytic activity without the initially present N-terminal amino acids.

Owing to their enzymic activity, preference is given for technical applications to the mature peptides, i.e. the enzymes processed after their preparation, over the preproteins.

Pro-proteins are inactive precursors of proteins. The precursors of the former containing a signal sequence are referred to as prepro-proteins.

Nucleic acids mean in accordance with the present application the molecules which are naturally composed of nucleotides, serve as information carriers and code for the linear amino acid sequence in proteins or enzymes. They may be present as single strand, as a single strand complementary to said single strand or as double strand. For molecular-biological work, preference is given to the nucleic acid DNA as the naturally more durable information carrier. In contrast, a RNA is produced to implement the invention in a natural environment such as, for example, in an expressing cell, and RNA molecules important to the invention are therefore likewise embodiments of the present invention. In turn, (c)DNA molecules can be derived from them for example by reverse transcription.

In accordance with the present application, the information unit of a nucleic acid, which corresponds to a protein, is also referred to as gene. In the case of DNA, the sequences of both complementary strands in each case all three possible reading frames must be taken into account. The fact that different codon triplets can code for the same amino acids so that a particular amino acid sequence can be derived from a plurality of different nucleotide sequences which possibly only have low identity must also be taken into account (degeneracy of the genetic code). Moreover, various organisms differ in the use of these codons. For these reasons, both amino acid sequences and nucleotide sequences must be incorporated into the scope of protection, and nucleotide sequences indicated are in each case regarded only as coding by way of example for a particular amino acid sequence.

It is possible for a skilled worker, via nowadays generally known methods such as, for example, chemical synthesis or polymerase chain reaction (PCR) in combination with molecular-biological and/or protein-chemical standard methods, to prepare complete genes on the basis of known DNA sequences and/or amino acid sequences. Methods of this kind are known, for example, from the "Lexikon der Biochemie" [encyclopedia of biochemistry], Spektrum Akademischer Verlag, Berlin, 1999, Volume 1, pp. 267-271 and Volume 2, pp. 227-229. This is possible, in particular, if a strain deposited with a strain collection can be used. For example, using PCR primers which can be synthesized on the basis of a known sequence, and/or via isolated mRNA molecules, it is possible to synthesize, clone and, if desired, further process, for example mutagenize, the genes in question from such strains.

Changes of the nucleotide sequence, such as those which may be produced, for example, by molecular-biological methods known per se, are referred to as mutations. Depending on the type of change, deletion, insertion or substitution mutations, for example, or those in which various genes or parts of genes are fused to one another (shuffling) are known; these are gene mutations. The corresponding organisms are referred to as mutants. The proteins derived from mutated nucleic acids are referred to as variants. Thus, for example, deletion, insertion, substitution mutations or fusions result in deletion-, insertion-, substitution-mutated or fusion genes and, at the protein level, in corresponding deletion, insertion or substitution variants, or fusion proteins.

Vectors mean in accordance with the present invention elements which consist of nucleic acids and which comprise a gene of interest as characteristic nucleic acid region. They are capable of establishing said gene as a stable genetic element replicating independently of the remaining genome in a species or a cell line over several generations or cell divisions. Vectors are, in particular when used in bacteria, special plasmids, i.e. circular genetic elements. Genetic engineering distinguishes between, on the one hand, those vectors which are used for storage and thus, to a certain extent, also for genetic engineering work, the "cloning vectors", and, on the other hand, those which perform the function of establishing the gene of interest in the host cell, i.e. enabling expression of the protein in question. These vectors are referred to as expression vectors.

Both bacterial cells and eukaryotic cells comprising said vectors are, irrespective of their differences, referred to generally as cells. Cells which comprise a vector, in particular an expression vector, and can thus be induced to express a transgene are referred to as host cells because they harbor the relevant genetic system.

Homologization is the comparison of a nucleic acid or amino acid sequence with that of known genes or proteins. It is undertaken for example via an alignment. The measure of the homology is a percentage of identity, as can be determined for example by the method indicated by D. J. Lipman and W. R. Pearson in *Science* 227 (1985), pages 1435-1441. This information may refer to the complete protein or to the region to be assigned in each case. A broader concept of homology, the similarity, also includes conserved variations, i.e. amino acids with similar chemical activity, in consideration because they usually carry out similar chemical activities within the protein. In the case of nucleic acids, only the percentage of identity is known.

It is possible by homologization to infer the functions of individual sequence regions, and the enzymatic activity of the complete enzyme under consideration, from the amino acid or nucleotide sequence. Homologous regions of different proteins are those having comparable functions which can be recognized by identity or conserved exchanges in the primary amino acid sequence. They include single amino acids, very small regions, called boxes, which are a few amino acids long, up to long regions in the primary amino acid sequence. Thus, the functions of the homologous regions are also to be understood to include very minor partial functions of the function carried out by the complete protein, such as, for example, the formation of individual hydrogen bonds or complexation of a substrate or transition complex. Other regions of the protein which are not involved in the actual enzymatic reaction may modify them qualitatively or quantitatively. This concerns, for example, enzyme stability, activity, reaction conditions or substrate specificity.

The term proteolytic enzyme or protease therefore means, in addition to the functions of the few amino acid residues of the catalytically active site, any functions as resulting from the action of the entire remaining protein or one or more parts of the remaining protein on the actually catalytically active regions. In accordance with the invention, such modifying functions or part activities alone are also regarded as proteolytic activity, as long as they support a proteolytic reaction. Such auxiliary functions or part activities include, for example, binding of a substrate, an intermediate or an end product, the activation or inhibition or mediation of a regulating influence on the hydrolytic activity. Another possible example is the formation of a structural element located far away from the active site. The second precondition for the fact that it is, according to the invention, a proteolytic protein, however, is that the chemical behavior of the actually active residues alone or, in addition, the action of the modifying parts results in a hydrolysis of peptide bonds. It is furthermore possible that one or more parts of, for example, the protein of the invention also modify qualitatively or quantitatively the activities of other proteases. This influencing of other factors is likewise regarded as proteolytic activity. Proteolytically active enzymes are also those proteases whose activity at a given point in time is blocked, for example by an inhibitor. Their principle suitability for the corresponding proteolytic reaction is crucial.

Fragments mean any proteins or peptides which are smaller than natural proteins or those which correspond to completely translated genes, and may also be obtained synthetically, for example. Owing to their amino acid sequences, they may be related to the corresponding complete proteins. They may adopt, for example, identical structures or exert proteolytic activities or part activities. Fragments and deletion variants of starting proteins are very similar in principle; while fragments represent rather relatively small pieces, the deletion mutants rather lack only short regions and thus only individual partial functions.

Chimeric or hybrid proteins mean in accordance with the present application those proteins which are composed of elements which naturally originate from different polypeptide chains from the same organism or from different organisms. This procedure is also called shuffling or fusion mutagenesis. The purpose of such a fusion is, for example, to cause or to modify an enzymic function with the aid of the fused-to protein part of the invention.

Proteins obtained by insertion mutation mean those variants which have been obtained via methods known per se by inserting a nucleic acid fragment or protein fragment into the starting sequences. They should be classified as chimeric proteins, due to their similarity in principle. They differ from the latter merely in the size ratio of the unaltered protein part to the size of the entire protein. The proportion of foreign protein in such insertion-mutated proteins is lower than in chimeric proteins.

Inversion mutagenesis, i.e. a partial sequence conversion, may be regarded as a special form of both deletion and insertion. The same applies to a regrouping of various molecule parts, which deviates from the original amino acid sequence. Said regrouping can be regarded as deletion variant, as insertion variant and also as shuffling variant of the original protein.

Derivatives mean in accordance with the present application those proteins whose pure amino acid chain has been chemically modified. Those derivatizations may be carried out, for example, biologically in connection with protein biosynthesis by the host organism. Molecular-biological methods may be employed here, for example, such as the cotransformation with genes which ensure the relevant modification. However, derivatizations may also be carried out chemically, for example by chemical conversion of an amino acid side chain or by covalent binding of another compound to the protein. Such a compound may also be, for example, other proteins which are bound, for example, via bifunctional chemical compounds to proteins of the invention. Modifications of this kind influence, for example, substrate specificity or strength of binding to the substrate or cause transient blocking of the enzymatic activity if the coupled-to substance is an inhibitor. This is useful for the period of storage, for example. Likewise, derivatization means covalent binding to a macromolecular support.

In accordance with the present invention, all enzymes, proteins, fragments, fusion proteins and derivatives, unless they need to be explicitly referred to as such, are included under the generic term proteins.

The performance of an enzyme means its efficacy in the technical area considered in each case, preferably within the scope of a correspondingly directed product. Said performance is based on the actual enzymic activity but, in addition, depends on further factors relevant to the particular process. These include, for example, stability, substrate binding, interaction with the material supporting the substrate or interactions with other ingredients, in particular synergies.

The washing or cleaning performance of a washing or cleaning product means in accordance with the present application the effect exerted by the product studied on the soiled articles, for example textiles or objects with hard surfaces. Individual components of such products, for example individual enzymes, are evaluated with respect to their contribution to the washing or cleaning performance of the entire washing or cleaning product, for it is not readily possible to deduce the contribution of an enzyme to the washing performance of a product from the enzymic properties of said enzyme. Examples of other factors which play a part here are stability, substrate binding, binding to the material to be cleaned and interactions with other ingredients of the said washing or cleaning products, in particular synergies in removing the soils.

The naturally produced alkaline protease of the subtilisin type on which the present invention is based is, as can be ascertained from the examples, obtainable from the culture supernatant of the strain *Bacillus gibsonii* (DSM 14391).

This strain was deposited in accordance with the Budapest Treaty on the International Recognition of the Deposit of Microorganisms of Apr. 28, 1997 at the Deutsche Sammlung von Mikroorganismen und Zellkulturen GmbH, Mascheroder Weg 1b, 38124 Brunswick on Mar. 1, 2001. Its designation there is ID 01-192 and the accession number is DSM 14391. The standard information on the features of this biological material, as determined on deposition by the DSMZ on Apr. 19, 2001, is compiled in table 1 (example 1).

The present patent application followed the strategy of finding in a natural habitat a protease-producing microorganism and thus a naturally produced enzyme which satisfies as completely as possible the stated requirements.

It was possible to find such an enzyme, as described in the examples of the present application, in the form of the alkaline protease from *Bacillus gibsonii* (DSM 14391).

As can be established, going beyond the biochemical characterization undertaken by the Deutsche Sammlung von Mikroorganismen und Zellkulturen GmbH and indicated in table 1 of example 1, this strain secretes a proteolytic activity. This has been investigated in accordance with the exemplary embodiments of the present application and can be described as follows: it is, according to SDS polyacrylamide gel electrophoresis, a 26 kD protein having an isoelectric point of 11 as determined by isoelectric focusing. The specific activity for the substrate AAPF is 21 U/mg. The pH optimum, determined at 50° C., is pH 11.

The nucleotide sequence of the novel alkaline protease from *Bacillus gibsonii* (DSM 14391) according to the invention is indicated in the sequence listing of the present application under SEQ ID No. 1. It comprises 1152 bp. The amino acid sequence derived therefrom is indicated in SEQ ID No. 2. It comprises 383 amino acids, followed by a stop codon. The first 114 amino acids thereof are probably not present in the mature protein, so that the envisaged length of the mature protein is 269 amino acids.

As described in example 2, these sequences were compared with the protease sequences obtainable from generally accessible databases Swiss-Prot (Geneva Bioinformatics (GeneBio) S.A., Geneva, Switzerland and GenBank (National Center for Biotechnology Information NCBI, National Institutes of Health, Bethesda, Md., USA).

By this means, at the DNA level, the following three genes were identified as the most similar for the complete gene: (1.) the alkaline elastase from *Bacillus* Ya-B (ID ELYA_BACSP) with 66% identity, (2.) the subtilisin *Sendai* from *Bacillus Sendai* (ID Q45522) with 65% identity and (3.) the subtilisin P92 from *Bacillus alkalophilus* (ID ELYA_BACAO) with 62% identity.

At the amino acid level, those identified as most similar for the complete preproprotein were: (1.) the alkaline elastase from *Bacillus* Ya-B (ID ELYA_BACSP) equal to the subtilisin P92 from *Bacillus alkalophilus* (ID ELYA_BACAO) with 66% identity, (2.) the subtilisin *Sendai* from *Bacillus Sendai* (ID Q45522) with 64% identity and (3.) the subtilisin AprQ from *Bacillus* sp. (ID Q45523) with 50% identity.

At the amino acid level, those identified as most similar for the mature protein were: (1.) the two subtilisins, subtilisin P92 from *Bacillus alkalophilus* (I) ELYA_BACAO) and subtilisin 309 (Savinase®) from *Bacillus lentus* (ID SUBS_BACLE) with 78% identity, (2.) the two subtilisins, *B. lentus* alkaline protease from *Bacillus lentus* DSM 5483 (ID SUBB_BACLE) and subtilisin *Sendai* from *Bacillus Sendai* (ID Q45522) with 77% identity and (3.) the alkaline elastase from *Bacillus* Ya-B (ID ELYA_BACSP) with 76% identity.

Further similar enzymes are listed in table 2 in example 2 and are compared in the alignment in FIG. 1 in respect of the amino acid sequences of the mature proteins with the alkaline protease of the invention from *Bacillus gibsonii* (DSM 14391).

On the basis of the agreements to be identified and of the relationship with other indicated subtilisins, this alkaline protease is to be regarded as a subtilisin.

One subject matter of the present invention is thus every alkaline protease of the subtilisin type having an amino acid sequence at least 70% identical to the amino acid sequence indicated in SEQ ID No. 2.

Among these, increasingly preferred are those whose amino acid sequence is at least in each case 72%, 74%, 76%, 78%, 80%, 82%, 84%, 85%, 86%, 88%, 90%, 91%, 92%, 93%, 94%, 95%, 96%, 97%, 98%, 99% and 100% identical to the amino acid sequence indicated in SEQ ID No. 2.

This is because it is to be expected that the properties thereof are increasingly similar to those of the alkaline protease from *B. gibsonii* (DSM 14391).

As already mentioned, on the basis of a comparison of the N-terminal sequences the amino acids 1 to 114 are presumably to be regarded as leader peptide, and the mature protein is envisaged to extend from positions 115 to 384 according to SEQ ID No. 2. Position 384 is accordingly occupied by a stop codon and thus actually does not correspond to an amino acid. However, since the information about the end of a coding region can be regarded as important component of an amino acid sequence, this position is included according to the invention in the region corresponding to the mature protein.

One embodiment of this aspect of the invention is thus every alkaline protease of the subtilisin type having an amino acid sequence which is at least 80% identical in positions 115 to 384 to the amino acid sequence indicated in SEQ ID No. 2.

Among these, increasingly preferred are those whose amino acid sequence is at least in each case 82%, 84%, 86%, 88%, 90%, 91%, 92%, 93%, 94%, 95%, 96%, 97%, 98%, 99% and 100% identical in positions 115 to 384 to the amino acid sequence indicated in SEQ ID No. 2.

Should it emerge, for example through a N-terminal sequencing of the proteolytic protein released in vivo by *Bacillus gibsonii* (DSM 14391), that the cleavage site is located not between the 114th and the 115th amino acid according to SEQ ID No. 2, but elsewhere, in this case these statements relate to the actual mature protein.

One embodiment of this aspect of the invention is every alkaline protease of the subtilisin type which is derived from a nucleotide sequence which is at least 70% identical to the nucleotide sequence indicated in SEQ ID No. 1, in particular over the part region corresponding to positions 115 to 384 in SEQ ID No. 2.

Among these, increasingly preferred are those derived from a nucleotide sequence which is at least in each case 72%, 74%, 76%, 78%, 80%, 82%, 84%, 85%, 86%, 88%, 90%, 91%, 92%, 93%, 94%, 95%, 96%, 97%, 98%, 99% and 100% identical to the nucleotide sequence indicated in SEQ ID No. 1, in particular over the part region corresponding to positions 115 to 384 according to SEQ ID No. 2.

This is because it is to be expected that these nucleic acids code for proteins whose properties are increasingly similar to those of the alkaline protease from *B. gibsonii* (DSM 14391), in particular the mature protein. In this case too, as for all following embodiments, it is again true that these statements relate to the actual mature protein should it emerge that the cleavage site of the protein is located elsewhere than indicated above.

The most preferred embodiment of this aspect of the invention is every alkaline protease of the subtilisin type whose amino acid sequence is identical to the amino acid sequence indicated in SEQ ID No. 2 overall, preferably in positions 115 to 384, and/or whose amino acid sequence is identical to an amino acid sequence derived from the nucleotide sequence indicated in SEQ ID No. 1 in total, preferably in positions 343 to 1152.

This is because such a one constitutes the newly found alkaline protease from *Bacillus gibsonii* DSM 14391) which is made available with the present application.

This protease is as yet unknown in the prior art. It can be isolated, produced and employed as indicated in the examples. It is additionally distinguished, as likewise documented in the examples, on use in an appropriate product by approaching or even in some cases exceeding the performance of the enzymes established for this purpose.

It can, as an enzyme naturally produced microbially, serve as starting point for the development of industrial proteases which can be employed in particular in washing products, in order to be optimized for the desired use by mutagenesis methods known per se, for example point mutagenesis, fragmentation, deletion, insertion or fusion with other proteins or protein portions or by other modifications. Such optimizations may be, for example, adaptations to the effects of temperature, pH variations, redox conditions and/or other influences which are relevant to the technical areas of use. Examples of desiderata are an improvement in the resistance to oxidation, in the stability towards denaturing agents or proteolytic degradation, towards high temperatures, acidic or strongly alkaline conditions, a change in the sensitivity towards calcium ions or other cofactors, and a reduction in the immunogenicity or allergenic effect.

It is possible for this purpose to alter for example, applying the teaching of WO 00/36069, by targeted point mutations the surface charges or the loops involved in catalysis or substrate binding. The latter is disclosed for example in WO 95/30011, WO 99/27082, WO 00/37599, WO 00/37621 to WO 00/37627 and WO 00/71683 to WO 00/71691. Further modifications to be introduced in particular by genetic engineering methods can be carried out for example applying the teachings of the applications WO 92/21760 and WO 95/23221. A starting point for this is the alignment depicted in FIG. 1 of the present application. This makes it possible for positions of interest, which are described in said applications, for the protease from *Bacillus gibsonii* (DSM 14391) to be inferred from the known enzymes and to be varied appropriately by methods known per se.

The mutagenesis methods are based on the relevant nucleotide sequence which is indicated in SEQ ID No. 1, or nucleotide sequences which are sufficiently similar thereto and which are described hereinbelow as a separate subject matter of the present invention. Appropriate molecular biology methods are described in the prior art, for example in manuals such as that of Fritsch, Sambrook and Maniatis "Molecular cloning: a laboratory manual", Cold Spring Harbour Laboratory Press, New York, 1989.

Further embodiments of the present invention are all proteins or fragments derived from an alkaline protease of the invention, described above, of the subtilisin type by fragmentation or deletion mutagenesis and having increasingly preferably at least 20, 22, 24, 26, 28, 30, 32, 34, 36, 38, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 343 and 360 amino acids which are already connected in the starting molecule and are located at the start, internally or at the end of the starting amino acid sequence.

The alignment in FIG. 1 reveals in the region from position 167 to 184 (according to the numbering of the alignment) a fragment with a length of 18 amino acids which is identical to the most similar enzyme. Proteins or fragments of the invention which are derived by fragmentation or deletion mutagenesis accordingly have relatively large regions which are not identical to known proteases.

These are preferably those which correspond to the region of amino acids 112 to 381 according to SEQ ID No. 2, that is to say the mature protein.

These are increasingly preferably in each case proteins or fragments derived by fragmentation or deletion mutagenesis which are at least in each case 82%, 84%, 86%, 88%, 90%, 91%, 92%, 93%, 94%, 95%, 96%, 97%, 98%, 99% and 100% identical to the homologous sequences indicated in SEQ ID No. 2.

Fragments of the invention mean all proteins or peptides which are smaller than the homologous proteins which correspond to those of SEQ ID No. 1 or SEQ ID No. 2 but conform with them in the appropriate partial sequences. These fragments may be for example single domains or segments which do not conform with the domains. Such fragments may be producible at lower cost, no longer have certain possibly disadvantageous characteristics of the starting molecule such as, possibly, an activity-lowering regulatory mechanism, or display a more favorable profile of activity. Such protein fragments can also be produced non-biosynthetically but, for example, chemically. Chemical synthesis is advantageous for example when chemical modifications are to be undertaken following the synthesis.

Proteins obtainable by deletion mutation are also to be assigned to the fragments because they are analogous in principle. Deletion mutagenesis is particularly worthwhile for deleting inhibiting regions. The result of deletions may be associated both with a specialization and with an extension of the range of application of the protein.

Proteins obtainable from preproteins by elimination of the N-terminal amino acids, and signal peptides can also be regarded as naturally formed fragments or deletion-mutated proteins. Such a cleavage mechanism can be used for example to specify, with the aid of particular sequence regions which are recognized by signal peptidases, specific cleavage sites in recombinant proteins. It is thus possible to carry out in vitro activation and/or deactivation of proteins of the invention.

Further embodiments of the present invention are all proteins derived from an alkaline protease of the invention, described above, of the subtilisin type or a corresponding fragment by insertion mutagenesis, by substitution mutagenesis and/or by fusion with at least one other protein or protein fragment.

Chimeric proteins of the invention display proteolytic activity in the widest sense. This may be exercised or modified by a molecule part derived from a protein of the invention. The chimeric proteins may thus also be located over their entire length outside the region claimed above. The point of such a fusion is, for example, to introduce or to modify a particular function or part function with the aid of the fused-on protein part of the invention. It is in this connection immaterial for the purposes of the present invention whether such a chimeric protein consists of a single polypeptide chain or a plurality of subunits. To implement the last-mentioned alternative it is possible, for example, to break down a single chimeric polypeptide chain into a plurality thereof by a specific proteolytic cleavage post-translationally or only after a purification step.

Thus, for example, it is possible, based on WO 99/57254, to provide a protein of the invention or parts thereof via peptide linkers or directly as fusion protein with binding domains from other proteins, for example the cellulose binding domain, and thus to make hydrolysis of the substrate more efficient. Such a binding domain might also originate from a protease, for example in order to enhance the binding of the protein of the invention to a protease substrate. This increases the local protease concentration, which may be advantageous in individual applications, for example in the treatment of raw materials. It is likewise possible for proteins of the invention also to be linked for example to amylases or cellulases in order to exercise a dual function.

The proteins of the invention which are obtainable by insertion mutation are, because they are analogous in principle, to be assigned to the chimeric proteins of the invention. These also include substitution variants, that is to say those in which individual regions of the molecule have been replaced by elements from other proteins.

The point of insertion and substitution mutagenesis is, as in the case of hybrid formation, to combine individual properties, functions or part functions of proteins of the invention with those of other proteins. This also includes for example variants to be obtained by shuffling or recombination of partial sequences from different proteases. It is possible in this way to obtain proteins which have not previously been described. Such techniques permit effects ranging from drastic to very subtle modulations of activity.

Such mutations are preferably carried out by a random method to be assigned to the area of directed evolution, such as, for example, by the STEP method (Zhao et al. (1998), Nat. Biotechnol., Volume 16, pp. 258-261), the random priming recombination (Shao et al. (1998), Nucleic Acids Res., Volume 26, pp. 681-683), the DNA shuffling (Stemmer, W. P. C. (1994), Nature, Volume 370, pp. 389-391) or recursive sequence recombination (RSR; WO 98/27230, WO 97/20078, WO 95/22625) or the RACHITT method (Coco, W. M. et al. (2001), Nat. Biotechnol., Volume 19, pp. 354-359). Methods of these types are expediently coupled to a selection or screening method following the mutagenesis and expression, in order to identify variants having the desired properties. Since these techniques apply at the DNA level, the newly produced genes relevant in each case provide the starting point for biotechnological production.

Inversion mutagenesis, i.e. a partial sequence reversal, can be regarded as a special form both of deletion and of insertion. Variants of this type can likewise be produced in targeted fashion or randomly.

Preference is given to all proteins, protein fragments or fusion proteins mentioned to date which are characterized in that they are able per se to hydrolyze protein.

Such entities are categorized according to the official Enzyme Nomenclature 1992 of the IUBMB under 3.4 (peptidases). Among these, preference is given to endopeptidases, particularly of the groups 3.4.21 serine proteinases, 3.4.22 cysteine proteinases, 3.4.23 aspartate proteinases and 3.4.24 metallo proteinases. Of these, serine proteinases (3.4.21) are particularly preferred, and among these subtilases and, among these, very particularly subtilisins (compare "Subtilases: Subtilisin-like proteases" by R. Siezen, pages 75-95 in "Subtilisin enzymes", edited by R. Bott and C. Betzel, New York, 1996). Among these in turn, preference is given to subtilisins of group IS-2, the highly alkaline subtilisins.

In this connection, active molecules are preferred to inactive ones, because in particular the proteolysis which is performed is important for example in the areas of use detailed below.

The fragments mentioned above also have a proteolytic activity in the widest sense, for example for complexation of a substrate or for formation of a structural element necessary for the hydrolysis. They are preferred when they can themselves be employed for the hydrolysis of another protein without the need for further protease components to be present. This relates to the activity which can be performed by a protease per se; the presence, which may be necessary at the same time, of buffer substances, cofactors, etc. remains unaffected by this.

An interplay of different parts of the molecule for the hydrolysis of proteins naturally exists more in deletion mutants than in fragments and emerges especially in fusion proteins, very particularly those derived from shuffling of related proteins. Where this results in maintenance, modification, specification or else first attainment of a proteolytic function in the widest sense, the deletion variants and the fusion proteins are proteins of the invention. Preferred representatives of this aspect of the invention among these are those able per se to hydrolyze a protein substrate without the need for further protease components to be present.

A preferred embodiment is represented by all proteins, protein fragments or fusion proteins mentioned to date which are characterized in that they are additionally derivatized.

Derivatives mean those proteins which are derived from the mentioned proteins by an additional modification. Such modifications may affect, for example, the stability, substrate specificity or the binding strength to the substrate or the enzymatic activity. They can also be used to reduce the allergenicity and/or immunogenicity of the protein and thus to increase for example its compatibility with skin.

Such derivatizations can for example take place biologically, for example in connection with the protein biosynthesis by the producing host organism. Couplings of lower molecular weight compounds such as lipids or oligosaccharides should be particularly emphasized in this connection.

Derivatizations may, however, also be carried out chemically, for example by chemical transformation of a side chain or by covalent bonding of another, for example macromolecular compound to the protein. A chemical modification is described for example in the application DE 4013142. The coupling of amines to carboxyl groups of an enzyme to alter the isoelectric point for example is disclosed in WO 95/26398. It is possible for example to link macromolecules such as proteins, for example via bifunctional chemical compounds, to proteins of the invention. Thus, for example, it is possible by applying the teaching of WO 99/57154 to WO 99/57159, WO 00/18865 and WO 00/57155 to provide a protein of the invention via a linker with a specific binding domain. Such derivatives are particularly suitable for use in washing or cleaning products. It is also possible in analogy to WO 00/01831 to link protease inhibitors to the proteins of the invention via linkers, in particular amino acid linkers. Couplings with other macromolecular compounds such as, for example, polyethylene glycol improve the molecule in relation to further properties such as stability or compatibility with skin. Such a modification is described for example in U.S. Pat. No. 5,230,891 for proteases for use in cosmetics.

Derivatives of proteins of the invention may also mean preparations of these enzymes in the widest sense. Depending on the isolation, processing or preparation, a protein may be associated with various other substances, for example from the culture of the producing microorganisms. A protein may also have been mixed deliberately with certain other substances, for example to increase its storage stability. The invention therefore also relates to all preparations of a protein of the invention. This is also independent of whether this enzymatic activity is in fact displayed in a particular preparation or not. This is because it may be desired for it to have only little, or no, activity during storage and to display its proteolytic function only at the time of use. This can be controlled for example via appropriate accompanying substances. Joint preparation of proteases with protease inhibitors in particular is known in the prior art (WO 00/01826).

A preferred embodiment is represented by all proteins, protein fragments or fusion proteins mentioned to date which are characterized in that they are additionally stabilized.

This increases their stability during storage and/or during use, for example during the washing process, so that their activity persists longer and is thus enhanced. The stability of proteases of the invention may be increased by coupling to polymers, for example. A method of this kind is described in U.S. Pat. No. 5,230,891, for example. It requires linking the proteins, prior to their use in appropriate agents, via a chemical coupling step to such polymers.

Preference is given to stabilizations possible via point mutagenesis of the molecule itself, since they do not require any further working steps following obtainment of the protein. Some point mutations suitable for this are known per se from the prior art. Thus, according to U.S. Pat. No. 6,087,315 and U.S. Pat. No. 6,110,884, proteases may be stabilized by replacing particular tyrosine residues with other residues.

Other possibilities are, for example:
replacing particular amino acid residues with proline, according to EP 583339;
introducing more polar or more highly charged groups on the surface of the molecule, according to EP 995801;
altering the binding of metal ions, in particular the calcium binding sites, for example according to the teaching of the applications WO 88/08028 and WO 88/08033.

According to the first of these documents, one or more of the amino acid residues involved in calcium binding would have to be replaced with negatively charged amino acids; according to the teaching of the application WO 88/08033, point mutations would have to be introduced simultaneously in at least one of the sequences of the two residues arginine/glycine for stabilization via calcium binding;
according to U.S. Pat. No. 5,453,372, proteins may be protected by particular mutations on the surface against the effect of denaturating agents such as surfactants.

Further comparable possibilities are indicated in U.S. Pat. Nos. 5,340,735, 5,500,364, 5,985,639 and 6,136,553.

Another possibility for stabilization towards elevated temperature and the effect of surfactants would be, applying the teaching of WO 92/21760 and the as yet unpublished applications DE 10121463 and DE 10153792, stabilization by exchange of amino acids located near the N terminus for those which make contact, via non-covalent interactions, with the remainder of the molecule and thus make a contribution to maintaining the globular structure.

Preferred embodiments are those in which the molecule is stabilized in a plurality of ways. This is because, for example according to WO 89/09819, an additive effect can be assumed with a plurality of stabilizing mutations.

A preferred embodiment is represented by all proteins, protein fragments, fusion proteins or derivatives which are characterized in that they have at least one antigenic determinant in common with one of the proteins, protein fragments, fusion proteins or derivatives of the invention which are described above.

This is because the secondary structural elements of a protein and its three-dimensional folding are crucial for the enzymatic activity. Thus, domains which differ distinctly from one another in their primary structure may form structures which are substantially spatially coincident and thus make identical enzymatic behavior possible. Such common features in the secondary structure are normally recognized as conforming antigenic determinants by antisera or pure or monoclonal antibodies. Proteins or derivatives which are similar to one another can thus be detected and assigned by immunochemical cross-reactions. For this reason, proteins which possibly cannot from their levels of homology in the primary structure, but can from their immunochemical relationship, be assigned to the proteins, protein fragments, fusion proteins or derivatives of the invention which are defined above are also in particular included in the scope of protection of the present invention.

A preferred embodiment is represented by all the proteins, protein fragments, fusion proteins or derivatives mentioned to date which are characterized in that they are obtainable from a natural source, in particular from a microorganism.

These may be, for example, unicellular fungi or bacteria. This is because they can usually be isolated and handled more easily than multicellular organisms or the cell cultures derived from multicellular organisms; although the latter may represent worthwhile options for specific embodiments and are thus not in principle excluded from the subject matter of the invention.

It is possible that although naturally occurring producers are able to produce an enzyme of the invention, the latter is expressed and/or released into the surrounding medium to only a small extent under the conditions initially established. However, this does not preclude the possibility of stimulating them to economically worthwhile production of the protein of the invention under the influence of suitable environmental conditions or other factors which can be established experimentally. Such a regulatory mechanism can be employed deliberately for biotechnological production. If the latter is also impossible, they can still be used to isolate the relevant gene.

Among these, those from gram-positive bacteria are particularly preferred.

This is because they have no outer membrane and thus release secreted proteins directly into the surrounding medium.

Those from gram-positive bacteria of the genus *bacillus* are very particularly preferred.

*Bacillus* proteases have from the outset favorable properties for various possible technical uses. These include a certain stability to increased temperature, oxidizing or denaturing agents. Moreover, most experience has been obtained with microbial proteases with respect to their biotechnological production, concerning, for example, the construction of suitable cloning vectors, the selection of host cells and growth conditions or the evaluation of risks such as allergenicity, for example. *Bacilli* are moreover established as producer organisms with particularly high production efficiency in industrial processes. The amount of knowledge obtained for preparation and use of these proteases benefits, in addition, further inventive developments of these enzymes, relating, for example, to their compatibility with other chemical compounds such as ingredients of washing or cleaning products, for example.

Among those from the *bacillus* species, in turn, preference is given to those from the species *Bacillus gibsonii*, in particular from the strain *Bacillus gibsonii*. (DSM 14391).

This is because the embodiment of the enzyme of the invention was originally obtained therefrom. Its relevant sequences are indicated in the sequence listing, and its enzymatic characteristics are described in the examples. It is possible to prepare from this or from related strains the variants described above in particular by applying molecular-biological standard methods such as, for example, PCR and/or point mutagenesis methods known per se.

A further achievement of the object, and thus an inherent aspect of the invention is represented by the nucleic acids which serve to implement the invention.

Nucleic acids are the starting point for virtually all molecular-biological studies and developments of proteins and production thereof, including, in particular, sequencing of genes and derivation of the corresponding amino acid sequence, any kind of mutagenesis (see above) and expression of the proteins.

Mutagenesis for developing proteins having particular properties is also referred to as "protein engineering". Examples of properties to be optimized have been mentioned hereinbefore. Such a mutagenesis can be carried out in targeted fashion or by random methods, for example with a subsequent identification and/or selection method directed at the activity (screening and selection) on the cloned genes, for example by hybridization with nucleic acid probes, or on the gene products, the proteins, for example via their activity.

Further development of the proteases of the invention may also be oriented in particular on the ideas presented in the publication "Protein engineering" by P. N. Bryan (2000) in *Biochim. Biophys. Acta.*, Volume 1543, pages 203-222.

One subject matter of the present invention is thus every nucleic acid coding for an alkaline protease of the subtilisin type, whose nucleotide sequence is at least 70% identical, especially over the part region corresponding to amino acids 115 to 384 according to SEQ ID NO. 2.

Among these, increasingly preferred are those whose nucleotide sequence is at least in each case 72%, 74%, 76%, 78%, 80%, 82%, 84%, 85%, 86%, 88%, 90%, 91%, 92%, 93%, 94%, 95%, 96%, 97%, 98%, 99% and 100% identical, in particular over the part region corresponding to amino acids 115 to 384 according to SEQ ID NO.2. What has been stated above applies correspondingly to the positions of the mature protein and the stop codon.

This is because it is to be expected that these nucleic acids code for proteins whose properties are increasingly similar to those of the alkaline protease from *B. gibsonii* (DSM 14391).

Further representatives of this aspect of the invention are all nucleic acids which code for one of the proteins, protein fragments, fusion proteins or derivatives of the invention which are described above.

The nucleic acids which code for the preferred forms mentioned above are correspondingly preferred, especially also the nucleic acids obtained by mutagenesis.

In particular, the nucleic acids which code for protein fragments are expressly included in the scope of protection of the present invention. With such oligonucleotides, all three reading frames, both in the sense and in the antisense orientation, must be taken into account. This is because they can be used, in particular via the polymerase chain reaction (PCR), as starting points for the synthesis of related nucleic acids, for example for the amplification of related genes from natural organisms. They may also be used to produce chimeras by a PCR-based shuffling method. Other shuffling methods such as, for example, the recombining ligation reaction (RLR) disclosed in the application WO 00/09679 are also based on oligonucleotides which correspond to randomly or specifically selected protein fragments. Antisense oligonucleotides may also be employed for example for regulating expression.

In accordance with the statements made above, among the nucleic acids of the invention which have been described above the following are increasingly preferred:

those characterized in that they are obtainable from a natural source, in particular from a microorganism;

among these, those which are characterized in that the microorganism is a gram-positive bacterium;

among these, those which are characterized in that the gram-positive bacterium is one of the genus *bacillus*; and among these, those which are characterized in that the *bacillus* species is *Bacillus gibsonii*, in particular *Bacillus gibsonii* (DSM 14391).

Vectors comprising one of the nucleic acid regions of the invention defined above, in particular one which codes for one of the proteins, protein fragments, fusion proteins or derivatives of the invention which are defined above, form an inherent aspect of the invention.

In order to handle the nucleic acids relevant to the invention, and thus, in particular, to prepare for production of proteins of the invention, they are conveniently ligated into vectors. Such vectors and the relevant methods of working are described in detail in the prior art. Vectors are commercially available in large number and range of variation, both for cloning and for expression. These include, for example, vectors derived from bacterial plasmids, from bacteriophages or from viruses, or predominantly synthetic vectors. In addition, they are differentiated according to the nature of the cell types in which they are able to establish themselves, for example into vectors for gram-negative, for gram-positive bacteria, for yeasts or for higher eukaryotes. They are suitable starting points, for example, for molecular-biological and biochemical studies, and also for expression of the gene in question or of the corresponding protein.

In one embodiment, vectors of the invention are cloning vectors.

Cloning vectors are, in addition to storage, biological amplification or selection of the gene of interest, suitable for its molecular-biological characterization. At the same time, they are transportable and storable forms of the claimed nucleic acids and are also starting points for molecular-biological techniques not linked to cells, such as PCR or in-vitro mutagenesis methods, for example.

Preferably, vectors of the invention are expression vectors.

Expression vectors of this kind are the basis for implementing the corresponding nucleic acids in biological production systems and thereby producing the corresponding proteins. Preferred embodiments of this subject matter of the invention are expression vectors which carry the genetic elements necessary for expression, for example the natural promoter originally located upstream of said gene or a promoter from another organism. Said elements may be arranged, for example, the form of an "expression cassette". An alternative possibility is for one or all of the regulatory elements also to be provided by the host cell in each case. The expression vectors are particularly preferably adapted in relation to further properties such as, for example, the optimal copy number to the chosen expression system, in particular the host cell (see below).

For a high expression rate it is additionally advantageous for the expression vector where possible to comprise only the relevant gene as insert and no relatively large 5' or 3' noncoding regions. Such inserts are obtained for example when the fragment obtained after random treatment of the chromosomal DNA of the starting strain with a restriction enzyme has been cut deliberately once again after the sequencing and before integration into the expression vector.

One example of an expression vector is pAWA22 which is depicted in FIG. 2 of the present application and can be employed as disclosed in example 2. Further vectors are available to the skilled worker from the prior art and are commercially available in large numbers.

Cells which comprise one of the nucleic acid regions of the invention which are defined above, in particular one which codes for one of the proteins, protein fragments, fusion proteins or derivatives of the invention which are defined above, preferably on one of the vectors of the invention which are defined above, form an inherent aspect of the invention.

This is because these cells contain the genetic information for the synthesis of a protein of the invention. They make it possible, for example, for the corresponding genes to be amplified, but also to be mutagenized or transcribed and translated and eventually for the relevant proteins to be produced biotechnologically. This genetic information can be present either extrachromosomally as inherent genetic element, i.e. in bacteria located on a plasmid, or be integrated into a chromosome. The choice of a suitable system depends on objectives, such as, for example, the mode and duration of storage of the gene or of the organism, or the mode of mutagenesis or selection. Thus, mutagenesis and selection methods based for example on bacteriophages—and the specific host cells thereof—are described for the development of enzymes for washing products in the prior art (WO 97/09446).

Preference is given here to host cells which express or can be induced to express any of the proteins, protein fragments, fusion proteins or derivatives of the invention which are described above, in particular by using any of the nucleic acid regions of the invention which are defined above, very particularly by using an expression vector defined above.

The host cells producing said proteins make possible the biotechnological production thereof. For this purpose, they must have received the gene in question, conveniently with one of the vectors described above, and be capable of its transcription, translation and preferably the possibly additional modification steps.

Suitable host cells for protein expression are in principle all organisms, i.e. prokaryotes, eukaryotes or Cyanophyta. Preference is given to those host cells which are easily manageable genetically, with respect to, for example, transformation with the expression vector or to its stable establishment and to the regulation of expression, for example unicellular fungi or bacteria. Moreover, preferred host cells are distinguished by good microbiological and biotechnological manageability. This relates, for example, to easy culturability, high growth rates, low demands on fermentation media and good rates of production and secretion of foreign proteins. Laboratory strains aimed at expression are preferably chosen. Such strains are available commercially or from generally accessible strain collections. In this way, any protein of the invention can be obtained theoretically from a multiplicity of host organisms. It is necessary to determine experimentally the expression systems optimal for the individual case from the abundance of different systems available according to the prior art.

Host cells which are themselves protease-negative, and thus do not degrade produced proteins, are particularly advantageous. One such is the strain *Bacillus subtilis* DB 104 used in example 2.

Preferred embodiments are those host cells whose activity can be regulated owing to appropriate genetic elements, for example by controlled addition of chemical compounds, by changing the culturing conditions or as a function of the particular cell density. This controllable expression makes possible very economical production of the proteins of interest. Conveniently, gene, expression vector and host cell match one another, with respect to the genetic elements required for expression (ribosome-binding site, promoters, terminators) or to codon usage, for example. The latter, for example, may be optimized by replacing in the gene those codons which are translated only poorly by the host in question with those more commonly used by the particularly host, with identical meaning in each case.

Preferred among these are host cells which are characterized in that they are bacteria, in particular those which secrete the protein produced into the surrounding medium.

Bacteria distinguish themselves by short generation times and low demands on the culturing conditions. This makes it possible to establish cost-effective methods. Moreover, a wealth of experience in bacterial fermentation techniques is available. For a large variety of reasons to be determined experimentally in the individual case, such as nutrient sources, rate of product formation, time required, etc., Gram-negative or Gram-positive bacteria may be suitable for a specific production.

Gram-negative bacteria such as *E. coli*, for example, secrete a multiplicity of proteins into the periplasmic space. This may be advantageous for special applications. In contrast, Gram-positive bacteria such as bacilli, for example, release secreted proteins immediately into the nutrient medium surrounding the cells, from which the expressed proteins of the invention can be purified directly, according to another preferred embodiment.

The application WO 01/81597 discloses a method according to which export of the expressed proteins by Gram-negative bacteria is also achieved. Such a system is also suitable for producing proteins of the invention. Accordingly, preferred host cells are those of the species *Escherichia coli* or *Klebsiella*, especially those of the strains *E. coli* JM 109, *E. coli* DH 100B, *E. coli* DH 12S or *Klebsiella planticola* (Rf). They require appropriate microbiological modifications and/or suitable vectors described in this application to enable the produced proteins to be released.

Bacteria preferred as host cells are those characterized in that they are gram-positive bacteria, in particular that they belong to the genus *bacillus*, very particularly to the species *Bacillus lentus, Bacillus licheniformis, Bacillus amyloliquefaciens, Bacillus subtilis* or *Bacillus alcalophilus*.

One embodiment of the present invention utilizes *B. gibsonii*, in particular *B. gibsonii* (DSM 14391) itself, in order to (homologously) express proteins of the invention. On the other hand, however, preference is given to heterologous expression for which bacteria of the genus *Bacillus* are preferred, because they are the best characterized among Gram-positive bacteria, with respect to production. Included here are in particular those of the species *B. Licheniformis, B. amyloliquefaciens, B. subtilis* or other species or strains of *B. alcalophilus*. This is because relevant experience concerning protease production with these species is available, for example from the teaching of the application WO 91/02792. This application also discloses numerous possible expression vectors. These related species additionally have a similar codon usage and themselves produce comparable subtilisins, so that the protein synthesis system is naturally appropriately oriented.

Another advantage is the possibility of obtaining via this method a mixture of proteins of the invention with the subtilisins endogenously produced by the host strains. Such a coexpression is likewise disclosed in the application WO 91/02792. If it is unwanted, the protease genes naturally present in the host cell would need to be permanently or temporarily inactivated (see above).

Further preference is given to host cells characterized in that they are eukaryotic cells, in particular those which modify posttranslationally the protein produced.

Examples of suitable eukaryotes are fungi such as actinomycetes or yeasts such as *Saccharomyces* or *Kluyveromyces*. Thermophilic fungal expression systems are presented for example in WO 96/02653. They are particularly suitable for expressing thermally resistant variants. The modifications which eukaryotic systems carry out, in particular in connection with protein synthesis, include binding of low molecular compounds such as membrane anchors or oligosaccharides, for example. Oligosaccharide modifications of this kind may be desirable, for example, for reducing allergenicity. Coexpression with the enzymes naturally produced by such cells, such as, for example, cellulases may also be advantageous.

Methods for preparing a protein of the invention are a separate subject matter of the invention.

Thus, every method for producing a protein, protein fragment, fusion protein or derivative of the invention described above using a nucleic acid of the invention described above and/or using a vector of the invention described above and/or using one of the cells of the invention which are described above is thus claimed.

These include for example chemical synthetic methods, which are economically worthwhile in particular for shorter fragments.

However, all molecular biological, microbiological or biotechnological production methods which have already been mentioned above in individual aspects and are established in the prior art are preferred to the latter. Accordingly, it is possible for example on the basis of the DNA and amino acid sequences defined above, as can be deduced, for example also from the sequence listing, preferably on the basis of those from SEQ ID No. 1 and 2 themselves, to synthesize corresponding oligonucleotides and oligopeptides up to the complete genes and proteins according to molecular-biological methods known per se.

Starting from the known subtilisin-producing microorganisms, for example following the example in this application, it is also possible to identify and isolate further natural subtilisin producers, to determine their subtilisin gene and/or amino acid sequences and to develop them, according to the conditions made herein. Bacterial species of this kind may also be cultured for appropriate production methods. Analogously, novel expression vectors may be developed according to the model of the vectors disclosed in the application WO 91/02792. Cell-free expression systems in which protein biosynthesis is carried out in vitro may also be embodiments of the present invention, on the basis of the corresponding nucleic acid sequences. Any elements already set forth above may also be combined to give novel methods for preparing proteins of the invention. In this connection, a multiplicity of possible combinations of the method steps for each protein of the invention is conceivable so that optimal methods must be determined experimentally for each specific individual case.

A separate subject matter of the invention comprises products which are characterized in that they comprise a protein, protein fragment, fusion protein or derivative of the invention defined above.

All types of products, especially mixtures, formulations, solutions, etc. whose utilizability is improved by adding a protein of the invention described above are hereby included in the scope of protection of the present invention. Depending on the area of use, they may be, for example, solid mixtures, for example powders with freeze-dried or encapsulated proteins, or gelatinous or liquid products. Preferred formulations comprise for example buffer substances, stabilizers, reactants and/or cofactors of the proteases and/or other ingredients synergistic with the proteases. These are to be understood to include in particular products for the areas of use detailed hereinafter. Further areas of use are evident from the prior art and are described for example in the manual "Industrial enzymes and their applications" by H. Uhlig, published by Wiley, New York, 1998.

A preferred embodiment included in this subject matter of the invention are washing or cleaning products which are characterized in that they comprise one of the proteins, protein fragments, fusion proteins or derivatives of the invention which are described above.

This is because, as shown in the exemplary embodiments of the present application, it has surprisingly been found that the particularly preferred alkaline protease from *B. gibsonii* (DSM 14391), that is to say even the wild-type enzyme, is distinguished in that on use in a corresponding washing or cleaning product it at least approaches the enzymes established for this purpose in their contributions to the washing or cleaning performance, or in some cases in fact exceeds them.

This subject matter of the invention includes all conceivable types of cleaning products, both concentrates and products to be applied in undiluted form; for use on the commercial scale, in the washing machine or for manual laundry or cleaning. They include, for example, washing products for textiles, carpets or natural fibers, for which the term washing product is used in the present invention. They also include, for example, dishwashing agents for dishwashers or manual dishwashing agents or cleaners for hard surfaces such as metal, glass, porcelain, ceramic, tiles, stone, coated surfaces, plastics, wood or leather; for those, the term cleaning product is used in the present invention. Any type of washing or cleaning product is an embodiment of the present invention, as long as a protein, protein fragment, fusion protein or derivative of the invention has been added to it.

Embodiments of the present invention comprise any presentation forms of the washing or cleaning products of the invention, which are established in the prior art and/or appropriate. They include, for example, solid, pulverulent, liquid, gel-like or paste-like agents, where appropriate also composed of a plurality of phases, compressed or uncompressed; further examples include: extrudates, granules, tablets or pouches, packaged both in large containers and in portions.

In a preferred embodiment, the washing or cleaning products of the invention comprise the proteins, protein fragments, fusion proteins or derivatives of the invention described above in an amount of from 2 µg to 20 mg, preferably from 5 µg to 17.5 mg, particularly preferably from 20 µg to 15 mg, very particularly preferably from 50 µg to 10 mg, per gram of the product.

The protease activity in products of this kind may be determined according to the method described in *Tenside*, Volume 7 (1970), pp. 125-132 and is, accordingly, indicated in protease units (PE =Protease-Einheiten).

Apart from a protein, fragment, fusion protein or derivative of the invention, a washing or cleaning product of the invention contains, where appropriate, further ingredients such as enzyme stabilizers, surfactants, for example nonionic, anionic and/or amphoteric surfactants, and/or bleaches, and/or builders, and, where appropriate, further conventional ingredients, which are listed below.

The nonionic surfactants used are preferably alkoxylated, advantageously ethoxylated, in particular primary alcohols having preferably from 8 to 18 carbon atoms and, on average, from 1 to 12 mol of ethylene oxide (EO) per mole of alcohol, in which the alcohol radical can be linear or, preferably, methyl-branched in the 2-position or can comprise linear and methyl-branched radicals in a mixture as are customarily present in oxo alcohol radicals. Particular preference is, however, given to alcohol ethoxylates containing linear radicals of alcohols of native origin having from 12 to 18 carbon atoms, for example from coconut, palm, tallow fatty or oleyl alcohol, and, on average, from 2 to 8 EO per mole of alcohol. Preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-14}$-alcohols having 3 EO, 5 EO or 7 EO, and mixtures of these, such as mixtures of $C_{12-14}$-alcohol having 3 EO and $C_{12-18}$-alcohol having 5 EO. The degrees of ethoxylation given are statistical averages which may be an integer or a fraction for a specific product. Preferred alcohol ethoxylates have a narrowed homolog distribution (narrow range ethoxylates, NRE). In addition to these nonionic surfactants, fatty alcohols having more than 12 EO can also be used. Examples thereof are tallow fatty alcohol having 14 EO, 25 EO, 30 EO or 40 EO.

A further class of preferably used nonionic surfactants which are used either as the sole nonionic surfactant or in combination with other nonionic surfactants are alkoxylated, preferably ethoxylated or ethoxylated and propoxylated, fatty acid alkyl esters, preferably having from 1 to 4 carbon atoms in the alkyl chain, in particular fatty acid methyl esters.

A further class of nonionic surfactants which can advantageously be used are the alkyl polyglycosides (APG). Alkyl polyglycosides which may be used satisfy the general formula $RO(G)_z$, in which R is a linear or branched, in particular methyl-branched in the 2-position, saturated or unsaturated, aliphatic radical having from 8 to 22, preferably from 12 to 18 carbon atoms, and G is the symbol which stands for a glycose unit having 5 or 6 carbon atoms, preferably for glucose. The degree of glycosylation z is here between 1.0 and 4.0, preferably between 1.0 and 2.0 and in particular between 1.1 and 1.4. Preference is given to using linear alkyl polyglucosides, i.e. alkyl polyglycosides in which the polyglycosyl radical is a glucose radical, and the alkyl radical is a n-alkyl radical.

Nonionic surfactants of the amine oxide type, for example N-cocoalkyl-N,N-dimethylamine oxide and N-tallow alkyl-N,N-dihydroxyethylamine oxide, and of the fatty acid alkanolamides may also be suitable. The proportion of these nonionic surfactants is preferably no more than that of the ethoxylated fatty alcohols, in particular no more than half thereof.

Further suitable surfactants are polyhydroxy fatty acid amides of the formula (II)

(II)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (III)

(III)

in which R is a linear or branched alkyl or alkenyl radical having from 7 to 12 carbon atoms, $R^1$ is a linear, branched or cyclic alkyl radical or an aryl radical having from 2 to 8 carbon atoms, and R is a linear, branched or cyclic alkyl radical or an aryl radical or an oxyalkyl radical having from 1 to 8 carbon atoms, where $C_{1-4}$-alkyl or phenyl radicals are preferred, and [Z] is a linear polyhydroxyalkyl radical whose alkyl chain is substituted with at least two hydroxyl groups, or alkoxylated, preferably ethoxylated or propoxylated, derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds may be converted, for example, by reaction with fatty acid methyl esters in the presence of an alkoxide as catalyst, into the desired polyhydroxy fatty acid amides.

The anionic surfactants used are, for example, those of the sulfonate and sulfate type. Suitable surfactants of the sulfonate type are preferably $C_{9-13}$-alkylbenzenesulfonates, olefinsulfonates, i.e. mixtures of alkene- and hydroxyalkanesulfonates, and disulfonates, as obtained, for example, from $C_{12-18}$-monoolefins having a terminal or internal double bond by sulfonation with gaseous sulfur trioxide and subsequent alkaline or acidic hydrolysis of the sulfonation products. Also suitable are alkanesulfonates which are obtained from $C_{12-18}$-alkanes, for example, by sulfochlorination or sulfoxidation with subsequent hydrolysis or neutralization. Likewise suitable are also the esters of α-sulfo fatty acids (estersulfonates), for example the α-sulfonated methyl esters of hydrogenated coconut, palm kernel or tallow fatty acids.

Further suitable anionic surfactants are sulfated fatty acid glycerol esters. Fatty acid glycerol esters mean the mono-, di- and triesters, and mixtures thereof, as are obtained during the preparation by esterification of a monoglycerol with from 1 to 3 mol of fatty acid or during the transesterification of triglycerides with from 0.3 to 2 mol of glycerol. Preferred sulfated fatty acid glycerol esters are here the sulfation products of saturated fatty acids having from 6 to 22 carbon atoms, for example of caproic acid, caprylic acid, capric acid, myristic acid, lauric acid, palmitic acid, stearic acid or behenic acid.

Preferred alk(en)yl sulfates are the alkali metal, and in particular the sodium, salts of sulfuric monoesters of $C_{12}$-$C_{18}$-fatty alcohols, for example of coconut fatty alcohol, tallow fatty alcohol, lauryl, myristyl, cetyl or stearyl alcohol or of $C_{10}$-$C_{20}$-oxo alcohols and those monoesters of secondary alcohols of these chain lengths. Further preferred are alk(en)yl sulfates of said chain length which comprise a synthetic, petrochemical-based straight-chain alkyl radical and have analogous degradation behavior to the equivalent compounds based on fatty chemical raw materials. From a washing performance viewpoint, preference is given to $C_{12}$-$C_{16}$-alkyl sulfates and $C_{12}$-$C_{15}$-alkyl sulfates, and $C_{14}$-$C_{15}$-alkyl sulfates. 2,3-Alkyl sulfates are also suitable anionic surfactants.

The sulfuric monoesters of straight-chain or branched $C_{7-21}$-alcohols ethoxylated with from 1 to 6 mol of ethylene oxide, such as 2-methyl-branched $C_{9-11}$ alcohols having, on average, 3.5 mol of ethylene oxide (EO) or $C_{12-18}$-fatty alcohols having from 1 to 4 EO, are also suitable. Owing to their high foaming behavior, they are used in cleaning agents only in relatively small amounts, for example in amounts up to 5% by weight, usually from 1 to 5% by weight.

Further suitable anionic surfactants are also the salts of alkylsulfosuccinic acid, which are also referred to as sulfosuccinates or as sulfosuccinic esters and which are monoesters and/or diesters of sulfosuccinic acid with alcohols, preferably fatty alcohols and, in particular, ethoxylated fatty alcohols. Preferred sulfosuccinates contain $C_{8-18}$-fatty alcohol radicals or mixtures thereof. Particularly preferred sulfosuccinates contain a fatty alcohol radical derived from ethoxylated fatty alcohols, which are themselves nonionic surfactants (see above for description). In this connection, sulfosuccinates whose fatty alcohol radicals are derived from ethoxylated fatty alcohols having a narrowed homolog distribution are, in turn, particularly preferred. Likewise, it is also possible to use alk(en)ylsuccinic acid having preferably from 8 to 18 carbon atoms in the alk(en)yl chain or salts thereof.

Further suitable anionic surfactants are, in particular, soaps. Saturated fatty acid soaps such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants including soaps may be present in the form of their sodium, potassium or ammonium salts, and as soluble salts of organic bases such as mono-, di- or triethanolamine. The anionic surfactants are preferably in the form of their sodium or potassium salts, in particular in the form of the sodium salts.

The surfactants may be present in the cleaning or washing products of the invention in an overall amount of from preferably 5% by weight to 50% by weight, in particular from 8% by weight to 30% by weight, based on the finished product.

Washing or cleaning products of the invention may contain bleaches. Of the compounds which serve as bleaches and produce $H_2O_2$ in water, sodium percarbonate, sodium perborate tetrahydrate and sodium perborate monohydrate are of particular importance. Other bleaches which can be used are, for example, peroxopyrophosphates, citrate perhydrates and $H_2O_2$-producing peracidic salts or peracids, such as persulfates or persulfuric acid. Also useful is the urea peroxohydrate percarbamide which can be described by the formula $H_2N$—$CO$—$NH_2.H_2O_2$. In particular when used for cleaning hard surfaces, for example for machine dishwashing, the agents, if desired, may also contain bleaches from the group of organic bleaches, although the use thereof is possible in principle also in agents for washing textiles. Typical organic bleaches are diacyl peroxides such as, for example, dibenzoyl peroxide. Further typical organic bleaches are the peroxy acids, specific examples being alkyl peroxy acids and aryl peroxy acids. Preferred representatives are peroxy benzoic acid and its ring-substituted derivatives, such as alkylperoxybenzoic acids, but also peroxy-α-naphthoic acid and magnesium monoperphthalate, the aliphatic or substituted aliphatic peroxy acids such as peroxylauric acid, peroxystearic acid, ε-phthalimidoperoxycaproic acid (phthalimidoperoxyhexanoic acid, PAP), o-carboxybenzamidoperoxycaproic acid, N-nonenylamidoperadipic acid and N-nonenylamidopersuccinates, and aliphatic and araliphatic peroxydicarboxylic acids such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyldi(6-aminopercaproic acid) may be used.

The bleach content of the washing or cleaning products may be from 1 to 40% by weight and, in particular, from 10 to 20% by weight, using advantageously perborate monohydrate or percarbonate.

In order to achieve improved bleaching action in cases of washing at temperatures of 60° C. and below, and in particular in the case of laundry pretreatment, the agents may also include bleach activators. Bleach activators which can be used are compounds which, under perhydrolysis conditions, give aliphatic peroxocarboxylic acids having preferably from 1 to 10 carbon atoms, in particular from 2 to 4 carbon atoms, and/or substituted or unsubstituted perbenzoic acid. Substances which carry O- and/or N-acyl groups of said number of carbon atoms and/or substituted or unsubstituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular 1,3,4,6-tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), acylated hydroxycarboxylic acids such as triethyl O-acetylcitrate (TEOC), carboxylic anhydrides, in particular phthalic anhydride, isatoic anhydride and/or succinic anhydride, carboxamides such as N-methyldiacetamide, glycolide, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767, and acetylated sorbitol and mannitol, or mixtures thereof described in European patent application EP 0 525 239 (SORMAN), acylated sugar derivatives, in particular pentaacetylglucose (PAG), pentaacetylfructose, tetraacetylxylose and octaacetyllactose, and acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam, which are disclosed in international patent applications WO 94/27970, WO 94/28102, WO 94/28103, WO 95/00626, WO 95/14759 and WO 95/17498. The hydrophilically substituted acyl acetals disclosed in German patent application DE 196 16 769 and the acyl lactams described in German patent application DE 196 16 770 and in international patent application WO 95/14075 are likewise used with preference. It is also possible to use the combinations of conventional bleach activators disclosed in German patent application DE 44 43 177. Nitrile derivatives such as cyanopyridines, nitrile quats, e.g. N-alkylammonium acetonitriles, and/or cyanamide derivatives may also be used. Preferred bleach activators are sodium 4-(octanoyloxy)benzenesulfonate, n-nonanoyl- or isononanoyloxybenzenesulfonate (n- or iso-NOBS), undecenoyloxy-benzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12), and N-methylmorpholinium acetonitrile (MMA). Such bleach activators may be present in the customary quantitative range from 0.01 to 20% by weight, preferably in amounts from 0.1 to 15% by weight, in particular 1% by weight to 10% by weight, based on the total composition.

In addition to the conventional bleach activators or instead of them, it is also possible for "bleach catalysts" to be present. These substances are bleach-enhancing transition metal salts or transition metal complexes such as, for example, Mn, Fe, Co, Ru or Mo salen complexes or carbonyl complexes. Mn, Fe, Co, Ru, Mo, Ti, V and Cu complexes containing N-containing tripod ligands, and Co, Fe, Cu and Ru ammine complexes are also suitable as bleach catalysts, preference being given to using those compounds described in DE 19709284 A1.

Washing or cleaning products of the invention usually contain one or more builders, in particular zeolites, silicates, carbonates, organic cobuilders and, where no ecological reasons oppose their use, also phosphates. The latter are the preferred builders for use in particular in cleaning products for machine dishwashing.

Compounds which may be mentioned here are crystalline, layered sodium silicates of the general formula $NaMSi_xO_{2x+1} \cdot yH_2O$, where M is sodium or hydrogen, x is a number from 1.6 to 4, preferably from 1.9 to 4.0, and y is a number from 0 to 20, and preferred values for x are 2, 3 or 4. Crystalline phyllosilicates of this kind are described, for example, in European patent application EP 164514. Preferred crystalline phyllosilicates of the formula indicated are those where M is sodium and x adopts the values 2 or 3. In particular, both β- and δ-sodium disilicates $Na_2Si_2O_5 \cdot yH_2O$ are preferred. Compounds of this kind are sold, for example, under the name SKS® (Clariant). Thus, SKS-6® is primarily a δ-sodium disilicate having the formula $Na_2Si_2O_5 \cdot yH_2O$, and SKS-7® is primarily the β-sodium disilicate. Reacting the δ-sodium disilicate with acids (for example citric acid or carboxylic acid) gives kanemite, $NaHSi_2O_5 \cdot yH_2O$, sold under the names SKS-9® and, respectively, SKS-10® (Clariant). It may also be advantageous to use chemical modifications of said phyllosilicates. The alkalinity of the phyllosilicates, for example, can thus be suitably influenced. Phyllosilicates doped with phosphate or with carbonate have, compared to the δ-sodium disilicate, altered crystal morphologies, dissolve more rapidly and display an increased calcium binding ability, compared to δ-sodium disilicate. Thus, phyllosilicates of the general empirical formula $xNa_2O \cdot ySiO_2O \cdot zP_2O_5$ where the x-to-y ratio corresponds to a number from 0.35 to 0.6, the x-to-z ratio to a number from 1.75 to 1 200 and the y-to-z ratio to a number from 4 to 2 800 are described in patent application DE 196 01 063. The solubility of the phyllosilicates may also be increased by using particularly finely granulated phyllosilicates. It is also possible to use compounds of the crystalline phyllosilicates with other ingredients. Compounds which may be mentioned here are in particular those with cellulose derivatives which have advantageous disintegrating action and are used in particular in detergent tablets, and those with polycarboxylates, for example citric acid, or polymeric polycarboxylates, for example copolymers of acrylic acid.

It is also possible to use amorphous sodium silicates having a $Na_2O:SiO_2$ modulus of from 1:2 to 1:3.3, preferably from 1:2 to 1:2.8, and in particular from 1:2 to 1:2.6, which have delayed dissolution and secondary detergent properties. The dissolution delay relative to conventional amorphous sodium silicates can have been induced by various means, for example by surface treatment, compounding, compaction/compression or by overdrying. Within the scope of this invention, the term "amorphous" also means "X-ray amorphous". This means that in X-ray diffraction experiments the silicates do not give the sharp X-ray reflections typical of crystalline substances, but instead, at best, one or more maxima of the scattered X-ray radiation, which have a width of several degree units of the diffraction angle. However, even particularly good builder properties will very likely result if, in electron diffraction experiments, the silicate particles give poorly defined or even sharp diffraction maxima. This is to be interpreted to the effect that the products have microcrystalline regions with a size from 10 to a few hundred nm, preference being given to values up to at most 50 nm and in particular up to at most 20 nm. Particular preference is given to compressed/compacted amorphous silicates, compounded amorphous silicates and overdried X-ray amorphous silicates.

A finely crystalline, synthetic zeolite containing bonded water, which may be used where appropriate, is preferably zeolite A and/or P. As zeolite P, zeolite MAP® (commercial product from Crosfield) is particularly preferred. However, zeolite X and mixtures of A, X and/or P are also suitable. A product which is commercially available and can be used with preference within the scope of the present invention is, for example, also a cocrystal of zeolite X and zeolite A (approx. 80% by weight zeolite X), which is sold by CONDEA Augusta S.p.A. under the trade name VEGOBOND AX(® and can be described by the formula

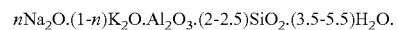
$nNa_2O \cdot (1-n)K_2O \cdot Al_2O_3 \cdot (2-2.5)SiO_2 \cdot (3.5-5.5)H_2O.$ Suitable zeolites have an average particle size of less than 10 μm (volume distribution; measurement method: Coulter counter) and preferably contain from 18 to 22% by weight, in particular from 20 to 22% by weight, of bonded water.

Use of the generally known phosphates as builder substances is of course also possible, provided such a use should not be avoided for ecological reasons. Among the multiplicity of commercially available phosphates, the alkali metal phosphates are the most important in the detergents and cleaning agents industry, with pentasodium or pentapotassium triphosphate (sodium or potassium tripolyphosphate) being particularly preferred.

In this connection, alkali metal phosphates is the collective term for the alkali metal (in particular sodium and potassium) salts of the various phosphoric acids, it being possible to differentiate between metaphosphoric acids $(HPO_3)_n$ and orthophosphoric acid $H_3PO_4$ as well as higher molecular weight representatives. The phosphates combine several advantages: they act as alkali carriers, prevent lime deposits on machine parts and lime incrustations in fabrics and, moreover, contribute to the cleaning performance.

Sodium dihydrogenphosphate, $NaH_2PO_4$, exists as dihydrate (density 1.91 gcm$^{-3}$, melting point 60° C.) and as monohydrate (density 2.04 gcm$^{-3}$). Both salts are white powders which are very readily soluble in water and which lose their water of crystallization upon heating and at 200° C. convert to the weakly acidic diphosphate (disodium hydrogendiphosphate, $Na_2H_2P_2O_7$), at a higher temperature to sodium trimetaphosphate $(Na_3P_3O_9)$ and Maddrell's salt (see below). $NaH_2PO_4$ is acidic; it forms when phosphoric acid is adjusted to a pH of 4.5 using sodium hydroxide solution and the slurry is sprayed. Potassium dihydrogenphosphate (primary or monobasic potassium phosphate, potassium biphosphate, KDP), $KH_2PO_4$, is a white salt of density 2.33 gcm$^{-3}$, has a melting point of 253° C. [decomposition with the formation of potassium polyphosphate $(KPO_3)_x$] and is readily soluble in water.

Disodium hydrogenphosphate (secondary sodium phosphate), $Na_2HPO_4$, is a colorless crystalline salt which is very readily soluble in water. It exists in anhydrous form and with 2 mol (density 2.066 gcm$^{-3}$, loss of water at 95° C.), 7 mol (density 1.68 gcm$^{-3}$, melting point 48° C. with loss of 5 $H_2O$), and 12 mol (density 1.52 gcm$^{-3}$, melting point 35° C. with loss of 5 $H_2O$) of water, becomes anhydrous at 100° C. and upon more vigorous heating converts to the diphosphate $Na_4P_2O_7$. Disodium hydrogenphosphate is prepared by neutralizing phosphoric acid with sodium carbonate solution using phenolphthalein as indicator. Dipotassium hydrogenphosphate (secondary or dibasic potassium phosphate), $K_2HPO_4$, is an amorphous, white salt which is readily soluble in water.

Trisodium phosphate, tertiary sodium phosphate, $Na_3PO_4$, are colorless crystals which, in the form of the dodecahydrate, have a density of 1.62 gcm$^{-3}$ and a melting point of 73-76° C. (decomposition), in the form of the decahydrate (corresponding to 19-20% $P_2O_5$) have a melting point of 100° C. and in anhydrous form (corresponding to 39-40% $P_2O_5$) have a density of 2.536 gcm$^{-3}$. Trisodium phosphate is readily soluble in water with an alkaline reaction and is prepared by evaporating a solution of exactly 1 mol of disodium phosphate and 1 mol of NaOH. Tripotassium phosphate (tertiary or tribasic potassium phosphate), $K_3PO_4$, is a white, deliquescent granular powder of density 2.56 gcm$^{-3}$, has a melting point of 1 340° C. and is readily soluble in water with an alkaline reaction. It is produced, for example, during the heating of Thomas slag with carbon and potassium sulfate. Despite the higher price, the more readily soluble, and therefore highly effective, potassium phosphates are often preferred over corresponding sodium compounds in the cleaning agents industry.

Tetrasodium diphosphate (sodium pyrophosphate), $Na_4P_2O_7$, exists in anhydrous form (density 2.534 gcm$^{-3}$, melting point 988° C., also 880° C. quoted) and as decahydrate (density 1.815-1.836 gcm$^{-3}$, melting point 94° C. with loss of water). Both substances are colorless crystals which dissolve in water with an alkaline reaction. $Na_4P_2O_7$ is formed during the heating of disodium phosphate to >200° C. or by reacting phosphoric acid with sodium carbonate in a stoichiometric ratio and dewatering the solution by spraying. The decahydrate complexes heavy metal salts and hardness constituents and thus reduces the water hardness. Potassium diphosphate (potassium pyrophosphate), $K_4P_2O_7$, exists in the form of the trihydrate and is a colorless, hygroscopic powder of density 2.33 gcm$^{-3}$, which is soluble in water, the pH of the 1% strength solution at 25° C. being 10.4.

Condensation of $NaH_2PO_4$ and $KH_2PO_4$ results in higher molecular weight sodium phosphates and potassium phosphates, respectively, amongst which cyclic representatives, the sodium and potassium metaphosphates, respectively, and chain-like types, the sodium and potassium polyphosphates, respectively, can be differentiated. Particularly for the latter, a multiplicity of names are in use: melt or thermal phosphates, Graham's salt, Kurrol's and Maddrell's salt. All higher sodium and potassium phosphates are together referred to as condensed phosphates.

The industrially important pentasodium triphosphate, $Na_5P_3O_{10}$ (sodium tripolyphosphate), is a nonhygroscopic, white, water-soluble salt which is anhydrous or crystallizes with 6 $H_2O$ and is of the general formula NaO—[P(O)(ONa)—O]$_n$—Na where n=3. In 100 g of water, about 17 g of the salt which is free of water of crystallization dissolve at room temperature, approx. 20 g dissolve at 60° C., and about 32 g dissolve at 100° C.; if the solution is heated at 100° C. for two hours, about 8% of orthophosphate and 15% of diphosphate form due to hydrolysis. In the preparation of pentasodium triphosphate, phosphoric acid is reacted with sodium carbonate solution or sodium hydroxide solution in a stoichiometric ratio, and the solution is dewatered by spraying. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is available commercially, for example, in the form of a 50% strength by weight solution (>23% $P_2O_5$, 25% $K_2O$). The potassium polyphosphates are used widely in the detergents and cleaning agents industry. In addition, sodium potassium tripolyphosphates also exist which can likewise be used within the scope of the present invention. These form, for example, when sodium trimetaphosphate is hydrolyzed with KOH:

$$(NaPO_3)_3 + 2KOH \rightarrow Na_3K_2P_3O_{10} + H_2O$$

According to the invention, these can be used in exactly the same way as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Organic cobuilders which can be used in the washing and cleaning products of the invention are, in particular, polycarboxylates or polycarboxylic acids, polymeric polycarboxylates, polyaspartic acid, polyacetals, optionally oxidized dextrins, further organic cobuilders (see below), and phosphonates. These classes of substance are described below.

Useable organic builder substances are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), as long as such a use is not to be avoided for ecological reasons, and mixtures thereof. Preferred salts are the salts of the polycarboxylic acids such as citric acid, adipic acid, succinic acid, glutaric acid, tartaric acid, sugar acids, and mixtures thereof.

It is also possible to use the acids per se. In addition to their builder action, the acids typically also have the property of an acidifying component and thus also serve to establish a lower and milder pH of detergents or cleaning agents, if the pH resulting from the mixture of the remaining components is not desired. Particular mention should be made here of system-compatible and environmentally safe acids such as citric acid, acetic acid, tartaric acid, malic acid, lactic acid, glycolic acid, succinic acid, glutaric acid, adipic acid, gluconic acid and any mixtures thereof. However, mineral acids, in particular sulfuric acid, or bases, in particular ammonium or alkali metal hydroxides, may also serve as pH regulators. The agents of the invention contain such regulators in amounts of preferably not more than 20% by weight, in particular from 1.2% by weight to 17% by weight.

Suitable builders are also polymeric polycarboxylates; these are, for example, the alkali metal salts of polyacrylic acid or of polymethacrylic acid, for example those having a relative molecular mass of from 500 to 70 000 g/mol.

The molar masses given for polymeric polycarboxylates are, for the purposes of this specification, weight-average molar masses, $M_w$, of the respective acid form, always determined by means of gel permeation chromatography (GPC), using a UV detector. The measurement was made against an external polyacrylic acid standard which, owing to its structural similarity towards the polymers studied, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are, in particular, polyacrylates which preferably have a molecular mass of from 2 000 to 20 000 g/mol. Owing to their superior solubility, preference in this group may be given in turn to the short-chain polyacrylates which have molar masses of from 2 000 to 10 000 g/mol, and particularly preferably from 3 000 to 5 000 g/mol.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and from 50 to 10% by weight of maleic acid. Their relative molecular mass, based on free acids, is generally from 2 000 to 70 000 g/mol, preferably 20 000 to 50 000 g/mol and in particular 30 000 to 40 000 g/mol. The (co)polymeric polycarboxylates may be used either as powders or as aqueous solution. The (co)polymeric polycarboxylates may be from 0.5 to 20% by weight, in particular 1 to 10% by weight of the content of the product.

To improve the solubility in water, the polymers may also contain allylsulfonic acids such as, for example, allyloxybenzenesulfonic acid and methallylsulfonic acid as monomers.

Particular preference is also given to biodegradable polymers of more than two different monomer units, for example those which contain, as monomers, salts of acrylic acid and of maleic acid, and vinyl alcohol or vinyl alcohol derivatives, or those which contain, as monomers, salts of acrylic acid and of 2-alkylallylsulfonic acid, and sugar derivatives.

Further preferred copolymers are those which preferably have, as monomers, acrolein and acrylic acid/acrylic acid salts or acrolein and vinyl acetate.

Further preferred builder substances which may be mentioned are also polymeric aminodicarboxylic acids, their salts or their precursor substances. Particular preference is given to polyaspartic acids or salts and derivatives thereof.

Further suitable builder substances are polyacetals which can be obtained by reacting dialdehydes with polyolcarboxylic acids having from 5 to 7 carbon atoms and at least 3 hydroxyl groups. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary processes, for example acid-catalyzed or enzyme-catalyzed processes. The hydrolysis products preferably have average molar masses in the range from 400 to 500 000 g/mol. Preference is given here to a polysaccharide having a dextrose equivalent (DE) in the range from 0.5 to 40, in particular from 2 to 30, where DE is a common measure of the reducing action of a polysaccharide compared with dextrose which has a DE of 100. It is possible to use both maltodextrins having a DE between 3 and 20 and dried glucose syrups having a DE between 20 and 37, and also "yellow dextrins" and "white dextrins" with higher molar masses in the range from 2 000 to 30 000 g/mol.

The oxidized derivatives of such dextrins are their reaction products with oxidizing agents which are able to oxidize at least one alcohol function of the saccharide ring to the carboxylic acid function. Particularly preferred organic builders for agents of the invention are oxidized starches and derivatives thereof of the applications EP 472042, WO 97/25399 and EP 755944, respectively.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. In this connection, further preference is also given to glycerol disuccinates and glycerol trisuccinates. Suitable use amounts in zeolite-containing, carbonate-containing and/or silicate-containing formulations are between 3 and 15% by weight.

Further organic cobuilders which can be used are, for example, acetylated hydroxy carboxylic acids or salts thereof, which may also be present, where appropriate, in lactone form and which contain at least 4 carbon atoms and at least one hydroxy group and at most two acid groups.

A further class of substance having cobuilder properties is the phosphonates. These are, in particular, hydroxyalkane- and aminoalkanephosphonates. Among the hydroxyalkanephosphonates, 1-hydroxyethanel,1-diphosphonate (HEDP) is of particular importance as a cobuilder. It is preferably used as sodium salt, the disodium salt being neutral and the tetrasodium salt being alkaline (pH 9). Suitable aminoalkanephosphonates are preferably ethylenediaminetetramethylenephosphonate (EDTMP), diethylenetriaminepentamethylenephosphonate (DTPMP) and higher homologs thereof. They are preferably used in the form of the neutral sodium salts, for example as the hexasodium salt of EDTMP or as the hepta- and octasodium salt of DTPMP. Here, preference is given to using HEDP as builder from the class of phosphonates. In addition, the aminoalkanephosphonates have a marked heavy metal-binding capacity. Accordingly, particularly if the agents also contain bleaches, it may be preferable to use aminoalkanephosphonates, in particular DTPMP, or mixtures of said phosphonates.

In addition, all compounds which are able to form complexes with alkaline earth metal ions can be used as cobuilders.

The washing or cleaning products of the invention may contain builder substances, where appropriate, in amounts of up to 90% by weight, and preferably contain them in amounts of up to 75% by weight. Washing products of the invention have builder contents of, in particular, from 5% by weight to 50% by weight. In inventive products for cleaning hard surfaces, in particular for machine cleaning of dishes, the builder substance content is in particular from 5% by weight to 88% by weight, with preferably no water-insoluble builder materials being used in such products. A preferred embodiment of inventive products for, in particular, machine cleaning of dishes contains from 20% by weight to 40% by weight water-soluble organic builders, in particular alkali metal citrate, from 5% by weight to 15% by weight alkali metal carbonate and from 20% by weight to 40% by weight alkali metal disilicate.

Solvents which may be used in the liquid to gelatinous compositions of washing and cleaning products are, for example, from the group of monohydric or polyhydric alcohols, alkanolamines or glycol ethers, as long as they are miscible with water in the given concentration range. Preferably, the solvents are selected from ethanol, n- or isopropanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Solvents may be used in the liquid to gelatinous washing and cleaning products of the invention in amounts of between 0.1 and 20% by weight, but preferably below 15% by weight, and in particular below 10% by weight.

To adjust the viscosity, one or more thickeners or thickening systems may be added to the composition of the invention. These high molecular weight substances which are also called swell(ing) agents usually soak up the liquids and swell in the process, converting ultimately into viscous, true or colloidal solutions.

Suitable thickeners are inorganic or polymeric organic compounds. Inorganic thickeners include, for example, polysilicic acids, clay minerals, such as montmorillonites, zeolites, silicas and bentonites. The organic thickeners are from the groups of natural polymers, modified natural polymers and completely synthetic polymers. Such natural polymers are, for example, agar-agar, carrageen, tragacanth, gum arabic, alginates, pectins, polyoses, guar flour, carob seed flour, starch, dextrins, gelatins and casein. Modified natural substances which are used as thickeners are primarily from the group of modified starches and celluloses. Examples which may be mentioned here are carboxymethylcellulose and other cellulose ethers, hydroxyethylcellulose and hydroxypropylcellulose, and carob flour ether. Completely synthetic thickeners are polymers such as polyacrylic and polymethacrylic compounds, vinyl polymers, polycarboxylic acids, polyethers, polyimines, polyamides and polyurethanes.

The thickeners may be present in an amount up to 5% by weight, preferably from 0.05 to 2% by weight, and particularly preferably from 0.1 to 1.5% by weight, based on the finished composition.

The washing and cleaning product of the invention may, where appropriate, comprise, as further customary ingredients, sequestering agents, electrolytes and further excipients such as optical brighteners, graying inhibitors, silver corrosion inhibitors, color transfer inhibitors, foam inhibitors, abrasive substances, dyes and/or fragrances, and microbial active substances, UV-absorbents and/or enzyme stabilizers.

The textile washing products of the invention may contain, as optical brighteners, derivatives of diaminostilbenedisulfonic acid or alkali metal salts thereof. Suitable are, for example, salts of 4,4'-bis(2-anilino-4-morpholino-1,3,5-triazinyl-6-amino)stilbene-2,2'-disulfonic acid or similarly constructed compounds which carry a diethanolamino group, a methylamino group, an anilino group or a 2-methoxyethylamino group instead of the morpholino group. In addition, brighteners of the substituted diphenylstyryl type may be present, for example the alkali metal salts of 4,4'-bis(2-sulfostyryl)diphenyl, 4,4'-bis(4-chloro-3-sulfostyryl)diphenyl, or 4-(4-chlorostyryl)-4'-(2-sulfostyryl)diphenyl. Mixtures of the abovementioned optical brighteners may also be used.

Graying inhibitors have the function of keeping the soil detached from the textile fiber in suspension in the liquor. Suitable for this purpose are water-soluble colloids, usually organic in nature, for example starch, size, gelatin, salts of ethercarboxylic acids or ethersulfonic acids of starch or of cellulose, or salts of acidic sulfuric esters of cellulose or of starch. Water-soluble polyamides containing acidic groups are also suitable for this purpose. Furthermore, starch derivatives other than those mentioned above may be used, for example aldehyde starches. Preference is given to cellulose ethers such as carboxymethylcellulose (Na salt), methylcellulose, hydroxyalkylcellulose and mixed ethers such as methylhydroxyethylcellulose, methylhydroxypropylcellulose, methylcarboxymethylcellulose, and mixtures thereof, for example in amounts of from 0.1 to 5% by weight, based on the agents.

In order to protect against silver corrosion, silver corrosion inhibitors may be used in dishwashing cleaning products of the invention. Such inhibitors are known in the prior art, for example benzotriazoles, iron(m) chloride or $CoSO_4$. As disclosed by, for example, European patent EP 0 736 084 B1, silver corrosion inhibitors which are particularly suitable for being used together with enzymes are manganese, titanium, zirconium, hafnium, vanadium, cobalt, or cerium salts and/or complexes in which the specified metals are present in any of the oxidation states II, III, IV, V or VI. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

Soil-release active ingredients or soil repellents are usually polymers which, when used in a washing product, impart soil-repellent properties to the laundry fiber and/or assist the ability of the other washing product ingredients to detach soil. A comparable effect can also be observed with their use in cleaning products for hard surfaces.

Soil-release active ingredients which are particularly effective and have been known for a long time are copolyesters having dicarboxylic acid, alkylene glycol and polyalkylene glycol units. Examples thereof are copolymers or mixed polymers of polyethylene terephthalate and polyoxyethylene glycol (DT 16 17 141, and, respectively, DT 22 00 911). German Laid-Open Specification DT 22 53 063 discloses acidic agents containing, inter alia, a copolymer of a dibasic carboxylic acid and an alkylene or cycloalkylene polyglycol. German documents DE 28 57 292 and DE 33 24258 and European patent EP 0 253 567 describe polymers of ethylene terephthalate and polyethylene oxide terephthalate and the use thereof in washing products. European patent EP 066 944 relates to products containing a copolyester of ethylene glycol, polyethylene glycol, aromatic dicarboxylic acid and sulfonated aromatic dicarboxylic acid in particular molar ratios. European patent EP 0 185 427 discloses methyl or ethyl group end-capped polyesters having ethylene and/or propylene terephthalate and polyethylene oxide terephthalate units, and detergents containing such a soil-release polymer. European patent EP 0 241 984 discloses a polyester which contains, in addition to oxyethylene groups and terephthalic acid units, also substituted ethylene units and glycerol units. European patent EP 0 241 985 discloses polyesters which contain, in addition to oxyethylene groups and terephthalic acid units, 1,2-propylene, 1,2-butylene and/or 3-methoxy-1,2-propylene groups, and glycerol units and which are end-group-capped with $C_1$- to $C_4$-alkyl groups. European patent application EP 0 272 033 discloses polyesters having polypropylene terephthalate and polyoxyethylene terephthalate units, which are at least partially end-group-capped by $C_{1-4}$-alkyl or acyl radicals. European patent EP 0 274 907 describes sulfoethyl end-group-capped terephthalate-containing soil-release polyesters. According to European patent application EP 0 357 280, sulfonation of unsaturated end groups produces soil-release polyesters having terephthalate, alkylene glycol and poly-$C_{2-4}$-glycol units. International patent application WO 95/32232 relates to acidic, aromatic polyesters capable of detaching soil. International patent application WO 97/31085 discloses nonpolymeric soil-repellent active ingredients for materials made of cotton, which have a plurality of functional units: a first unit which may be cationic, for example, is able to adsorb to the cotton surface by means of electrostatic interaction, and a second unit which is hydrophobic is responsible for the active ingredient remaining at the water/cotton interface.

The color transfer inhibitors suitable for use in laundry washing products of the invention include, in particular, polyvinylpyrrolidones, polyvinylimidazoles, polymeric N-oxides such as poly(vinylpyridine N-oxide) and copolymers of vinylpyrrolidone with vinylimidazole.

For use in machine cleaning processes, it may be of advantage to add foam inhibitors to the relevant products. Examples of suitable foam inhibitors are soaps of natural or synthetic origin having a high proportion of $C_{18-C24}$ fatty acids. Examples of suitable nonsurfactant-type foam inhibitors are organopolysiloxanes and their mixtures with microfine, optionally silanized silica and also paraffins, waxes, microcrystalline waxes, and mixtures thereof with silanized silica or bis-stearyl-ethylenediamide. With advantages, use is also made of mixtures of different foam inhibitors, for example mixtures of silicones, paraffins or waxes. The foam inhibitors, in particular those containing silicone and/or paraffin, are preferably bound to a granular, water-soluble or dispersible support substance. Particular preference is given here to mixtures of paraffins and bis-stearylethylenediamides.

A cleaning product of the invention for hard surfaces may, in addition, contain ingredients with abrasive action, in particular from the group comprising quartz flours, wood flours, polymer flours, chalks and glass microbeads, and mixtures thereof. Abrasives are present in the cleaning products of the invention preferably at not more than 20% by weight, in particular from 5% by weight to 15% by weight.

Dyes and fragrances are added to washing and cleaning products in order to improve the esthetic appeal of the products and to provide the consumer, in addition to washing and cleaning performance, with a visually and sensorially "typical and unmistakable" product. As perfume oils and/or fragrances it is possible to use individual odorant compounds, for example the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether; the aldehydes include, for example, the linear alkanals having 8-18 carbon atoms, citral, citronellal, citronellyloxyacetaldehyde, cyclamen aldehyde, hydroxycitronellal, lilial and bourgeonal; the ketones include, for example, the ionones, α-isomethylionone and methyl cedryl ketone; the alcohols include anethol, citronellol, eugenol, geraniol, linalool, phenylethyl alcohol, and terpineol; the hydrocarbons include primarily the terpenes such as limonene and pinene. Preference, however, is given to the use of mixtures of different odorants which together produce an appealing fragrance note. Such perfume oils may also contain natural odorant mixtures, as obtainable from plant sources, for example pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orangepeel oil and sandalwood oil. The dye content of detergents and cleaning agents is usually less than 0.01% by weight, while fragrances may make up up to 2% by weight of the overall formulation.

The fragrances may be incorporated directly into the washing and cleaning products; however, it may also be advantageous to apply the fragrances to carriers which enhance the adhesion of the perfume to the material to be cleaned and, by means of slower fragrance release, ensure long-lasting fragrance, in particular of treated textiles. Materials which have become established as such carriers are, for example, cyclodextrins, it being possible, in addition, for the cyclodextrin-perfume complexes also to be coated with further auxiliaries. Another preferred carrier for fragances is the described zeolite X which can also absorb fragrances instead of or in a mixture with surfactants. Preference is therefore given to washing and cleaning products which contain the described zeolite X and fragrances which, preferably, are at least partially absorbed on the zeolite.

Preferred dyes whose selection is by no means difficult for the skilled worker have high storage stability and insensitivity to the other ingredients of the products and to light, and also have no pronounced affinity for textile fibers, so as not to stain them.

To control microorganisms, washing or cleaning products may contain antimicrobial active ingredients. Depending on antimicrobial spectrum and mechanism of action, a distinction is made here between bacteriostatics and bactericides, fungistatics and fungicides, etc. Examples of important substances from these groups are benzalkonium chlorides, alkylarylsulfonates, halophenols and phenylmercury acetate. The terms antimicrobial action and antimicrobial active ingredient have, within the teaching of the invention, the meaning common in the prior art, which is described, for example, by K. H. Wallhäußer in "Praxis der Sterilisation, Desinfektion-Konservierung: Keimidentifizierung-Betriebshygiene" (5th Edition,—Stuttgart; New York: Thieme, 1995), it being possible to use all of the substances having antimicrobial action described there. Suitable antimicrobial active ingredients are preferably selected from the groups of alcohols, amines, aldehydes, antimicrobial acids or their salts, carboxylic esters, acid amides, phenols, phenol derivatives, diphenyls, diphenylalkanes, urea derivatives, oxygen acetals, nitrogen acetals and also oxygen and nitrogen formals, benzamidines, isothioazolines, phthalimide derivatives, pyridine derivatives, antimicrobial surfactant compounds, guanidines, antimicrobial amphoteric compounds, quinolines, 1,2-dibromo-2,4-dicyanobutane, iodo-2-propylbutyl carbamate, iodine, iodophors, peroxo compounds, halogen compounds, and any mixtures of the above.

The antimicrobial active ingredient may be selected from ethanol, n-propanol, isopropanol, 1,3-butanediol, phenoxyethanol, 1,2-propylene glycol, glycerol, undecylenic acid, benzoic acid, salicylic acid, dihydracetic acid, o-phenylphenol, N-methylmorpholinoacetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorohexidine, N-(4-chlorophenyl)-N-(3,4-dichlorophenyl)urea, N,N'-(1,10-decanediyldi-1-pyridinyl-4-ylidene)-bis(1-octanamine) dihydrochloride, N,N'-bis(4-chlorophenyl)-3,1 2-diimino-2,4,11,13-tetra-azatetradecanediimideamide, glucoprotamines, antimicrobial surface-active quaternary compounds, guanidines including the bi- and polyguanidines, such as, for example, 1,6-bis(2-ethylhexylbiguanidohexane) dihydrochloride, 1,6-di-($N_1$,$N_1$'-phenyldiguanido-$N_5$,$N_5$') hexane tetrahydrochloride, 1,6-di-($N_1$,$N_1$'-phenyl-$N_1$,$N_1$'-methyldiguanido-$N_5$,$N_5$')hexane dihydrochloride, 1,6-di-($N_1$,$N_1$'-o-chlorophenyldiguanido-$N_5$,$N_5$ ')hexane dihydrochloride, 1,6-di-($N_1$,$N_1$'-2,6-dichlorophenyl-diguanido-$N_5$,$N_5$')hexane dihydrochloride, 1,6-di-[$N_1$,$N_1$'-beta-(p-methoxyphenyl)diguanido-$N_5$,$N_5$ ' ]hexane dihydrochloride, 1 ,6-di-($N_1$,$N_1$'-alpha-methyl-beta-phenyldiguanido-$N_5$,$N_5$')hexane dihydrochloride, 1 ,6-di-($N_1$,$N_1$'-p-nitrophenyldiguanido-$N_5$,$N_5$')hexane dihydrochloride, omega:omega-di-($N_1$,$N_1$'-phenyl-diguanido-$N_5$,$N_5$')-di-n-propyl ether dihydrochloride, omega:omega'-di-($N_1$,$N_1$'-p-chlorophenyldiguanido-$N_5$, $N_5$')-di-n-propyl ether tetrahydrochloride, 1,6-di-($N_1$,$N_1$'-2, 4-dichlorophenyldiguanido-$N_5$,$N_5$')hexane tetrahydrochloride, 1,6-di-($N_1$,$N_1$'-p-methylphenyldiguanido-$N_5$,$N_5$') hexane dihydrochloride, 1,6-di-($N_1$,$N_1$'-2,4,5-trichlorophenyldiguanido-$N_5$,$N_5$')hexane tetrahydrochloride, 1,6-di-[$N_1$, $N_1$'-alpha-(p-chlorophenyl)ethyldiguanido-$N_5$,$N_5$']hexane dihydrochloride, omega:omega-di-($N_1$,$N_1$'-p-chlorophenyl-diguanido-$N_5$,$N_5$')m-xylene dihydro-chloride, 1,1 2-di-($N_1$, $N_1$'-p-chlorophenyldiguanido-$N_5$,$N_5$')dodecane dihydrochloride, 1,10-di-($N_1$,$N_1$'-phenyldiguanido-$N_5$,$N_5$')decane tetrahydrochloride, 1,1 2-di-($N_1$,$N_1$'-phenyldiguanido-$N_5$, $N_5$' )dodecane tetrahydrochloride, 1,6-di-($N_1$,$N_1$'-o-chlorophenyldiguanido-$N_5$,$N_5$')hexane dihydrochloride, 1,6-di-($N_1$,$N_1$'-o-chlorophenyldiguanido-$N_5$,$N_5$')hexane tetrahydrochloride, ethylenebis(1-tolylbiguanide), ethylenebis(p-tolylbiguanide), ethylenebis(3,5-dimethylphenyl-biguanide), ethylene-bis(p-tert-amylphenylbiguanide), ethylenebis(nonylphenylbiguanide), ethylenebis (phenylbiguanide), ethylenebis(N-butylphenylbiguanide), ethylene-bis(2,5-diethoxyphenylbiguanide), ethylene-bis(2, 4-dimethylphenylbiguanide), ethylenebis(o-diphenylbiguanide), ethylenebis(mixed amyl naphthylbiguanide), N-butylethylenebis(phenylbiguanide), trimethylenebis(o-tolylbiguanide), N-butyltrimethylbis(phenylbiguanide) and the corresponding salts such as acetates, gluconates, hydrochlorides, hydrobromides, citrates, bisulfites, fluorides, polymaleates, N-cocoalkylsarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates, and any mixtures thereof. Also suitable are halogenated xylene and cresol derivatives, such as p-chlorometacresol or p-chlorometaxylene, and natural antimicrobial active ingredients of plant origin (for example from spices or herbs), animal origin and microbial origin. Preference may be given to using antimicrobial surface-active quaternary compounds, a natural antimicrobial active ingredient of plant origin and/or a natural antimicrobial active ingredient of animal origin, most preferably at least one natural antimicrobial active ingredient of plant origin from the group comprising caffeine, theobromine and theophylline and essential oils such as eugenol, thymol and geraniol, and/or at least one natural antimicrobial active ingredient of animal origin from the group comprising enzymes such as milk protein, lysozyme and lactoperoxidase, and/or at least one antimicrobial surface-active quaternary compound having an ammonium, sulfonium, phosphonium, iodonium or arsonium group, peroxo compounds and chlorine compounds. It is also possible to use substances of microbial origin, the "bacteriocines".

The quaternary ammonium compounds (QACs) which are suitable as antimicrobial active ingredients have the general formula $(R^1)(R^2)(R^3)(R^4)N^+X^-$ where $R^1$ to $R^4$ are identical or different $C_1$-$C_{22}$-alkyl radicals, $C_7$-$C_{28}$-aralkyl radicals or heterocyclic radicals, where two, or in the case of an aromatic incorporation such as in pyridine, even three radicals, together with the nitrogen atom, form the heterocycle, for example a pyridinium or imidazolinium compound, and $X^-$ are halide ions, sulfate ions, hydroxide ions or similar anions. For optimal antimicrobial action, at least one of the radicals preferably has a chain length of from 8 to 18, in particular 12 to 16, carbon atoms.

QACs can be prepared by reacting tertiary amines with alkylating agents such as, for example, methyl chloride, benzyl chloride, dimethyl sulfate, dodecyl bromide, or else ethylene oxide. The alkylation of tertiary amines having one long alkyl radical and two methyl groups proceeds particularly readily, and the quaternization of tertiary amines having two long radicals and one methyl group can also be carried out with the aid of methyl chloride under mild conditions. Amines which have three long alkyl radicals or hydroxy-substituted alkyl radicals have low reactivity and are preferably quaternized using dimethyl sulfate.

Examples of suitable QACs are benzalkonium chloride (N-alkyl-N,N-dimethylbenzylammonium chloride, CAS No. 8001-54-5), benzalkone B (m,p-dichlorobenzyldimethyl-C12-alkylammonium chloride, CAS No. 58390-78-6), benzoxonium chloride (benzyldodecylbis(2-hydroxyethyl)ammonium chloride), cetrimonium bromide (N-hexadecyl-N, N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5) and thiazoline iodide (CAS No. 1576448-1), and mixtures thereof. Particularly preferred QACs are the benzalkonium chlorides having $C_8$-$C_{18}$-alkyl radials, in particular $C_{12}$-$C_{14}$-alkylbenzyldimethylammonium chloride.

Benzalkonium halides and/or substituted benzalkonium halides are commercially available, for example, as BARQUAT® ex Lonza, MARQUAT® ex Mason, VARIQUAT® ex Witco/Sherex and HYAMINE® ex Lonza, and BARDAC® ex Lonza. Further commercially available antimicrobial active ingredients are N-(3-chloroallyl)hexaminium chloride such as DOWICIDE® and DOWICIL® ex Dow, benzethonium chloride such as HYAMINE® 1622 ex Rohm & Haas, methylbenzethonium chloride such as HYAMINE® 10× ex Rohm & Haas, cetylpyridinium chloride such as cepacol chloride ex Merrell Labs.

The antimicrobial active ingredients are used in amounts of from 0.0001% by weight to 1% by weight, preferably from 0.001% by weight to 0.8% by weight, particularly preferably from 0.005% by weight to 0.3% by weight, and in particular from 0.01 to 0.2% by weight.

The washing or cleaning products of the invention may contain UV absorbers which attach to the treated textiles and improve the light stability of the fibers and/or the light stability of other formulation constituents. UV absorbers mean organic substances (light protection filters) which are able to absorb ultraviolet radiation and to emit the absorbed energy again in the form of radiation of longer wavelength, for example heat.

Compounds which have these desired properties are, for example, the compounds which are active via radiationless deactivation and derivatives of benzophenone having substituents in position(s) 2 and/or 4. Furthermore, also suitable are substituted benzotriazoles, acrylates which are phenyl-substituted in position 3 (cinnamic acid derivatives, with or without cyano groups in position 2), salicylates, organic Ni complexes and natural substances such as umbelliferone and the endogenous urocanic acid. Of particular importance are biphenyl derivatives and especially stilbene derivatives, as described, for example, in EP 0728749 A and commercially available as TINOSORB® FD or TINOSORB® FR ex Ciba. UV-B absorbers which may be mentioned are: 3-benzylidenecamphor or 3-benzylidenenorcamphor and derivatives thereof, for example 3-(4-methylbenzylidene)camphor, as described in EP 0693471 B1; 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylenes); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives such as, for example, 2,4,6-trianilino-(p-carbo-2'-ethyl-1'-hexyloxy)-1,3,5-triazine and octyltriazone, as described in EP 0818450 A1, or dioctylbutamidotriazones (UVASORB® HEB); propane-1,3-diones such as, for example, 1-(4-tert-butylphenyl)-3-(4'-methoxyphenyl)propane-1,3-dione; ketotricyclo(5.2.1.0)decane derivatives, as described in EP 0694521 B1. Further suitable are 2-phenylbenzimidazole-5-sulfonic acid and its alkali metal, alkaline earth metal, ammonium, alkylammonium, alkanolammonium and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters may of course also be used in mixtures. In addition to said soluble substances, insoluble light protection pigments, namely finely dispersed, preferably nanoized, metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are already used in the form of the pigments for skin-care and skin-protective emulsions and decorative cosmetics. The particles here should have an average diameter of less than 100 nm, preferably between 5 and 50 nm, and in particular between 15 and 30 nm. They can have a spherical shape, but it is also possible to use particles which have an ellipsoidal shape or a shape deviating in some other way from the spherical form. The pigments may also be surface-treated, i.e. hydrophilicized or hydrophobicized. Typical examples are coated titanium dioxides such as, for example, titanium dioxide T 805 (Degussa) or Eusolex® T2000 (Merck); suitable hydrophobic coating agents are here preferably silicones and, particularly preferably, trialkoxyoctylsilanes or simethicones. Preference is given to using micronized zinc oxide. Further suitable UV light protection filters can be found in the review by P. Finkel in SÖFW-Journal 122 (1996), p. 543.

The UV absorbers are usually used in amounts of from 0.01% by weight to 5% by weight, preferably from 0.03% by weight to 1% by weight.

The ingredients usual for washing and cleaning products generally also include detersive and, respectively, cleaning-active enzymes.

Thus, washing or cleaning products which are also characterized by further enzymes in addition to a protein, protein fragment, fusion protein or derivative of the invention described above are preferred embodiments of the present invention. These include in particular other proteases, amylases, cellulases, hemicellulases such as for example β-glucanases, oxidoreductases such as, for example, laccases, cutinases, and/or lipases, but also esterases and all other enzymes described in the prior art for this area of use.

Enzymes such as proteases, amylases, lipases or cellulases have been used for decades as active components in washing and cleaning products. Their particular contribution to the washing and, respectively, cleaning performance of the agent in question is, in the case of protease, the ability to break down proteinaceous soilings, in the case of amylase, the breaking-down of starch-containing soilings, and, in the case of lipase, fat-cleaving activity. Cellulases are preferably used in washing products, in particular due to their contribution to the secondary washing performance of a washing product and due to their fiber action on textiles, in addition to their soil-removing, i.e. primary washing and cleaning performance. The particular hydrolysis products are attacked, dissolved, emulsified or suspended by the other washing or cleaning product components or are, due to their greater solubility, washed away with the wash liquor, advantageously resulting in synergistic effects between the enzymes and the other components.

Proteases can exert an effect on natural fibers, in particular on wool or silk, which is comparable to the contribution by cellulase to the secondary washing performance of a washing product. Due to their action on the surface structure of such fabrics, they can exert a smoothing influence on the material and thereby counteract felting.

Other enzymes extend the cleaning performance of appropriate products by their in each case specific enzyme performance. Examples of these include hemicellulases such as, for example, β-glucanases (WO 99/06515 and WO 99/06516), oxidoreductases such as, for example, laccases (WO 00/39306) or pectin-dissolving enzymes (WO 00/42145) which are used, in particular, in special washing products.

Enzymes suitable for use in washing or cleaning products of the invention are primarily those from microorganisms such as bacteria or fungi. They are obtained from suitable microorganisms in a manner known per se by means of fermentation processes which are described, for example, in German Laid-Open Specifications DE 1940488, and DE 2121397, the US patents U.S. Pat. Nos. 3,623,957, 4,264,738, European patent application EP 006638 and international patent application WO 91/02792.

Particularly during storage, a protein of the invention and/or other proteins present may be protected by stabilizers from, for example, denaturing, decay or inactivation, for example by physical influences, oxidation or proteolytic cleavage. This applies to all products of the invention, in particular washing and cleaning products.

One group of stabilizers is of reversible protease inhibitors which dissociate off when diluting the product in the wash liquor. Benzamidine hydrochloride and leupeptin are established for this purpose. Frequently, borax, boric acids, boronic acids or salts or esters thereof are used, including especially derivatives with aromatic groups, for example, according to WO 95/12655, ortho-substituted, according to WO 92/19707, meta-substituted, and, according to U.S. Pat. No. 5,972,873, para-substituted phenylboronic acids, or salts or esters thereof. The applications WO 98/13460 and EP 583534 disclose peptide aldehydes, i.e. oligopeptides with reduced C terminus, specifically those of 2-50 monomers, for the reversible inhibition of washing and cleaning product proteases. The peptidic reversible protease inhibitors include, inter alia, ovomucoid (WO 93/00418). For example, the application WO 00/01826 discloses specific reversible peptide inhibitors of the protease subtilisin for use in protease-containing agents, and WO 00/01831 discloses corresponding fusion proteins of protease and inhibitor. Further enzyme stabilizers are amino alcohols such as mono-, di-, triethanol- and -propanolamine and mixtures thereof, aliphatic carboxylic acids up to $C_{12}$, as disclosed, for example, by the applications EP 0378261 and WO 97/05227, such as succinic acid, other dicarboxylic acids or salts of said acids. The application DE 19650537 discloses end-group-capped fatty amide alkoxylates for this purpose. As disclosed in WO 97/18287, particular organic acids used as builders are capable of additionally stabilizing a contained enzyme.

Lower aliphatic alcohols, but especially polyols such as, for example, glycerol, ethylene glycol, propylene glycol or sorbitol, are other frequently used enzyme stabilizers. Calcium salts are also used, such as, for example, calcium acetate or the calcium formate disclosed for this purpose in EP 028865, and magnesium salts, for example according to European application EP 378262.

Polyamide oligomers (WO 99/43780) or polymeric compounds such as lignin (WO 97/00932), water-soluble vinyl copolymers (EP 828762) or, as disclosed in EP 702712, cellulose ethers, acrylic polymers and/or polyamides stabilize the enzyme preparation inter alia against physical influences or pH fluctuations. Polyamine N-oxide-containing polymers (EP 587550 and EP 581751) simultaneously act as enzyme stabilizers and as color transfer inhibitors. Other polymeric stabilizers are the linear $C_8$-$C_{18}$ polyoxyalkylenes disclosed, in addition to other components, in WO 97/05227. As in the applications WO 97/43377 and WO 98/45396, alkylpolyglycosides could stabilize the enzymic components of the product of the invention and even increase their performance. Crosslinked N-containing compounds, as disclosed in WO 98/17764, fulfill a double function as soil release agents and as enzyme stabilizers. Hydrophobic, nonionic polymer acts in a mixture together with other stabilizers, according to the application WO 97/32958, in a stabilizing manner on a cellulase so that these or similar components may also be suitable for the enzyme essential to the invention.

As disclosed inter alia in EP 780466, reducing agents and antioxidants increase the stability of the enzymes against oxidative decay. Sulfur-containing reducing agents are disclosed, for example, in EP 080748 and EP 080223. Other examples are sodium sulfite (EP 533239) and reducing sugars (EP 656058).

Frequently used are also combinations of stabilizers, for example of polyols, boric acid and/or borax in the application WO 96/31589, the combination of boric acid or borate, reducing salts and succinic acid or other dicarboxylic acids in the application EP 126505 or the combination of boric acid or borate with polyols or polyamino compounds and with reducing salts, as disclosed in the application EP 080223. According to WO 98/13462, the action of peptide-aldehyde stabilizers is increased by combination with boric acid and/or boric acid derivatives and polyols and, according to WO 98/13459, still further enhanced by the additional use of calcium ions.

Products containing stabilized enzyme activities are preferred embodiments of the present invention. Particular preference is given to those containing enzymes stabilized in a plurality of the ways indicated.

Since products of the invention can be provided in any conceivable form, enzymes or proteins of the invention in any formulations appropriate for addition to the particular products are respective embodiments of the present invention. Examples thereof include liquid formulations, solid granules or capsules.

The encapsulated form is a way of protecting the enzymes or other ingredients against other components such as, for example, bleaches, or of making possible a controlled release. Depending on their size, said capsules are divided into milli-, micro- and nanocapsules, microcapsules being particularly preferred for enzymes. Such capsules are disclosed, for example, in the patent applications WO 97/24177 and DE 19918267. A possible encapsulation method is to encapsulate the proteins, starting from a mixture of the protein solution with a solution or suspension of starch or a starch derivative, in this substance. The application WO 01/38471 describes such an encapsulation method.

In the case of solid products, the proteins may be used, for example, in dried, granulated and/or encapsulated form. They may be added separately, i.e. as a separate phase, or together with other components in the same phase, with or without compaction. If microencapsulated enzymes are to be processed in solid form, it is possible to remove the water from the aqueous solutions resulting from the work-up by using methods known in the prior art, such as spray drying, removing by centrifugation or resolubilizing. The particles obtained in this way are usually between 50 and 200 µm in size.

It is possible to add to liquid, gel-like or paste-like products of the invention the enzymes and also the protein of the invention, starting from protein recovery carried out according to the prior art, and preparation in a concentrated aqueous or nonaqueous solution, suspension or emulsion, but also in gel form or encapsulated or as dried powder. Such washing or cleaning products of the invention are usually prepared by simply mixing the ingredients which may be introduced as solids or as solution into an automated mixer.

Apart from the primary washing performance, the proteases present in washing products may further fulfill the function of activating, or, after an appropriate period of action, inactivating other enzymic components by proteolytic cleavage, as has been disclosed, for example, in the applications WO 94/29426 or EP 747471. Comparable regulatory functions are also possible via the protein of the invention. Another embodiment of the present invention relates to those products containing capsules of protease-sensitive material, which capsules are hydrolyzed, for example, by proteins of the invention at the intended time and release their contents. A comparable effect may also be achieved in other multi-phase products.

Products for the treatment of textile raw materials or for textile care, which are characterized in that they comprise, alone or in addition to other active ingredients, any of the proteins, protein fragments, fusion proteins or derivatives of the invention described above, in particular for fibers or textiles containing natural components and very particularly for those containing wool or silk are a further embodiment of the invention.

Natural fibers in particular, such as wool or silk, for example, are distinguished by a characteristic, microscopic surface structure. Said surface structure can, in the long term, result in undesired effects such as, for example, felting, as discussed by way of example for wool in the prior article by R. Breier in *Melliand Textilberichte* from 4.1.2000 (p. 263). In order to avoid such effects, the natural raw materials are treated with agents of the invention which contribute, for example, to smoothing the flaked surface structure based on protein structures and thereby counteract felting.

In one preferred embodiment, the product containing a protease of the invention is designed in such a way that it can be used regularly as a care agent, for example by adding it to the washing process, applying it after washing or independently of the washing. The desired effect is to obtain a smooth surface structure of the textile over a long duration and/or to prevent and/or reduce damage to the fabric.

Methods for machine cleaning textiles or hard surfaces, which methods are characterized in that in at least one of the method steps a protein, protein fragment, fusion protein or derivative of the invention described above becomes active, in particular in an amount of from 40 µg to 4 g, preferably from 50 µg to 3 g, particularly preferably from 100 µg to 2 g and very particularly preferably from 200 µg to 1 g per application, are a separate subject matter of the invention.

These include both manual and machine methods, with preference for machine methods because they can be controlled more precisely in relation to, for example, amounts employed and times of action.

Methods for cleaning of textiles are generally distinguished by several method steps comprising applying various cleaning-active substances to the material to be cleaned and, after the time of action, washing them off, or by the material to be cleaned being treated in any other way with a detergent or a solution of said agent. The same applies to methods for cleaning of any other materials as textiles which are classified under the term hard surfaces. It is possible to add proteins of the invention to at least one of the method steps of all conceivable washing or cleaning methods, which methods then become embodiments of the present invention.

Since preferred enzymes of the invention already by nature possess a protein-dissolving activity and also exhibit said activity in media which otherwise have no cleaning power, such as, for example, in straight buffer, an individual partial step of such a method for machine cleaning of textiles may consist of applying, if desired in addition to stabilizing compounds, salts or buffer substances, an enzyme of the invention as single cleaning-active component. This is a particularly preferred embodiment of the present invention.

In a further preferred embodiment of such methods, the relevant enzymes of the invention are provided in one of the formulations mentioned above for products of the invention, preferably washing or cleaning products of the invention.

Methods for the treatment of textile raw materials or for textile care, which methods are characterized in that in at least one of the method steps a protein, protein fragment, fusion protein or derivative of the invention described above becomes active, are preferred embodiments of this subject matter of the invention, in particular for textile raw materials, fibers or textiles containing natural components and very particularly for those containing wool or silk.

They may be, for example, methods in which materials are prepared for use in textiles, for example for anti-felt finishing, or, for example, methods which add a care component to the cleaning of worn textiles. Due to the above-described action of proteases on natural, protein-containing raw materials, particular embodiments comprise methods for treating textile raw materials, fibers or textiles containing natural components, in particular containing wool or silk.

The use of a protein, protein fragment, fusion protein or derivative of the invention described above for cleaning textiles or hard surfaces is a separate subject matter of the invention.

The concentration ranges listed above preferably apply for this use.

Proteins of the invention may be used, in particular according to the above-described properties and the above-described methods, in order to remove proteinaceous soilings from textiles or from hard surfaces. Embodiments are represented for example by handwashing or manual removal of spots from textiles or from hard surfaces or the use in connection with a machine method.

In a preferred embodiment of this use, the relevant enzymes of the invention are provided in one of the formulations mentioned above for products of the invention, preferably washing or cleaning products.

The use of a protein, protein fragment, fusion protein or derivative of the invention described above for activating or deactivating ingredients of washing or cleaning products is a further embodiment of this subject matter of the invention.

Protein components of washing or cleaning products, as is known, can be inactivated by the action of a protease. The present invention relates to specifically using this otherwise rather undesired effect. It is likewise possible, as described above, that proteolysis actually activates another component, for example if said component is a hybrid protein of the actual enzyme and the corresponding inhibitor, as disclosed, for example, in the application WO 00/01831. Another example of a regulation of this kind is one in which an active component, in order to protect or control its activity, has been encapsulated in a material susceptible to proteolytic attack. Proteins of the invention can thus be used for inactivation reactions, activation reactions or release reactions, in particular in multiphase products.

Despite their diversity, all other technical methods, uses and corresponding agents outside the problem of washing and cleaning are combined into one subject matter of the invention hereinbelow, as long as they are characterized by a protein of the invention. This compilation is not to be understood as an exclusive listing, but lists the most important, currently discernible possible uses of proteases of the invention. Indicators of further possible uses which are likewise included are provided for example by the manual "Industrial enzymes and their applications" by H. Uhlig, published by Wiley, New York, 1998. If other technical fields prove able to be developed further by using proteases of the invention, then said fields are included within the scope of protection of the present invention.

One embodiment of this subject matter of the invention is represented by the use of a protein, protein fragment, fusion protein or derivative of the invention described above for biochemically analyzing or for synthesizing low molecular weight compounds or of proteins.

This use preferably takes place within the scope of corresponding products or methods. According to the invention and according to Rompp, "Lexikon Chemie" (Version 2.0, Stuttgart/New York: Georg Thieme Verlag, 1999), enzymic analysis means any biochemical analysis which uses specific enzymes or substrates in order to determine, on the one hand, the identity or concentration of substrates or, on the other hand, the identity or activity of enzymes. Areas of application are any areas of work related to biochemistry, in particular molecular biology and protein chemistry. This use preferably takes place within the scope of an enzymatic analysis method. A preferred embodiment of this subject matter of the invention is the use for determining the terminal groups in a sequence analysis.

The use of a protein, protein fragment, fusion protein or derivative of the invention described above for preparing, purifying or synthesizing natural substances or biological valuable substances is subject matter of the invention.

This use preferably takes place within the scope of corresponding products or methods. Thus, it may be necessary, for example, in the course of purifying natural substances or biological valuable substances, to remove from said substances protein contaminations, examples of which are low molecular weight compounds, any cellular constituents or storage substances or proteins. This can be carried out both on the laboratory scale and the industrial scale, for example after biotechnological production of a valuable substance.

A proteolytic enzyme of the invention is used for the synthesis of proteins or other low molecular weight chemical compounds by reversing the reaction which they catalyze by nature, for example when it is intended to link protein fragments to one another or to bind amino acids to a compound which is not predominantly composed of protein. Possible uses of this kind are possible, for example, following the application EP 380362.

A further embodiment of this subject matter of the invention is represented by the use of a protein, protein fragment, fusion protein or derivative of the invention described above for the treatment of natural raw materials, in particular for the treatment of surfaces, very particularly in a method for the treatment of leather.

This use preferably takes place within the scope of corresponding products or methods. It is necessary for example when protein contaminations are to be removed from natural raw materials. By this are meant primarily raw materials to be obtained non-microbiologically, for example from agriculture, but also substances produced biotechnologically by fermentation, such as, for example, antibiotics.

A preferred embodiment is the use for the treatment of surfaces, and very particularly in a method for the treatment of the economically important raw material leather. Thus, water-soluble proteins are removed from the hide material with the aid of proteolytic enzymes during the tanning process, in particular in the step of alkaline steep (Römpp, "Lexikon Chemie", Version 2.0, Stuttgart/New York: Georg Thieme Verlag, 1999). Proteases of the invention are suitable for this, in particular under alkaline conditions and/or in the presence of denaturing agents.

The use of a protein, protein fragment, fusion protein or derivative of the invention described above for the obtainment or treatment of raw materials or intermediates in the manufacture of textiles, in particular for removing protective layers from fabrics, is another embodiment of this subject matter of the invention.

This use preferably takes place within the scope of corresponding products or methods. An example of the obtainment or treatment of raw materials or intermediates in the manufacture of textiles is the processing of cotton from which capsule components need to be removed in a process referred to as sizing; another example is the treatment of wool; the processing of raw silk is also similar. Enzymic methods, or uses, are superior to comparable chemical methods, in particular with respect to their environmental compatibility.

In a preferred embodiment, proteins of the invention are used for removing protective layers from textiles, in particular from intermediate products or valuable substances, or smoothing their surface, before further treatment in a subsequent processing step.

A further embodiment of this subject matter of the invention is represented by the use of a protein, protein fragment, fusion protein or derivative of the invention described above for the treatment of textile raw materials or for textile care, in particular for the treatment of wool or silk or wool- or silk-containing textile blends.

This use preferably takes place within the scope of corresponding products or methods. In accordance with what has been stated above, the relevant textile raw materials are freed of contaminations by the protease; in addition, a material consisting at least partly of protein benefits from the surface-smoothing and care properties of the proteolytic enzyme. For this reason, the use for the care of the relevant materials is also included. The surface treatment of wool or silk or wool- or silk-containing textile blends is therefore claimed in particular. This applies both to the production of such textiles and to the care during usage, for example in connection with the cleaning of textiles (see above).

The use of a protein, protein fragment, fusion protein or derivative of the invention described above for the treatment of photographic films, in particular for removing gelatin-containing or similar protective layers, is another embodiment of this subject matter of the invention.

This use preferably takes place within the scope of corresponding products or methods. Films such as, for example, X-ray films, are coated with such protective layers, in particular those made of silver salt-containing gelatin emulsions. These layers need to be removed from the backing material after exposure. For this, proteases of the invention may be used, in particular under alkaline or slightly denaturing reaction conditions.

The use of a protein, protein fragment, fusion protein or derivative of the invention described above for preparing food or animal feed is another embodiment of this subject matter of the invention.

This use preferably takes place within the scope of corresponding products or methods. Thus proteases have been used for the preparation of food from time immemorial. An example of this is the use of rennet for the maturing process of cheese or other milk products. A protein of the invention may be added to or be used to completely carry out such processes. Carbohydrate-rich food or food raw materials for non-nutritional purposes, such as, for example, cereal flour or dextrin, may also be treated with appropriate proteases in order to remove accompanying proteins from them. A protease of the invention is suitable for those applications, too, in particular if they are to be carried out under alkaline or slightly denaturing conditions.

This applies accordingly for the preparation of animal feed. In addition to a complete removal of proteins, it may also be of interest here to treat the proteinaceous starting substances or substance mixtures with proteases only for a short time in order to render them more readily digestible for domestic animals. Such a treatment can also be employed for example for producing media ingredients for example for fermenting microorganisms.

In another embodiment of this subject matter of the invention, the proteins of the invention described above are used for cosmetic purposes.

Thus, cosmetics containing a protein, protein fragment, fusion protein or derivative of the invention described above, or cosmetic methods incorporating a protein, protein fragment, fusion protein or derivative of the invention described above, or the use of a protein, protein fragment, fusion protein or derivative of the invention described above for cosmetic purposes, in particular within the framework of corresponding methods or in corresponding products, are claimed.

Since proteases also play a crucial part in the desquamation of human skin (T. Egelrud et al., *Acta Derm. Venerol.*, volume 71 (1991), pp. 471-747), proteases are accordingly also used as bioactive components in skincare products in order to support degradation of the desmosome structures increasingly present in dry skin, for example according to the applications WO 95/07688 and WO 99/18219. WO 97/07770, for example, describes the use of subtilisin proteases for cosmetic purposes. Proteases of the invention, in particular those whose activity is controlled, for example, after mutagenesis or due to addition of appropriate substances interacting with them, are also suitable as active components in skin- or hair-cleaning compositions or care compositions. Particular preference is given to those preparations of said enzymes, which, as described above, are stabilized, for example by coupling to macromolecular supports (compare U.S. Pat. No. 5,230,891), and/or are derivatized by point mutations at highly allergenic positions so that their compatibility with human skin is increased.

Accordingly, the use of proteolytic enzymes of this kind for cosmetic purposes, in particular in appropriate products such as, for example, shampoos, soaps or washing lotions or in care compositions provided, for example, in the form of creams, is also included in this subject matter of the invention. The use in a peeling medicament, or its preparation, is also included in this claim.

EXAMPLES

All molecular-biological working steps follow standard methods as indicated, for example, in the manual by Fritsch, Sambrook and Maniatis "Molecular cloning: a laboratory manual", Cold Spring Harbour Laboratory Press, New York, 1989, or comparable relevant works. Enzymes and kits were used in accordance with the instructions of the respective manufacturer.

Example 1

Isolation and Identification of a Bacterial Strain With Proteolytic Activity 0.1 g of a soil sample were suspended in 1 ml of sterile 0.9% strength NaCl solution and plated out on agar plates containing milk powder (1.5% agar, 0.5% NaCl, 0.1% $K_2HPO_4$, 0.1% yeast extract, 2% peptone (from ICN, Eschwede, Cat. No. 104808), 1% milk powder (skim milk; from Difco, Heidelberg, Cat. No. 232100), pH 10). After incubation at 30° C. for 72 hours, colonies with clarification zones were evident in the milky agar. Single colonies were removed therefrom and cultivated in Horikoshi medium (0.1% $K_2HPO_4$, 0.5% yeast extract, 1% peptone, 0.02% $MgSO_4$, 0.3% $Na_2CO_3$, pH 9) in Erlenmeyer flasks at 37° C., shaking at 200 rpm.

One of these clones was deposited on Mar. 1, 2001, at the Deutsche Sammlung von Mikroorganismen und Zellkulturen GmbH, Mascheroder Weg 1b, 38124 Brunswick (DSMZ). Its designation there is ID 01-192, and the accession number is DSM 14391. The standard information on the features of this biological material, as determined on deposition by the DSMZ on Apr. 19, 2001, is compiled in table 1 below.

TABLE 1

Microbiological properties of *Bacillus gibsonii* (DSM 14391). (Determined by the DSMZ on Apr. 19, 2001.)

| Property | Result |
|---|---|
| Cell form | Rods |
| Width [µm] | 0.8-1.2 |
| Length [µm] | 2.0-3.0 |
| Spores | positive, oval |
| Sporangium swollen | negative |
| Growth, CASO, pH 7 | positive |
| Growth, DSM Med. 31, pH 9.7 | positive |
| Anaerobic growth | negative |
| VP reaction | negative |
| pH in VP medium | 6.4 |
| Maximum temperature | |
| Growth positive at ° C. | 30 |
| Growth negative at ° C. | 40 |
| Growth in | |
| medium pH 5.7 | negative |
| NaCl   2% | positive |
| 5% | positive |
| 7% | positive |
| 10% | positive |
| lysozyme medium | negative |
| Acid from (ASS) | |
| D-glucose | positive, weak |
| L-arabinose | negative |
| D-xylose | negative |
| D-mannitol | positive, weak |
| D-fructose | positive, weak |
| Gas from glucose | negative |
| Hydrolysis of | |
| starch | negative |
| gelatin | positive, weak |
| Tween 80 | negative |
| esculin | negative |
| Utilization of | |
| citrate (Koser) | positive, weak |
| propionate | negative |
| $NO_2$ from $NO_3$ | positive |
| Phenylalanine deaminase | negative |
| Arginine dihydrolase | negative |
| Alkaline tests: | |
| 2% to 12% NaCl | positive |
| Tween 40 | negative |
| Tween 60 | negative |
| Tween 80 | negative |
| Pattern of cellular fatty acids | typical of genus *Bacillus* |
| Partial sequencing of the 16S rDNA | 99.2% similarity to *B. gibsonii* |

Example 2

Cloning and Sequencing of the Mature Protease

Chromosomal DNA from *Bacillus gibsonii* (DSM 14391) was prepared by standard methods, treated with the restriction enzyme Sau 3A, and the resulting fragments were cloned into the vector pAWA22. This is an expression vector derived from pBC16 for use in *bacillus* species (Bernhard et al. (1978), *J. Bacteriol.*, Volume 133 (2), pp. 897-903). This vector was transformed into the protease-negative host strain *Bacillus subtilis* DB 104 (Kawamura and Doi (1984), *J. Bacteriol.*, Volume 160 (1), pp. 442-444.

The transformants were initially regenerated on DM3 medium (8 g/l agar, 0.5 M succinic acid, 3.5 g/l K$_2$HPO$_4$, 1.5 g/l KH$_2$PO$_4$, 20 mM MgCl$_2$, 5 g/l casiamino acids, 5 g/l yeast extract, 6 g/l glucose, 0.1 g/l BSA) and then transferred to TBY skim milk plates (10 g/l peptone, 10 g/l milk powder (see above), 5 g/l yeast, 5 g/l NaCl, 15 g/l agar). Clones with proteolytic activity were identified from their zones of lysis. One of the resulting clones with proteolytic activity (p/TII-5) was selected, and its plasmid was isolated and the insert was sequenced by standard methods.

The insert approx. 3.4 kb in size contained an open reading frame of about 1 kb. The sequence thereof is indicated in the sequence listing under the heading SEQ ID No. 1. It comprises 1152 bp. The amino acid sequence derived therefrom comprises 383 amino acids, followed by a stop codon. It is indicated in the sequence listing under SEQ ID No. 2. The first 114 amino acids thereof are probably not present in the mature protein, so that the mature protein is envisaged to have a length of 269 amino acids.

These sequences were compared in August 2001 with the protease sequences obtainable from the generally accessible databases Swiss-Prot (Geneva Bioinformatics (GeneBio) S.A., Geneva, Switzerland) and GenBank (National Center for Biotechnology Information NCBI, National Institutes of Health, Bethesda, Md., USA). The most similar enzymes identified thereby are those summarized in table 2 below.

TABLE 2

Homology of the alkaline protease from *Bacillus gibsonii* (DSM 14391) to the most similar and further representative proteins.

| Enzyme | Organism | ID | Ident. DNA | Ident. propre. | Ident. mat. prot. |
|---|---|---|---|---|---|
| Subtilisin P92 | *Bacillus alkalophilus* | ELYA_BACAO | 62 | 66 | 78 |
| Subtilisin 309 (Savinase ®) | *Bacillus lentus* | SUBS_BACLE | n. | n. | 78 |
| *B. lentus* alkaline protease | *Bacillus lentus* DSM 5483 | SUBB_BACLE | n. | n. | 77 |
| Subtilisin *Sendai* | *Bacillus Sendai* | Q45522 | 65 | 64 | 77 |
| Alkaline elastase | *Bacillus* Ya-B | ELYA_BACSP | 66 | 66 | 76 |
| Subtilisin AprQ | *Bacillus* sp. | Q45523 | 56 | 50 | 62 |
| Subtilisin AprN | *Bacillus subtilis* var. natto | SUBN_BACNA | 55 | 44 | 55 |
| Subtilisin Novo BPN' | *Bacillus amyloliquefaciens* | SUBT_BACAM | n. | 45 | 55 |
| Subtilisin Carlsberg | *Bacillus licheniformis* | SUBT_BACLI | 54 | 44 | 55 |
| Subtilisin | *Bacillus pumilus* | SUBT_BACPU | n. | n. | 54 |
| Subtilisin | *Bacillus amylosacchariticus* | SUBT_BACSA | 54 | 43 | 54 |
| Subtilisin J | *Geobacillus stearothermophilus* | SUBT_BACST | 54 | 43 | 54 |
| Subtilisin E | *Bacillus subtilis* | SUBT_BACSU | 54 | 43 | 54 |

The meanings therein are:
ID    The entry numbers in the databases Genbank and Swiss-Prot;
Ident. DNA    % identity at the DNA level;
Ident. propre.    Identity at the amino acid level, based on the propreprotein, in %;
Ident. mat. prot.    Identity at the amino acid level, based on the mature protein, in %,
n.    not indicated in the databases.

The amino acid sequences of these proteases are also compared with one another in the alignment in FIG. 1.

Example 3

Purification and Characterization of the Alkaline Protease 100 ml of Horikoshi medium (see above) were added to a 500 ml Erlenmeyer flask, inoculated with one colony of the bacillus strain transformed as in example 2, and cultivated at 37° C. for 72 h until the stationary phase of growth was reached.

It was possible to isolate a single proteolytic enzyme from the supernatant of this culture by the following purification steps: dialysis of the supernatant against 20 mM HEPES/NaOH buffer, pH 7.6; negative anion exchange chromatography on Q-Sepharose® (from Pharmacia-Amersham Biotech, Sweden); cation exchange chromatography of the breakthrough on S-Sepharose® (from Pharmacia-Amersham) eluting with a gradient buffer of HEPES/NaOH, 0-1 M NaCl, pH 7.6. The protease eluted at 0.2 M NaCl and was then concentrated by cation exchange chromatography on Resource So (from Pharmacia-Amersham) and HEPES/NaOH (pH 7.6) as eluent.

A protein which was pure according to SDS gel electrophoresis and Coomassie staining was obtained in this way.

Example 4

SDS Polyacrylamide Gel Electrophoresis and Isoelectric Focusing

The alkaline protease from *B. gibsonii* (DSM 14391) obtained as in example 2 and 3 shows in denaturing SDS polyacrylamide gel electrophoresis in the PHAST® system supplied by Pharmacia-Amersham Biotech, Sweden, a molecular weight of 26 kD.

According to isoelectric focusing, likewise in the PHAST® system supplied by Pharmacia-Amersham Biotech, the isoelectric point of the alkaline protease from *B. gibsonii* (DSM 14391) is 11.

Example 5

Enzymatic Properties

Specific Activity

The specific activity of the alkaline protease from *B. gibsonii* (DSM 14391) purified as in example 2 and 3 was measured using the substrate Suc-Ala-Ala-Pro-Phe-p-nitroanilide (SEQ ID NO: 17) (AAPF; from Bachem Biochemica GmbH, Heidelberg). It showed an activity of 21 U/mg on incubation at pH 8.6 and 25° C. for 5 minutes. In this case, 1 U is equivalent to 1 µmol of cleaved substrate per minute.

pH Dependence

The pH profile of the alkaline protease from *Bacillus gibsonii* (DSM 14391) was recorded over a pH range of 6-12. For this purpose, activities were measured with casein as substrate at 50° C. for each integral pH value. According to this, the pH optimum is at pH 11. The activity remaining after incubation at 50° C. for 15 minutes is 2% at pH 12, 14% at pH 6 and 70% at pH 9.

Example 6

Contribution to the Washing Performance

Textiles which had been soiled in a standardized manner and obtained from the Eidgenössische Material-Prüfungs- und -Versuchsanstalt, St. Gallen, Switzerland (EMPA) or the Wäschereiforschungsanstalt, Krefeld, Germany, were used for this example. The following soilings and textiles were used: A (blood/milk/ink on cotton), B (blood/milk/ink on a polyester-cotton blend), C (blood on cotton) and D (egg/soot on cotton).

This test material was used to test the washing performances of various washing product formulations, using a launderometer. For this purpose, the liquor ratio was set in each case to 1:12, and washing was carried out at a temperature of 40° C. for 30 min. The dosage was 5.88 g of the particular product per l of wash liquor. The water hardness was 16° German hardness.

The control washing product used was a basic washing product formulation of the following composition (all values in percent by weight): 4% linear alkylbenzenesulfonate (sodium salt), 4% $C_{12}$-$C_{18}$-fatty alcohol sulfate (sodium salt), 5.5% $C_{12}$-$C_{18}$-fatty alcohol with 7 EO, 1% sodium soap, 11% sodium carbonate, 2.5% amorphous sodium disilicate, 20% sodium perborate tetrahydrate, 5.5% TAED, 25% zeolite A, 4.5% polycarboxylate, 0.5% phosphonate, 2.5% foam inhibitor granules, 5% sodium sulfate, rest: water, optical brighteners, salts. Said formulation was admixed for the different series of experiments with the following proteases in such a way that in each case a final concentration of 2.250 PE of proteolytic activity per l of wash liquor was obtained: *B. lentus* alkaline protease F49 (WO 95/23221; manufacturer: Biozym, Kundl, Austria), Savinasee (Novozymes A/S, Bagsvaerd, Denmark) and the protease of the invention from *B. gibsonii* (DSM 14391).

After washing, the degree of whiteness of the washed textiles was measured in comparison to that of barium sulfate, which had been normalized to 100%. The measurement was carried out in a Datacolor SF500-2 spectrometer at 460 nm (UV blocking filter 3), 30 mm diaphragm, without gloss, D65 illuminant, 10°, d/8°. table 3 below summarizes the results obtained as percent reflectance, i.e. as percentages in comparison with barium sulfate together with the respective starting values. The averages of in each case 4 measurements are listed. They allow an immediate conclusion to be drawn about the contribution of the enzyme present on the washing performance of the product used.

TABLE 3

| Basic washing product with | A | B | C | D |
|---|---|---|---|---|
| starting value | 14.3 | 11.8 | 19.9 | 28.9 |
| Control without protease | 22.2 | 14.7 | 67.9 | 50.3 |
| Protease of the invention from *B. gibsonii* (DSM 14391) | 37.9 | 37.9 | 74.5 | 72.5 |
| *B. lentus* alkaline protease F49 | 30.2 | 25.2 | 70.8 | 72.8 |
| Savinase ® | 32.1 | 29.1 | 68.8 | 54.9 |
| standard deviation | 1.1 | 1.2 | 0.5 | 0.9 |

The data show that the protease of the invention from *B. gibsonii* (DSM 14391) exhibits distinctly better performance than the established proteases *B. lentus* alkaline protease F49 and Savinase®, or at least approaches them, for all soilings tested.

Example 7

Contribution to the Cleaning Performance When the Activity Employed is Low

Vessels with hard, smooth surfaces were contacted in a standardized way with soft-boiled egg (E and F), and with egg/milk (G and H) and washed with commercially available domestic dishwashing machines. Samples E and G were washed in each case at 45° C. with the normal program of the Miele® G 676 type dishwasher, and samples F and H were washed at 55° C. with the normal program of the Bosch® SGS 4002 type dishwasher. 20 g of dishwashing agent were used in each case per dishwashing run. The water hardness was 16° German hardness.

The dishwashing agent used had the following basic formulation (all values in each case in percent by weight): 55% sodium tripolyphosphate (calculated as anhydrous), 4% amorphous sodium disilicate (calculated as anhydrous), 22% sodium carbonate, 9% sodium perborate, 2% TAED, 2% nonionic surfactant, rest: water, dyes, perfume. This basic formulation was admixed for the various experiments, with identical activities, with the various proteases, *B. lentus* alkaline protease F49, Properase® and the protease of *Bacillus gibsonii* (DSM 14391) of the invention, in such a way that in each case an activity of 10 000 PE per dishwashing run was obtained. This corresponded in each case to approx. 0.1 mg of protease protein per g of cleaning product concentrate.

After washing, the removal of the soilings was determined gravimetrically in percent. For this purpose, the difference between the weight of the soiled and then rinsed vessel and the starting weight of said vessel was related to the weight difference of the unwashed vessel to the starting weight. This relation can be regarded as percent removal. The results obtained are summarized in Table 4 below which lists the averages of in each case 8 measurements. They allow an immediate conclusion to be drawn about the contribution of the enzyme present to the washing performance of the product used.

TABLE 4

| Basic dishwashing agent with | E | F | G | H |
|---|---|---|---|---|
| Protease of the invention from *Bacillus. gibsonii* (DSM 14391) | 32.6 | 38.6 | 62.2 | 58.0 |
| *B. lentus* alkaline protease F49 | 26.0 | 38.8 | 30.5 | 51.0 |
| Properase ® | 15.7 | 21.8 | 19.0 | 28.4 |

These results show that the performance of the *Bacillus gibsonii* (DSM 14391) protease of the invention, in machine dishwashing agents is better than or at least equal to that of the other proteases tested; and this even at a comparatively low activity used.

Example 8

Contribution to the Cleaning Performance When the Activity Employed is Higher

Vessels were soiled in a standardized way with soft-boiled egg (I) egg/milk (J) and milk (K) and washed in the same way using the same cleaning product formulations in each case at 45° C. with the normal program of the Miele® G676 type dishwasher. The only difference was that 20 000 PE of the respective proteases were employed in each case. This corresponded in each case to approx. 0.2 mg of protease in the cleaning product concentrate.

The results for samples I and J were obtained in the same way as in example 7. For soiling K washing was followed by a visual assessment on a scale from 0 (=unchanged, i.e. very heavy soiling) to 10 (=no soiling perceptible). The results obtained are summarized in table 5 below. The averages from in each case 8 measurements are indicated therein.

TABLE 5

| Basic dishwashing agent with | I | J | K |
|---|---|---|---|
| Protease of the invention from *Bacillus gibsonii* (DSM 14391) | 39.8 | 69.5 | 7.1 |
| *B. lentus* alkaline protease F49 | 35.1 | 51.5 | 6.1 |
| Properase ® | 23.1 | 39.4 | 6.1 |

The higher contribution of the protease of the invention to the overall cleaning performance of the relevant product compared with the proteases *B. lentus* alkaline protease F49 and Properase® which are established for machine dishwashing products is also evident when the protease activities employed are higher.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed:

1. An isolated protein comprising a polypeptide that is at least 95% identical to SEQ ID NO:2, wherein the polypeptide exhibits alkaline protease activity.

2. The protein of claim 1 wherein the polypeptide comprises the amino acid sequence of SEQ ID NO:2.

3. An isolated protein comprising a polypeptide that is at least 95% identical to SEQ ID NO:3, wherein the polypeptide exhibits alkaline protease activity.

4. The protein of claim 3 wherein the polypeptide comprises the amino acid sequence of SEQ ID NO:3.

5. The protein of claim 1 encoded by a polynucleotide comprising a nucleotide sequence that is at least 95% identical to SEQ ID NO:1.

6. The protein of claim 2 encoded by a polynucleotide comprising the nucleotide sequence of SEQ ID NO:1.

7. The protein of claim 3 encoded by a polynucleotide comprising a nucleotide sequence that is at least 95% identical to nucleotides 343 to 1152 of SEQ ID NO:1.

8. The protein of claim 4 encoded by a polynucleotide comprising nucleotides 343 to 1152 of SEQ ID NO:1.

9. The protein of claim 1 wherein the protein is isolated from a micoroorganism.

10. The protein of claim 9 wherein the microorganism is a gram-positive bacterium.

11. The protein of claim 10 wherein the bacterium is of the genus *bacillus*.

12. The protein of claim 11 wherein the bacterium is of the species *Bacillus gibsonii*.

13. The protein of claim 11 wherein the bacterium is of the species *Bacillus gibsonii* (DSM 14391).

* * * * *

SEQUENCE LISTING

```
<160> NUMBER OF SEQ ID NOS: 17

<210> SEQ ID NO 1
<211> LENGTH: 1152
<212> TYPE: DNA
<213> ORGANISM: Bacillus Gibsonii (DSM 14391)
<220> FEATURE:
<221> NAME/KEY: CDS
<222> LOCATION: (1)..(1149)
<220> FEATURE:
<221> NAME/KEY: mat_peptide
<222> LOCATION: (343)..(1149)

<400> SEQUENCE: 1 atg aaa aga aga gta gga aag cta gtg gta ggg ctt gta tgt gtg        45
Met Lys Arg Arg Val Gly Lys Leu Val Val Gly Leu Val Cys Val
                -110                -105                -100 aca gct cta gta aca gtg aca gat tct gca tcg gca gca gaa gaa aag   93
Thr Ala Leu Val Thr Val Thr Asp Ser Ala Ser Ala Ala Glu Glu Lys
            -95                 -90                 -85 gta aag tac tta ata gga ttt gaa gaa gaa gca gag ctt gaa gcc ttc  141
Val Lys Tyr Leu Ile Gly Phe Glu Glu Glu Ala Glu Leu Glu Ala Phe
        -80                 -75                 -70 acg gag gaa gtt gac caa gta ggc gtg ttt tct gtt gaa gaa caa agt  189
Thr Glu Glu Val Asp Gln Val Gly Val Phe Ser Val Glu Glu Gln Ser
    -65                 -60                 -55 tta gta gag gat acg tta gat att gat gta gac att att gat gaa tat  237
Leu Val Glu Asp Thr Leu Asp Ile Asp Val Asp Ile Ile Asp Glu Tyr
-50                 -45                 -40
```

```
gat tat att gat gtg tta tct gta gaa tta gat ccg gaa gat gta gat      285
Asp Tyr Ile Asp Val Leu Ser Val Glu Leu Asp Pro Glu Asp Val Asp
-35             -30                 -25                 -20 gcg tta agt gag gaa gaa ggt att tct tat atc gaa gaa gac ttt gaa      333
Ala Leu Ser Glu Glu Glu Gly Ile Ser Tyr Ile Glu Glu Asp Phe Glu
            -15                 -10                 -5 cta tcg ata caa caa acc gtt cca tgg ggt att aca cgt gta caa gct      381
Leu Ser Ile Gln Gln Thr Val Pro Trp Gly Ile Thr Arg Val Gln Ala
        -1  1                   5                   10 ccc act gtg cat aat cgt gga ata aca gga tct gga gtt aaa gtc gct      429
Pro Thr Val His Asn Arg Gly Ile Thr Gly Ser Gly Val Lys Val Ala
        15                  20                  25 ata ctt gat aca ggt ata gct cag cat agt gat tta acc att cgt ggg      477
Ile Leu Asp Thr Gly Ile Ala Gln His Ser Asp Leu Thr Ile Arg Gly
30              35                  40                  45 gga gca agc ttt gta cca gga gag tca aca acg gct gat cta aat ggt      525
Gly Ala Ser Phe Val Pro Gly Glu Ser Thr Thr Ala Asp Leu Asn Gly
                50                  55                  60 cat ggt act cac gtt gct gga aca gtg gcc gct ctt aat aat tca att      573
His Gly Thr His Val Ala Gly Thr Val Ala Ala Leu Asn Asn Ser Ile
            65                  70                  75 ggt gtg atc ggt gtg gca cca agt gct gac cta tac gct gta aag gta      621
Gly Val Ile Gly Val Ala Pro Ser Ala Asp Leu Tyr Ala Val Lys Val
        80                  85                  90 tta gga gca aat ggt aga gga agc gtg agt ggg att gct caa ggt cta      669
Leu Gly Ala Asn Gly Arg Gly Ser Val Ser Gly Ile Ala Gln Gly Leu
    95                  100                 105 gag tgg gct gca acg aat aac atg cat att gca aac atg agt ctc ggt      717
Glu Trp Ala Ala Thr Asn Asn Met His Ile Ala Asn Met Ser Leu Gly
110             115                 120                 125 agt gat gca cct agc act aca tta gag cgt gca gtt aac tat gcg aca      765
Ser Asp Ala Pro Ser Thr Thr Leu Glu Arg Ala Val Asn Tyr Ala Thr
                130                 135                 140 agc cgt gga gtt ctc gtc att gcg gct act ggt aac aat ggt act ggt      813
Ser Arg Gly Val Leu Val Ile Ala Ala Thr Gly Asn Asn Gly Thr Gly
            145                 150                 155 tcc att ggc tac cca gct cgt tat gca aac gca atg gct gta gga gcg      861
Ser Ile Gly Tyr Pro Ala Arg Tyr Ala Asn Ala Met Ala Val Gly Ala
        160                 165                 170 act gac caa aac aac aga cgt gcg agc ttt tct caa tat ggc aca gga      909
Thr Asp Gln Asn Asn Arg Arg Ala Ser Phe Ser Gln Tyr Gly Thr Gly
    175                 180                 185 att gat att gtt gca cct ggt gtt gga att caa agc aca tac cta aat      957
Ile Asp Ile Val Ala Pro Gly Val Gly Ile Gln Ser Thr Tyr Leu Asn
190             195                 200                 205 aat agc tat gct agt atg cct gga aca tca atg gct aca cct cat gtt     1005
Asn Ser Tyr Ala Ser Met Pro Gly Thr Ser Met Ala Thr Pro His Val
                210                 215                 220 gct gga gta gct gcg ctt gtt aaa caa aaa aat cca tct tgg aat gcg     1053
Ala Gly Val Ala Ala Leu Val Lys Gln Lys Asn Pro Ser Trp Asn Ala
            225                 230                 235 act caa att cgt aat cat ttg aaa aat act gcg acg aat cta gga aac     1101
Thr Gln Ile Arg Asn His Leu Lys Asn Thr Ala Thr Asn Leu Gly Asn
        240                 245                 250 tca tct caa ttt ggt agt gga cta gtt aat gca gat gca gca acg cgc     1149
Ser Ser Gln Phe Gly Ser Gly Leu Val Asn Ala Asp Ala Ala Thr Arg
    255                 260                 265 taa                                                                 1152
```

<210> SEQ ID NO 2
<211> LENGTH: 383
<212> TYPE: PRT
<213> ORGANISM: Bacillus Gibsonii (DSM 14391)

<400> SEQUENCE: 2

```
Met Lys Arg Arg Val Gly Lys Leu Val Val Gly Leu Val Cys Val
              -110                -105                -100
Thr Ala Leu Val Thr Val Thr Asp Ser Ala Ser Ala Ala Glu Glu Lys
             -95                 -90                 -85
Val Lys Tyr Leu Ile Gly Phe Glu Glu Glu Ala Glu Leu Glu Ala Phe
            -80                 -75                 -70
Thr Glu Glu Val Asp Gln Val Gly Val Phe Ser Val Glu Glu Gln Ser
        -65                 -60                 -55
Leu Val Glu Asp Thr Leu Asp Ile Asp Val Asp Ile Ile Asp Glu Tyr
    -50                 -45                 -40
Asp Tyr Ile Asp Val Leu Ser Val Glu Leu Asp Pro Glu Asp Val Asp
-35                 -30                 -25                 -20
Ala Leu Ser Glu Glu Glu Gly Ile Ser Tyr Ile Glu Glu Asp Phe Glu
                -15                 -10                 -5
Leu Ser Ile Gln Gln Thr Val Pro Trp Gly Ile Thr Arg Val Gln Ala
         -1   1                   5                  10
Pro Thr Val His Asn Arg Gly Ile Thr Gly Ser Gly Val Lys Val Ala
             15                  20                  25
Ile Leu Asp Thr Gly Ile Ala Gln His Ser Asp Leu Thr Ile Arg Gly
30                  35                  40                  45
Gly Ala Ser Phe Val Pro Gly Glu Ser Thr Thr Ala Asp Leu Asn Gly
                50                  55                  60
His Gly Thr His Val Ala Gly Thr Val Ala Ala Leu Asn Asn Ser Ile
                65                  70                  75
Gly Val Ile Gly Val Ala Pro Ser Ala Asp Leu Tyr Ala Val Lys Val
            80                  85                  90
Leu Gly Ala Asn Gly Arg Gly Ser Val Ser Gly Ile Ala Gln Gly Leu
        95                 100                 105
Glu Trp Ala Ala Thr Asn Asn Met His Ile Ala Asn Met Ser Leu Gly
110                 115                 120                 125
Ser Asp Ala Pro Ser Thr Leu Glu Arg Ala Val Asn Tyr Ala Thr
                130                 135                 140
Ser Arg Gly Val Leu Val Ile Ala Ala Thr Gly Asn Asn Gly Thr Gly
            145                 150                 155
Ser Ile Gly Tyr Pro Ala Arg Tyr Ala Asn Ala Met Ala Val Gly Ala
            160                 165                 170
Thr Asp Gln Asn Asn Arg Arg Ala Ser Phe Ser Gln Tyr Gly Thr Gly
        175                 180                 185
Ile Asp Ile Val Ala Pro Gly Val Gly Ile Gln Ser Thr Tyr Leu Asn
190                 195                 200                 205
Asn Ser Tyr Ala Ser Met Pro Gly Thr Ser Met Ala Thr Pro His Val
                210                 215                 220
Ala Gly Val Ala Ala Leu Val Lys Gln Lys Asn Pro Ser Trp Asn Ala
            225                 230                 235
Thr Gln Ile Arg Asn His Leu Lys Asn Thr Ala Thr Asn Leu Gly Asn
        240                 245                 250
Ser Ser Gln Phe Gly Ser Gly Leu Val Asn Ala Asp Ala Ala Thr Arg
    255                 260                 265
```

<210> SEQ ID NO 3
<211> LENGTH: 269
<212> TYPE: PRT
<213> ORGANISM: Bacillus gibsonii (DSM 14391)

<400> SEQUENCE: 3

```
Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265
```

<210> SEQ ID NO 4
<211> LENGTH: 269
<212> TYPE: PRT
<213> ORGANISM: Bacillus alkalophilus

<400> SEQUENCE: 4

```
Gln Ser Val Pro Trp Gly Ile Ser Arg Val Gln Ala Pro Ala Ala His
1               5                   10                  15

Asn Arg Gly Leu Thr Gly Ser Gly Val Lys Val Ala Val Leu Asp Thr
            20                  25                  30

Gly Ile Ser Thr His Pro Asp Leu Asn Ile Arg Gly Gly Ala Ser Phe
        35                  40                  45

Val Pro Gly Glu Pro Ser Thr Gln Asp Gly Asn Gly His Gly Thr His
    50                  55                  60
```

```
Val Ala Gly Thr Ile Ala Ala Leu Asn Asn Ser Ile Gly Val Leu Gly
 65                  70                  75                  80

Val Ala Pro Asn Ala Glu Leu Tyr Ala Val Lys Val Leu Gly Ala Ser
                 85                  90                  95

Gly Ser Gly Ser Val Ser Ser Ile Ala Gln Gly Leu Glu Trp Ala Asn
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 269
<212> TYPE: PRT
<213> ORGANISM: Bacillus lentus

<400> SEQUENCE: 5

Ala Gln Ser Val Pro Trp Gly Ile Ser Arg Val Gln Ala Pro Ala Ala
1               5                  10                   15

His Asn Arg Gly Leu Thr Gly Ser Gly Val Lys Val Ala Val Leu Asp
                 20                 25                   30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly

```
                     165                 170                 175
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Thr Arg
            260                 265

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Thr Arg
            260                 265
```

<210> SEQ ID NO 7
<211> LENGTH: 268
<212> TYPE: PRT
<213> ORGANISM: Bacillus sp.

<400> SEQUENCE: 7

Gln Val Thr Pro Trp Gly Ile Thr Arg Val Gln Ala Pro Thr Ala Trp
1               5                   10                  15

Thr Arg Gly Tyr Thr Gly Thr Gly Val Arg Val Ala Val Leu Asp Thr
                20                  25                  30

Gly Ile Ser Thr His Pro Asp Leu Asn Ile Arg Gly Gly Val Ser Phe
            35                  40                  45

Val Pro Gly Glu Pro Ser Tyr Gln Asp Gly Asn Gly His Gly Thr His
    50                  55                  60

Val Ala Gly Thr Ile Ala Ala Leu Asn Asn Ser Ile Gly Val Val Gly
65                  70                  75                  80

Val Ala Pro Asn Ala Glu Leu Tyr Ala Val Lys Val Leu Gly Ala Asn
                85                  90                  95

Gly Ser Gly Ser Val Ser Ser Ile Ala Gln Gly Leu Gln Trp Thr Ala
            100                 105                 110

Gln Asn Asn Ile His Val Ala Asn Leu Ser Leu Gly Ser Pro Val Gly
        115                 120                 125

Ser Gln Thr Leu Glu Leu Ala Val Asn Gln Ala Thr Asn Ala Gly Val
    130                 135                 140

Leu Val Val Ala Ala Thr Gly Asn Asn Gly Ser Gly Thr Val Ser Tyr
145                 150                 155                 160

Pro Ala Arg Tyr Ala Asn Ala Leu Ala Val Gly Ala Thr Asp Gln Asn
                165                 170                 175

Asn Asn Arg Ala Ser Phe Ser Gln Tyr Gly Thr Gly Leu Asn Ile Val
            180                 185                 190

Ala Pro Gly Val Gly Ile Gln Ser Thr Tyr Pro Gly Asn Arg Tyr Ala
        195                 200                 205

Ser Leu Ser Gly Thr Ser Met Ala Thr Pro His Val Ala Gly Val Ala
    210                 215                 220

Ala Leu Val Lys Gln Lys Asn Pro Ser Trp Ser Asn Thr Gln Ile Arg
225                 230                 235                 240

Gln His Leu Thr Ser Thr Ala Thr Ser Leu Gly Asn Ser Asn Gln Phe
                245                 250                 255

Gly Ser Gly Leu Val Asn Ala Glu Ala Ala Thr Arg
            260                 265

<210> SEQ ID NO 8
<211> LENGTH: 268
<212> TYPE: PRT
<213> ORGANISM: Bacillus Ya-B

<400> SEQUENCE: 8

Gln Thr Val Pro Trp Gly Ile Asn Arg Val Gln Ala Pro Ile Ala Gln
1               5                   10                  15

Ser Arg Gly Phe Thr Gly Thr Gly Val Arg Val Ala Val Leu Asp Thr
                20                  25                  30

Gly Ile Ser Asn His Ala Asp Leu Arg Ile Arg Gly Gly Ala Ser Phe
            35                  40                  45

Val Pro Gly Glu Pro Asn Ile Ser Asp Gly Asn Gly His Gly Thr Gln
    50                  55                  60

-continued

Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                 85                  90                  95

Gly Ser Gly Ser Ile Ser Gly Ile Ala Gln Gly Leu Gln Trp Ala Ala
            100                 105                 110

Asn Asn Gly Met His Ile Ala Asn Met Ser Leu Gly Ser Ser Ala Gly
        115                 120                 125

Ser Ala Thr Met Glu Gln Ala Val Asn Gln Ala Thr Ala Ser Gly Val
    130                 135                 140

Leu Val Val Ala Ser Ser Gly Asn Ser Gly Ala Gly Asn Val Gly Phe
145                 150                 155                 160

Pro Ala Arg Tyr Ala Asn Ala Met Ala Val Gly Ala Thr Asp Gln Asn
                165                 170                 175

Asn Asn Arg Ala Thr Phe Ser Gln Tyr Gly Ala Gly Leu Asp Ile Val
            180                 185                 190

Ala Pro Gly Val Gly Val Gln Ser Thr Val Pro Gly Asn Gly Tyr Ala
        195                 200                 205

Ser Phe Asn Gly Thr Ser Met Ala Thr Pro His Val Ala Gly Val Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Thr Gln Phe
                245                 250                 255

Gly Ser Gly Leu Val Asn Ala Glu Ala Ala Thr Arg
            260                 265

<210> SEQ ID NO 9
<211> LENGTH: 272
<212> TYPE: PRT
<213> ORGANISM: Bacillus sp.

<400> SEQUENCE: 9

Gln Thr Val Pro Trp Gly Ile Pro Tyr Ile Tyr Ser Asp Val Val His
 1               5                  10                  15

Arg Gln Gly Tyr Phe Gly Asn Gly Val Lys Val Ala Val Leu Asp Thr
                20                  25                  30

Gly Val Ala Pro His Pro Asp Leu His Ile Arg Gly Gly Val Ser Phe
            35                  40                  45

Ile Ser Thr Glu Asn Thr Tyr Val Asp Tyr Asn Gly His Gly Thr His
 50                  55                  60

Val Ala Gly Thr Val Ala Ala Leu Asn Asn Ser Tyr Gly Val Leu Gly
 65                  70                  75                  80

Val Ala Pro Gly Ala Glu Leu Tyr Ala Val Lys Val Leu Asp Arg Asn
                 85                  90                  95

Gly Ser Gly Ser His Ala Ser Ile Ala Gln Gly Ile Glu Trp Ala Met
            100                 105                 110

Asn Asn Gly Met Asp Ile Ala Asn Met Ser Leu Gly Ser Pro Ser Gly
        115                 120                 125

Ser Thr Thr Leu Gln Leu Ala Ala Asp Arg Ala Arg Asn Ala Gly Val
    130                 135                 140

Leu Leu Ile Gly Ala Ala Gly Asn Ser Gly Gln Gln Gly Gly Ser Asn
145                 150                 155                 160

Asn Met Gly Tyr Pro Ala Arg Tyr Ala Ser Val Met Ala Val Gly Ala
                165                 170                 175

```
Val Asp Gln Asn Gly Asn Arg Ala Asn Phe Ser Ser Tyr Gly Ser Glu
            180                 185                 190

Leu Glu Ile Met Ala Pro Gly Val Asn Ile Asn Ser Thr Tyr Leu Asn
        195                 200                 205

Asn Gly Tyr Arg Ser Leu Asn Gly Thr Ser Met Ala Ser Pro His Val
        210                 215                 220

Ala Gly Val Ala Ala Leu Val Lys Gln Lys His Pro His Leu Thr Ala
225                 230                 235                 240

Ala Gln Ile Arg Asn Arg Met Asn Gln Thr Ala Ile Pro Leu Gly Asn
                245                 250                 255

Ser Thr Tyr Tyr Gly Asn Gly Leu Val Asp Ala Glu Tyr Ala Ala Gln
        260                 265                 270

<210> SEQ ID NO 10
<211> LENGTH: 274
<212> TYPE: PRT
<213> ORGANISM: Bacillus subtilis var.

<400> SEQUENCE: 10

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser Gly
    50                  55                  60

His Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Ser Thr Ile Ala Val
                165                 170                 175

Gly Ala Val Asn Ser Ser Asn Gln Arg Ala Ser Phe Ser Ser Val Gly
            180                 185                 190

Ser Glu Leu Asp Val Met Ala Pro Gly Val Ser Ile Gln Ser Thr Leu
        195                 200                 205

Pro Gly Gly Thr Tyr Gly Ala Tyr Asn Gly Thr Ser Met Ala Thr Pro
    210                 215                 220

His Val Ala Gly Ala Ala Ala Leu Ile Leu Ser Lys His Pro Thr Trp
225                 230                 235                 240

Thr Asn Ala Gln Val Arg Asp Arg Leu Glu Ser Thr Ala Thr Tyr Leu
                245                 250                 255

Gly Asn Ser Phe Tyr Tyr Gly Lys Gly Leu Ile Asn Val Gln Ala Ala
            260                 265                 270

Ala Gln
```

<210> SEQ ID NO 11
<211> LENGTH: 275
<212> TYPE: PRT
<213> ORGANISM: Bacillus amyloliquefaciens

<400> SEQUENCE: 11

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 12
<211> LENGTH: 274
<212> TYPE: PRT
<213> ORGANISM: Bacillus licheniformis

<400> SEQUENCE: 12

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                 85                  90                  95

Ser Ser Gly Ser Gly Thr Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Ser Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 13
<211> LENGTH: 275
<212> TYPE: PRT
<213> ORGANISM: Bacillus pumilus

<400> SEQUENCE: 13

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
 50                  55                  60

Gly Thr His Val Ala Gly Thr Ile Ala Ala Leu Asn Asn Ser Ile Gly
65                  70                  75                  80

Val Leu Gly Val Ala Pro Ser Ser Ala Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

```
Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
            165                 170                 175

Val Gly Ala Val Asn Ser Ala Asn Gln Arg Ala Ser Phe Ser Ser Ala
            180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 14
<211> LENGTH: 275
<212> TYPE: PRT
<213> ORGANISM: Bacillus amylosacchariticus

<400> SEQUENCE: 14

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
            115                 120                 125

Pro Ser Gly Ser Thr Ala Leu Lys Thr Val Val Asp Lys Ala Val Ser
130                 135                 140

Ser Gly Ile Val Val Ala Ala Ala Gly Asn Glu Gly Ser Ser Gly
145                 150                 155                 160

Ser Ser Ser Thr Val Gly Tyr Pro Ala Lys Tyr Pro Ser Thr Ile Ala
            165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Ala Leu Ile Leu Ser Lys His Pro Thr
```

```
                225                 230                 235                 240
Trp Thr Asn Ala Gln Val Arg Asp Arg Leu Glu Ser Thr Ala Thr Tyr
                245                 250                 255
Leu Gly Asn Ser Phe Tyr Tyr Gly Lys Gly Leu Ile Asn Val Gln Ala
                260                 265                 270
Ala Ala Gln
        275

<210> SEQ ID NO 15
<211> LENGTH: 275
<212> TYPE: PRT
<213> ORGANISM: Geobacillus stearothermophilus

<400> SEQUENCE: 15

Ala Gln Ser Val Pro Tyr Gly Ile Ser Gln Ile Lys Ala Pro Ala Leu
1               5                   10                  15
His Ser Gln Gly Tyr Thr Gly Ser Asn Val Lys Val Ala Val Ile Asp
                20                  25                  30
Ser Gly Ile Asp Ser Ser His Pro Asp Leu Asn Val Arg Gly Gly Ala
            35                  40                  45
Ser Phe Val Pro Ser Glu Thr Asn Pro Tyr Gln Asp Gly Ser Ser His
    50                  55                  60
Gly Thr His Val Ala Gly Thr Ile Ala Ala Leu Asn Asn Ser Ile Gly
65                  70                  75                  80
Val Leu Gly Val Ser Pro Ser Ala Ser Leu Tyr Ala Val Lys Val Leu
                85                  90                  95
Asp Ser Thr Gly Ser Gly Gln Tyr Ser Trp Ile Ile Asn Gly Ile Glu
            100                 105                 110
Trp Ala Ile Ser Asn Asn Met Asp Val Ile Asn Met Ser Leu Gly Gly
        115                 120                 125
Pro Ser Gly Ser Thr Ala Leu Lys Thr Val Val Asp Lys Ala Val Ser
    130                 135                 140
Ser Gly Ile Val Val Ala Ala Ala Gly Asn Glu Gly Ser Ser Gly
145                 150                 155                 160
Ser Ser Ser Thr Val Gly Tyr Pro Ala Lys Tyr Pro Ser Thr Ile Ala
                165                 170                 175
Val Gly Ala Val Asn Ser Ser Asn Gln Arg Ala Ser Phe Ser Ser Ala
            180                 185                 190
Gly Ser Glu Leu Asp Val Met Ala Pro Gly Val Ser Ile Gln Ser Thr
        195                 200                 205
Leu Pro Gly Gly Thr Tyr Gly Ala Tyr Asn Gly Thr Ser Met Ala Thr
    210                 215                 220
Pro His Val Ala Gly Ala Ala Ala Leu Ile Leu Ser Lys His Pro Thr
225                 230                 235                 240
Trp Thr Asn Ala Gln Val Arg Asp Arg Leu Glu Ser Thr Ala Thr Tyr
                245                 250                 255
Leu Gly Asn Ser Phe Tyr Tyr Gly Lys Gly Leu Ile Asn Val Gln Ala
                260                 265                 270
Ala Ala Gln
        275

<210> SEQ ID NO 16
<211> LENGTH: 275
<212> TYPE: PRT
<213> ORGANISM: Bacillus subtilis
```

-continued

```
<400> SEQUENCE: 16

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: succinyl
<220> FEATURE:
<221> NAME/KEY: MISC_FEATURE
<222> LOCATION: (4)..(4)
<223> OTHER INFORMATION: p-nitroanilide

<400> SEQUENCE: 17

Ala Ala Pro Phe
1
```